US012616698B2

(12) United States Patent
Lee et al.

(10) Patent No.: US 12,616,698 B2
(45) Date of Patent: *May 5, 2026

(54) METHODS FOR REDUCING LIVER FAT AND FOR TREATING FATTY LIVER DISORDERS

(71) Applicant: Corcept Therapeutics Incorporated, Menlo Park, CA (US)

(72) Inventors: Ada Lee, Menlo Park, CA (US); Andreas Grauer, Westlake Village, CA (US); Joseph Belanoff, Woodside, CA (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 371 days.

This patent is subject to a terminal disclaimer.

(21) Appl. No.: 18/518,289

(22) Filed: Nov. 22, 2023

(65) Prior Publication Data

US 2024/0100052 A1 Mar. 28, 2024

Related U.S. Application Data

(63) Continuation-in-part of application No. 17/736,912, filed on May 4, 2022, now abandoned.

(Continued)

(51) Int. Cl.
*A61K 31/513* (2006.01)
*A61P 1/16* (2006.01)

(52) U.S. Cl.
CPC .............. *A61K 31/513* (2013.01); *A61P 1/16* (2018.01)

(58) Field of Classification Search
CPC ................................ A61K 31/513; A61P 1/16
See application file for complete search history.

(56) References Cited

U.S. PATENT DOCUMENTS

| | | | |
|---|---|---|---|
| 2,153,546 A | 4/1939 | Camp | |
| 4,963,558 A | 10/1990 | Hotten et al. | |
| | (Continued) | | |

FOREIGN PATENT DOCUMENTS

| | | | |
|---|---|---|---|
| BR | 112017007860 | | 1/2018 |
| CL | 2013002667 A1 | | 5/2014 |
| | (Continued) | | |

OTHER PUBLICATIONS

"Statement on a Nonproprietary Name Adopted by The Usan Council—Miricorilant", Available online at https://searchlf.ama-assn.org/ usan/documentDownload uri=/unstructured/binary/usan/miricorilant.pdf, XP093318159, Jul. 31, 2019, 1 page.

(Continued)

*Primary Examiner* — San Ming R Hui

(74) *Attorney, Agent, or Firm* — Kilpatrick Townsend & Stockton LLP

(57) ABSTRACT

Applicant discloses methods and compositions for reducing liver fat and for treating fatty liver diseases (e.g., non-alcoholic fatty liver disease (NAFLD) including nonalcoholic steatohepatitis (NASH) and nonalcoholic cirrhosis; alcohol related fatty liver diseases including, alcohol fatty liver disease (AFL), alcoholic steatohepatitis (ASH), and alcoholic cirrhosis; and liver fibrosis). Significant liver fat reductions were obtained in human patients after only between 30 to 44 days of administration of 600 mg/day or 900 mg/day of the cyclohexyl pyrimidine glucocorticoid receptor modulator miricorilant. Liver fat reductions ranged from 38.5% to 73.8% (magnetic resonance imaging measurements in 4 of 5 patients receiving miricorilant, measured (Continued)

between 16-64 days after cessation of miricorilant admin-istration). A further effect of miricorilant was an increase in liver alanine amino transferase (ALT) and aspartate amino transferase (AST). Mouse studies showed that miricorilant reduced measures of NAFLD, body weight, liver weight, and liver collagen and galectin-3 levels.

11 Claims, 25 Drawing Sheets

Related U.S. Application Data

(60) Provisional application No. 63/271,861, filed on Oct. 26, 2021, provisional application No. 63/244,116, filed on Sep. 14, 2021, provisional application No. 63/184,694, filed on May 5, 2021.

(56) References Cited

U.S. PATENT DOCUMENTS

| | | | |
|---|---|---|---|
| 5,929,058 | A | 7/1999 | Deisher |
| 6,150,349 | A | 11/2000 | Schatzberg et al. |
| 6,369,046 | B1 | 4/2002 | Schatzberg et al. |
| 6,680,310 | B2 | 1/2004 | Belanoff et al. |
| 6,852,719 | B2 | 2/2005 | Liu et al. |
| 7,576,076 | B2 | 8/2009 | Clark et al. |
| 7,678,813 | B2 | 3/2010 | Clark et al. |
| 7,745,657 | B2 | 6/2010 | Ali et al. |
| 7,790,745 | B2 | 9/2010 | Yang et al. |
| 7,799,782 | B2 | 9/2010 | Munson et al. |
| 7,928,237 | B2 | 4/2011 | Clark et al. |
| 8,173,664 | B2 | 5/2012 | Clark et al. |
| 8,324,203 | B2 | 12/2012 | Clark et al. |
| 8,461,172 | B2 | 6/2013 | Clark et al. |
| 8,557,839 | B2 | 10/2013 | Clark et al. |
| 8,598,154 | B2 | 12/2013 | Clark et al. |
| 8,685,973 | B2 | 4/2014 | Clark et al. |
| 8,716,327 | B2 | 5/2014 | Zhao et al. |
| 8,859,774 | B2 | 10/2014 | Hunt et al. |
| 8,889,867 | B2 | 11/2014 | Clark et al. |
| 8,906,917 | B2 | 12/2014 | Clark et al. |
| 8,969,557 | B2 | 3/2015 | Harriman et al. |
| 9,273,047 | B2 | 3/2016 | Hunt et al. |
| 9,321,736 | B2 | 4/2016 | Clark et al. |
| 9,422,323 | B2 | 8/2016 | Houpis et al. |
| 9,447,089 | B2 | 9/2016 | Desai et al. |
| 9,707,223 | B2 | 7/2017 | Hunt et al. |
| 9,943,505 | B2 | 4/2018 | Hunt et al. |
| 9,956,216 | B2 | 5/2018 | Hunt et al. |
| 10,047,082 | B2 | 8/2018 | Hunt et al. |
| 10,117,852 | B2 | 11/2018 | Hunt et al. |
| 10,213,414 | B2 | 2/2019 | Hunt et al. |
| 10,238,659 | B2 | 3/2019 | Belanoff et al. |
| 10,323,034 | B2 | 6/2019 | Hunt et al. |
| 10,787,449 | B2 | 9/2020 | Hunt et al. |
| 10,881,660 | B2 | 1/2021 | Belanoff et al. |
| 11,590,135 | B2 | 2/2023 | Belanoff et al. |
| 2006/0128688 | A1 | 6/2006 | Tonnaer |
| 2006/0223852 | A1 | 10/2006 | Gillespie et al. |
| 2007/0066557 | A1 | 3/2007 | Monia et al. |
| 2007/0281928 | A1 | 12/2007 | Clark et al. |
| 2008/0070950 | A1 | 3/2008 | Benjamin et al. |
| 2009/0312246 | A1 | 12/2009 | Baron et al. |
| 2010/0004326 | A1 | 1/2010 | Veverka |
| 2010/0144764 | A1 | 6/2010 | Huang et al. |
| 2010/0179115 | A1 | 7/2010 | Belanoff |
| 2010/0292477 | A1 | 11/2010 | Clark et al. |
| 2010/0298282 | A1 | 11/2010 | Roach et al. |
| 2010/0311717 | A1 | 12/2010 | McIntosh et al. |
| 2011/0166110 | A1 | 7/2011 | Clark et al. |
| 2012/0220565 | A1 | 8/2012 | Clark et al. |
| 2013/0072486 | A1 | 3/2013 | Clark et al. |
| 2013/0225633 | A1 | 8/2013 | Hunt et al. |
| 2014/0315866 | A1 | 10/2014 | Pan et al. |
| 2015/0148341 | A1 | 5/2015 | Hunt et al. |
| 2016/0106749 | A1 | 4/2016 | Belanoff et al. |
| 2019/0151318 | A1 | 5/2019 | Belanoff et al. |
| 2021/0177848 | A1 | 6/2021 | Lee et al. |
| 2022/0370466 | A1 | 11/2022 | Lee et al. |

FOREIGN PATENT DOCUMENTS

| | | | |
|---|---|---|---|
| CN | 1965840 | A | 5/2007 |
| CN | 101313066 | A | 11/2008 |
| CN | 103596431 | A | 2/2014 |
| CN | 107106562 | A | 8/2017 |
| EP | 0037495 | A1 | 10/1981 |
| EP | 0145121 | A2 | 6/1985 |
| EP | 0369627 | A2 | 5/1990 |
| EP | 0375210 | A1 | 6/1990 |
| EP | 375210 | B1 | 5/1995 |
| EP | 0722732 | A1 | 7/1996 |
| EP | 1778236 | A1 | 5/2007 |
| EP | 1778236 | B1 | 7/2010 |
| EP | 3206692 | A1 | 8/2017 |
| EP | 3074011 | B1 | 7/2019 |
| IL | 251729 | A | 5/2017 |
| JP | 322220 | B1 | 4/1957 |
| JP | 04368384 | A | 12/1992 |
| JP | 06128238 | A | 5/1994 |
| JP | 09505030 | A | 5/1997 |
| JP | 1017555 | | 1/1998 |
| JP | 2002506032 | A | 2/2002 |
| JP | 2002544271 | A | 12/2002 |
| JP | 2005533785 | A | 11/2005 |
| JP | 2009508527 | A | 5/2009 |
| JP | 2014508175 | A | 4/2014 |
| JP | 2017531013 | A | 10/2017 |
| KR | 20170066646 | A | 6/2017 |
| SG | 11201703024 | | 10/2019 |
| WO | 9410150 | A1 | 5/1994 |
| WO | 9504734 | A1 | 2/1995 |
| WO | 9945925 | A1 | 9/1999 |
| WO | 0069846 | A1 | 11/2000 |
| WO | 0244120 | A1 | 6/2002 |
| WO | 03009853 | A1 | 2/2003 |
| WO | 03015692 | A2 | 2/2003 |
| WO | 03061651 | A1 | 7/2003 |
| WO | 03084935 | A2 | 10/2003 |
| WO | 03105838 | A2 | 12/2003 |
| WO | 2004009017 | A2 | 1/2004 |
| WO | 2004065351 | A1 | 8/2004 |
| WO | 2005087769 | A1 | 9/2005 |
| WO | 2009058944 | A2 | 5/2009 |
| WO | 2010132445 | A1 | 11/2010 |
| WO | 2011140228 | A1 | 11/2011 |
| WO | 2012027702 | A1 | 3/2012 |
| WO | 2012094618 | A1 | 7/2012 |
| WO | 2012129074 | A1 | 9/2012 |
| WO | 2013177559 | A2 | 11/2013 |
| WO | 2016061195 | | 4/2016 |
| WO | 2019236487 | A1 | 12/2019 |

OTHER PUBLICATIONS

U.S. Appl. No. 18/386,828, "Non-Final Office Action", filed Oct. 21, 2025, 22 pages.

European Patent Application No. 20900160.1, "Office Action", Sep. 30, 2025, 8 pages.

Hunt, et al., "Discovery of a Novel Non-Steroidal GR Antagonist with in Vivo Efficacy in the Olanzapine-Induced Weight Gain Model in the Rat", Database accession No. 2012:1629310, Jan. 1, 2012, 2 pages.

Tang, et al., "Cross-sectional and Longitudinal Evaluation of Liver Volume and Total Liver Fat Burden in Adults With Nonalcoholic Steatohepatitis", Abdominal Imaging, vol. 40, Jul. 13, 2014, pp. 26-37.

"Amorphous Solid", Wikipedia, Available Online at: http://en.wikipedia.org/wiki/Amorphous_solid, Jan. 16, 2014, pp. 1-3.

"Antipsychotic Drugs: the Weight Problem", Harvard Mental Health Letter, Harvard Health Online, Dec. 2000, 3 pages.

(56)  References Cited

OTHER PUBLICATIONS

"Clinical Trials", NCT03877562, Available Online at: https://clinicaltrials.gov/ct2/show/NCT03877562, 2019, 7 pages.

"Corcept Therapeutics", Available Online at: https://seekingalpha.com/article/4304715-corcept-therapeutics-cort-ceo-joseph-belanoff-on-q3-2019-results-earnings-call-transcript, Mar. 15, 2019, 7 pages.

"Database Crossfile Beilstein", Beilstein Institut Zur Foerderung der Chemischen Wissenschaft, Accession No. 101172-52-5 (BRN), Jun. 27, 1988, 3 pages.

"Highlights of Prescribing Information", Korlym® (Mifepristone), Concept Therapeutics Incorporated, 2017, pp. 1-7.

"International Nonproprietary Names for Pharmaceutical Substances (INN)", World Health Organization Drug Information, vol. 32, No. 2, Jun. 9, 2018, pp. 283-398.

U.S. Appl. No. 12/777,340 , "Declaration Under 37 CFR 1.132 by Robin Clark", Solid Forms and Process for Preparing, Feb. 2013, 5 pages.

U.S. Appl. No. 14/549,885 , "First Hunt Declaration", filed Jan. 18, 2017, pp. 1-4.

U.S. Appl. No. 14/549,885 , "Second Hunt Declaration", filed Jul. 7, 2017, 14 pages.

U.S. Appl. No. 14/549,885 , "U.S. Patent Application No.", Octahydro Fused Azadecalin Glucocorticoid Receptor Modulators, filed Nov. 21, 2014, 91 pages.

U.S. Appl. No. 16/036,001 , "U.S. Patent Application No.", Octahydro Fused Azadecalin Glucocorticoid Receptor Modulators, filed Jul. 16, 2018, 91 pages.

U.S. Appl. No. 16/161,642 , "U.S. Patent Application No.", Octahydro Fused Azadecalin Glucocorticoid Receptor Modulators, filed Oct. 16, 2018, 107 pages.

Allison et al., "Antipsychotic-Induced Weight Gain: A Comprehensive Research Synthesis", American Journal of Psychiatry, vol. 156, No. 11, Nov. 11, 1999, pp. 1686-1696.

Andrews et al., "Glucocorticoids and Insulin Resistance: Old Hormones, New Targets", Clinical Science, vol. 96, No. 5, Jun. 1999, pp. 513-523.

Asensio et al., "Role of Glucocorticoids in the Physiopathology of Excessive Fat Deposition and Insulin Resistance", International Journal of Obesity, vol. 28, Dec. 13, 2004, pp. S45-S52.

Baptista et al., "Body Weight Gain After Administration of Antipsychotic Drugs: Correlation With Leptin, Insulin and Reproductive Hormones", Pharmacopsychiatry, vol. 33, No. 3, May 2000, pp. 81-88.

Baptista , "Body Weight Gain Induced by Antipsychotic Drugs: Mechanisms and Management", Acta Psychiatrica Scandinavica, vol. 100, No. 1, Jul. 1999, pp. 3-16.

Barth et al., "Structural and Stereoelectronic Requirements for the Inhibition of Mammalian 2,3-Oxidosqualene Cyclase by Substituted Isoquinoline Derivatives", Journal of Medicinal Chemistry, vol. 39, No. 12, Jun. 7, 1996, pp. 2302-2312.

Belanoff et al., "Selective Glucocorticoid Receptor (Type II) Antagonist Prevents and Reverses Olanzapine-induced Weight Gain", Diabetes, Obesity and Metabolism, vol. 12, 2010, pp. 545-547.

Belanoff et al., "Selective Glucocorticoid Receptor (Type II) Antagonistprevents and Reverses Olanzapine-induced Weight Gain", Diabetes, Obesity and Metabolism, vol. 12, No. 6, Jun. 2010, pp. 545-547.

Bhuyan et al., "Studies on Uracils: Synthesis of Novel Uracil Analogues via 1,5- and 1,6-Intramolecular Cycloaddition Reactions", Journal of Chemical Research, Synopses, vol. 9, 1998, pp. 502-503.

Blackburn , "Weight Gain and Antipsychotic Medication", The Journal of Clinical Psychiatry, vol. 61, No. 8, 2000, pp. 36-41.

Bledsoe et al., "Crystal Structure of the Glucocorticoid Receptor Ligand Binding Domain Reveals a Novel Mode of Receptor Dimerization and Coactivator Recognition", Cell, vol. 110, No. 1, Jul. 12, 2002, pp. 93-105.

Bofelli et al., "Glucocorticold Antagonists Improve Insulin Sensitivity in Mice", 741•P, Obesity, Integrative Physiology of Obesity, vol. 18, Supplement 2, Nov. 2010, 1 page.

Christoffers et al., "Absolute Configuration of Methyl (+)-1,2,3,4,6,7,8,8a-Octahydro-6-Isoquinolone-8a-Carboxylate and Stereochemistry of a Copper-Catalyzed Asymmetric Michael Reaction", Zeitschrift Fuer Naturforschung B Chemical Sciences, vol. 59, No. 4, Apr. 1, 2004, pp. 375-379.

Christoffers et al., "Copper-Catalyzed Asymmetric Michael Reactions with α-Amino Acid Amides: Synthesis of an Optically Active Piperidine Derivative", Wiley Online Library, vol. 2002, No. 9, May 2002, pp. 1505-1508.

Christoffers et al., "Synthesis of an Optically Active Decahydro-6-Isoquinolone Scaffold with a Quaternary Stereocenter", Wiley Online Library, vol. 2004, No. 12, Jun. 2004, pp. 2701-2706.

Christoffers , "Transformation of an Optically Active Decahydro-6-isoquinolone Scaffold: Perfect Felkin-Anh Diastereoselectivity", Organic Letters, vol. 6, No. 7, Feb. 3, 2004, pp. 1171-1173.

Chu , "Connecting via Winsock to SIN at PTO-STN on Port 23", STN-12691012, STN International, Mar. 19, 2012, 62 pages.

Chu et al., "Successful Long-Term Treatment of Refractory Cushing's Disease with High-Dose Mifepristone (RU 486)", The Journal of Clinical Endocrinology & Metabolism, vol. 86, No. 8, Aug. 2001, pp. 3568-3573.

Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, No. 4, Feb. 15, 2008, pp. 1312-1317.

Dibas et al., "Glucocorticoid Therapy and Ocular Hypertension", European Journal of Pharmacology, vol. 787, Sep. 15, 2016, pp. 1-33.

Dorwald , "Side Reactions in Organic Synthesis", Wiley: VCH, Weinheim. Preface and Chapter 1, 2005, 18 pages.

D'Souza et al., "Consumption of a High-Fat Diet Rapidly Exacerbates the Development of Fatty Liver Disease that Occurs with Chronically Elevated Glucocorticoids", American Journal of Physiology-Gastrointestinal and Liver Physiology, vol. 302, Jan. 19, 2012, pp. G850-G861.

Elmore et al., "Nonsteroidal Selective Glucocorticoid Modulators: The Effect of C-5 Alkyl Substitution on the Transcriptional Activation/Repression Profile of 2,5-Dihydro-10-Methoxy-2,2,4-Trimethyl-1H-[1]Benzopyrano[3,4-f]Quinolines", American Chemical Society, Journal of Medicinal Chemistry, vol. 44, No. 25, Dec. 1, 2001, pp. 4481-4491.

Application No. EP22799415.9 , Extended European Search Report, Mailed on Feb. 19, 2025, 7 pages.

Friedman et al., "Phosphoenolpyruvate Carboxykinase (GTP) Gene Transcription and Hyperglycemia are Regulated by Glucocorticoids in Genetically Obese db/db Transgenic Mice", Journal of Biological Chemistry, vol. 272, No. 50, Dec. 12, 1997, pp. 31475-31481.

Fukazawa et al., "6-Amino-5-Methyluracil Derivatives and Their Use as Thymidine Phosphorylase Inhibitors and Neovascularization Inhibitors", XP002355358; Database CA Online; Chemical Abstracts Service; Database Accession No. 1998:59356, Abstract, 1998, 4 pages.

Gasparini et al., "Peripheral Markers in Testing Pathophysiological Hypotheses and Diagnosis Alzheimer's Disease", Federation of American Societies for Experimental Biology Journal, vol. 12, No. 1, Jan. 1998, pp. 17-34.

Gauthier et al., "Alzheimer's Disease: Current Knowledge, Management and Research", Canadian Medical Association Journal, vol. 157, No. 8, Oct. 15, 1997, pp. 1047-1052.

Genck , "A Number of Factors can Affect Solids Formation", Available Online at: https://www.chemicalprocessing.com/articles/2010/210/?page=print, 2004, pp. 1-8.

Genck , "Make the Most of Antisolvent Crystallization: A Number of Factors Can Affect Solids' Formation", Chemical Processing, vol. 73, No. 12, Nov. 8, 2010, 8 pages.

Gettys et al., "RU-486 (Mifepristone) Ameliorates Diabetes but Does Not Correct Deficient ß-Adrenergic Signalling in Adipocytes From Mature C57BL/6J-ob/ob Mice", International Journal of Obesity, vol. 21, No. 10, Oct. 1997, pp. 865-873.

Green et al., "Weight Gain From Novel Antipsychotic Drugs: Need for Action", General Hospital Psychiatry, vol. 22, No. 4, Jul.-Aug. 2000, pp. 224-235.

(56)　　　　　References Cited

OTHER PUBLICATIONS

Greicius et al., "Presenile Dementia Syndrome: An Update on Taxonomy and Diagnosis", Journal of Neurology, Neurosurgery & Psychiatry, vol. 72, No. 6, Jun. 1, 2002, pp. 691-700.

Gross et al., "Mifepristone Reduces Weight Gain and Improves Metabolic Abnormalities Associated With Risperidone Treatment in Normal Men", Obesity, vol. 18, No. 12, Dec. 1, 2010, pp. 2295-2300.

Gross et al., "Mifepristone Treatment of Olanzapine-induced Weight Gain in Healthy Men", Advances in Therapy, vol. 26, No. 10, Oct. 1, 2009, pp. 959-969.

Gupta et al., "Studies on Carboxylation in Heterocyclic Systems", Journal of Scientific and Industrial Research, vol. 20B, Aug. 1961, pp. 394-397.

Hsin et al., "Stereoselective Synthesis of Morphine Fragments Trans- and Cis-Octahydro-1H-Benzo[4,5]Furo[3,2-e]Isoquinolines", Tetrahedron, vol. 61, No. 2, Jan. 10, 2005, pp. 513-520.

Hunt et al., "Identification of the Clinical Candidate (R)-(1-(4-Fluorophenyl)-6-((1-Methyl-1H-Pyrazol-4-yl)Sulfonyl)-4,4a,5,6,7,8-Hexahydro-1H-Pyrazolo[3,4-g]Isoquinolin-4a-yl)(4-(Trifluoromethyl)Pyridin-2-yl) (CORT125134): A Selective Glucocorticoid Receptor (GR) Anta", Journal of Medicinal Chemistry, vol. 60, No. 8, Apr. 27, 2017, pp. 3405-3421.

Johnson et al., "Relationships Between Drug Activity in NCI Preclinical in Vitro and in Vivo Models and Early Clinical Trials", British Journal of Cancer, vol. 84, No. 10, May 18, 2001, pp. 1424-1431.

Application No. JP2007-503030 , Office Action, Mailed on Feb. 23, 2011, 8 pages.

Katsiki et al., "Effects of Sodium-glucose Co-transporter-2 (SGLT2) Inhibitors on Non-alcoholic Fatty Liver Disease/non-alcoholic Steatohepatitis: Ex Quo Et Quo Vadimus?", Metabolism Clinical and Experimental, vol. 98, Sep. 2019, 7 pages.

Kugita , "Studies on the Syntheses of Hydrogenated Quinolines and Isoquinolines as Analgesics", Pharmaceutical Bulletin, vol. 4, No. 1, Feb. 1956, pp. 29-34.

Lee et al., "Reversal of Antipsychotic-induced Weight Gain in Rats With Miricorilant, a Selective Glucocorticoid Receptor (GR) Modulator", Prepared for the American Psychiatric Association Annual Meeting, Available Online at: https://corcept.com/wp-content/uploads/2020/05/82545-APA-Poster-2020-04-13-final2.pdf, Apr. 25-29, 2020, 1 page.

Magee et al., "Construction of Cis- and Trans-Decahydroisoquinolines via Heterogeneous Catalytic Hydrogenation", The Journal of Organic Chemistry, American Chemical Society, vol. 64, No. 7, Mar. 16, 1999, pp. 2549-2554.

Mahmood et al., "3D-QSAR Comfa, Comsia Studies on Pyrazolo-Fused Azadecalins Derivatives as Selective Glucocorticoid Receptor Antagonists", Pharma Science Monitor, vol. 3, No. 3, Jul. 2012, pp. 2027-2055.

Melkersson et al., "Insulin and Leptin Levels in Patients With Schizophrenia or Related Psychoses—a Comparison Between Different Antipsychotic Agents", Psychopharmacology, vol. 154, No. 2, Mar. 1, 2001, pp. 205-212.

Nakawatase et al., "Alzheimer's Disease and Related Dementia", Cecil's Textbook of Medicine, Twenty-First Edition, vol. 1. W. B. Saunders Company, 2000, pp. 2042-2045.

Park , "Corcept Therapeutics Announces Third Quarter 2019 Financial Results and Provides Corporate Update", Exhibit 99.1, Available online at: https://ir.corcept.com/news-releases/news-release-details/corcept-therapeutics-announces-third-quarter-2019-financial, Nov. 7, 2019, 7 pages.

Park , "Corcept Therapeutics Announces Third Quarter 2019 Financial Results and Provides Corporate Update", Available Online at: https://ir.corcept.com/news-releases/news-release-details/corcept-therapeutics-announces-third-quarter-2019-financial, Nov. 7, 2019, pp. 1-10.

International Patent Application No. PCT/US2015/055487 , International Search Report and Written Opinion, Mailed on Feb. 12, 2016, 11 pages.

International Patent Application No. PCT/US2020/064520 , International Search Report and Written Opinion, Mailed on Apr. 8, 2021, 13 pages.

Rehn et al., "Antiinflammatory Action of Glucocorticoids—New Mechanisms for Old Drugs", The New England Journal of Medicine, vol. 353, No. 16, Oct. 20, 2005, pp. 1711-1723.

Rigalleau et al., "Diabetes as a Result of Atypical Anti-Psychotic Drugs—a Report of Three Cases", Diabetic Medicine, vol. 17, No. 6, Jun. 2000, pp. 484-486.

Sausville et al., "Contributions of Human Tumor Xenografts to Anticancer Drug Development", Cancer Research, vol. 66, No. 7, Apr. 2006, pp. 3351-3354.

Schultz et al., "Heteroatom Directed Photoarylation. Synthetic Potential of the Heteroatom Oxygen", Journal of the American Chemical Society, vol. 100, No. 7, Mar. 29, 1978, pp. 2150-2162.

Schultz et al., "Studies Directed at a Synthesis of the Morphine Alkaloids. A Photochemical Approach", The Journal of Organic Chemistry, vol. 50, No. 2, Jan. 1985, pp. 217-231.

Sindelar et al., "LLY-2707, A Novel Nonsteroidal Glucocorticoid Antagonist that Reduces Atypical Antipsychotic-Associated Weight Gain in Rats", Journal of Pharmacology and Experimental Therapeutics, vol. 348, No. 1, Jan. 1, 2014, pp. 192-201.

Spitz et al., "Mifepristone (RU 486)—A Modulator of Progestin and Glucocorticoid Action", The New England Journal of Medicine, Massachusetts Medical Society, vol. 329, No. 6, Aug. 5, 1993, pp. 404-412.

Temmerman et al., "Very Low Calorie Ketogenic Weight Reduction Diet in Patients with Cirrhosis: A Case Series", Nutrition & Diabetes, vol. 3, No. 11, Available online at: 10.1038/nutd.2013.36, Nov. 18, 2013, 3 pages.

Teutsch et al., "Design of Ligands for the Glucocortoid and Progestin Receptors", Biochemical Society Transactions, vol. 19, No. 4, Nov. 1991, pp. 901-908.

Uchida et al., "An Efficient Access to the Optically Active Manzamine Tetracyclic Ring System", Tetrahedron Letters, vol. 40, No. 1, Jan. 1, 1999, pp. 113-116.

"Goodman & Gilman's The Pharmacological Basis of Therapeutics", Eleventh Edition, 2006, pp. 14-22.

U.S. Appl. No. 17/736,912 , Advisory Action, Mailed on Dec. 27, 2022, 3 pages.

U.S. Appl. No. 17/736,912 , Final Office Action, Mailed on Sep. 1, 2023, 14 pages.

U.S. Appl. No. 17/736,912 , Final Office Action, Mailed on Oct. 21, 2022, 9 pages.

U.S. Appl. No. 17/736,912 , Non-Final Office Action, Mailed on May 31, 2023, 11 pages.

U.S. Appl. No. 17/736,912 , Non-Final Office Action, Mailed on Jul. 14, 2022, 7 pages.

Adams et al., "Nonalcoholic Fatty Liver Disease", Canadian Medical Association Journal, vol. 172, No. 7, Mar. 29, 2005, pp. 899-905.

Afdhal , "Fibroscan (Transient Elastography) for the Measurement of Liver Fibrosis", Gastroenterology & Hepatology, vol. 8, No. 9, Sep. 2012, pp. 605-607.

Albaugh et al., "Olanzapine Promotes Fat Accumulation in Male Rats by Decreasing Physical Activity, Repartitioning Energy and Increasing Adipose Tissue Lipogenesis while Impairing Lipolysis", Molecular Psychiatry, vol. 16, No. 5, May 2011, pp. 569-581.

Angulo et al., "Treatment of Non-Alcoholic Steatohepatitis", Best Practice & Research Clinical Gastroenterology, vol. 16, No. 5, Oct. 2002, pp. 797-810.

Anstee et al., "Mouse Models in Non-alcoholic Fatty Liver Disease and Steatohepatitis Research", International Journal of Experimental Pathology, vol. 87, No. 1, Feb. 2006, pp. 1-16.

Atucha et al., "A Mixed Glucocorticoid/mineralocorticoid Selective Modulator with Dominant Antagonism in the Male Rat Brain", Endocrinology, vol. 156, No. 11, Nov. 2015, pp. 1-10.

Bacon et al., "Nonalcoholic Steatohepatitis: An Expanded Clinical Entity", Gastroenterology, vol. 107, No. 4, Oct. 1994, pp. 1103-1109.

Belanoff et al., "Selective Glucocorticoid Receptor {Type II} Antagonists Prevent Weight Gain Caused by Olanzapine in Rats", European Journal of Pharmacology, vol. 655, No. 1-3, Mar. 25, 2011, pp. 117-120.

(56)            References Cited

OTHER PUBLICATIONS

Brunt et al., "Histopathology of Nonalcoholic Fatty Liver Disease", World Journal of Gastroenterology, vol. 16, No. 42, Nov. 14, 2010, pp. 5286-5296.

Bugianesi et al., "Non-Alcoholic Fatty Liver Disease/Non-Alcoholic Steatohepatitis (NAFLD/NASH): Treatment", Best Practice & Research Clinical Gastroenterology, vol. 18, No. 6, Dec. 2004, pp. 1105-1116.

Caprio et al., "Pivotal Role of The Mineralocorticoid Receptor in Corticosteroid-Induced Adipogenesis", The Faseb Journal, vol. 21, No. 9, Jul. 2007, pp. 2185-2194.

Caussy et al., "Noninvasive, Quantitative Assessment of Liver Fat by MRI-PDFF as an Endpoint in NASH Trials", Hepatology, vol. 68, No. 2, Aug. 2018, pp. 763-772.

Chalasani et al., "The Diagnosis and Management of Non-Alcoholic Fatty Liver Disease: Practice Guideline by the American Gastroenterological Association, American Association for the Study of Liver Diseases, and American College of Gastroenterology", Gastroenterology, vol. 142, No. 7, Jun. 2012, pp. 1592-1609.

Clark et al., "Nonalcoholic Fatty Liver Disease: An Under-recognized Cause of Cryptogenic Cirrhosis", JAMA, vol. 289, No. 22, Jun. 11, 2003, pp. 3000-3004.

Cooper et al., "Effects of Olanzapine in Male Rats: Enhanced Adiposity in the Absence of Hyperphagia, Weight Gain or Metabolic Abnormalities", Journal of Psychopharmacology, vol. 21, No. 4, Jun. 2007, pp. 405-413.

Fernø et al., "Olanzapine Depot Exposure in Male Rats: Dose-dependent Lipogenic Effects without Concomitant Weight Gain", European Neuropsychopharmacology, vol. 25, No. 6, Jun. 2015, pp. 923-932.

Goossens et al., "Translational Aspects of Diet and Non-Alcoholic Fatty Liver Disease", Nutrients, vol. 9, No. 1077, Sep. 28, 2017, pp. 1-9.

Gudowski et al., "Galectin-3 Concentration in Liver Diseases", Annals of Clinical & Laboratory Science, vol. 45, No. 6, 2015, pp. 669-973.

Hashimoto et al., "Mifepristone Promotes Adiponectin Production and Improves Insulin Sensitivity in a Mouse Model of Diet-Induced-Obesity", Public Library of Science One, vol. 8, No. 11, Nov. 2013, pp. 1-16.

Hebbard et al., "Animal Models of Nonalcoholic Fatty Liver Disease", Nature, vol. 8, Jan. 2011, pp. 34-44.

Henderson et al., "Glucose Metabolism in Patients with Schizophrenia Treated with Atypical Antipsychotic Agents", Archives of General Psychiatry, vol. 62, No. 1, Jan. 2005, pp. 19-28.

Hunt et al., "Discovery of a Novel Non-Steroidal GR Antagonist with in Vivo Efficacy in the Olanzapine-Induced Weight Gain Model in the Rat", Bioorganic & Medicinal Chemistry Letters, vol. 22, No. 24, Dec. 15, 2012, pp. 7376-7380.

Kleiner et al., "Design and Validation of a Histological Scoring System for Nonalcoholic Fatty Liver Disease", Hepatology, vol. 41, No. 6, Jun. 2005, pp. 1313-1321.

Koorneef et al., "Selective Glucocorticoid Receptor Modulation Prevents and Reverses Nonalcoholic Fatty Liver Disease in Male Mice", Endocrinology, vol. 159, No. 12, Dec. 1, 2018, pp. 3925-3936.

Larter et al., "Animal Models of NASH: Getting both Pathology and Metabolic Context Right", Journal of Gastroenterology and Hepatology, vol. 23, Nov. 2008, pp. 1635-1648.

Lau et al., "Animal Models of Non-Alcoholic Fatty Liver Disease", The Journal of Pathology, vol. 241, Nov. 22, 2016, pp. 36-44.

Lemke et al., "The Glucocorticoid Receptor Controls Hepatic Dyslipidemia Through Hes1", Cell Metabolism, vol. 8, No. 3, Sep. 3, 2008, pp. 212-223.

Lichtinghagen et al., "The Enhanced Liver Fibrosis (ELF) Score: Normal Value Influence Factors and Proposed Cut-off Values", EASL Journal of Hepatology, vol. 59, Mar. 2013, pp. 236-242.

Loomba et al., "Multicenter Validation of Association Between Decline in MRI-PDFF and Histologic Response in Non-Alcoholic Steatohepatitis", Hepatology, vol. 72, No. 4, Oct. 2020, pp. 1219-1229.

Merz et al., "Methodology to Assess Clinical Liver Safety Data", Drug Safety, 37 (Suppl 1), Nov. 2014, pp. S33-S45.

Minet-Ringuet et al., "Long Term Treatment with Olanzapine Mixed with the Food in Male Rats Induces Body Fat Deposition With no Increase in Body Weight and no Thermogenic Alteration", Appetite, vol. 46, No. 3, May 2006, pp. 254-262.

Patel et al., "Association of Noninvasive Quantitative Decline in Liver Fat Content on MRI with Histologic Response in Nonalcoholic Steatohepatitis", Therapeutic Advances in Gastroenterology, vol. 9, No. 5, Sep. 2016, pp. 692-701.

Application No. PCT/US2022/027442 , International Preliminary Report on Patentability, Mailed on Nov. 16, 2023, 9 pages.

Application No. PCT/US2022/027442 , International Search Report and Written Opinion, Mailed on Aug. 24, 2022, 15 pages.

Petaja et al., "Definitions of Normal Liver Fat and the Association of Insulin Sensitivity with Acquired and Genetic NAFLD—A Systematic Review", International Journal of Molecular Sciences, vol. 17, No. 5, Apr. 27, 2016, pp. 1-16.

Ray et al., "Discovery and Optimization of Novel, Non-Steroidal Glucocorticoid Receptor Modulators", Bioorganic & Medicinal Chemistry Letters, vol. 17, No. 17, Sep. 1, 2007, pp. 4901-4905.

Soliman et al., "Histological Evaluation of the Role of Atypical Antipsychotic Drugs in Inducing Non-Alcoholic Fatty Liver Disease in Adult Male Albino Rats (Light and Electron Microscopic Study)", Folia Biologica, vol. 59, No. 5, Nov. 2013, pp. 173-180.

Takahashi et al., "Animal Models of Nonalcoholic Fatty Liver Disease/Nonalcoholic Steatohepatitis", World Journal of Gastroenterology, vol. 18, No. 19, May 21, 2012, pp. 2300-2308.

Tolbol et al., "Metabolic and Hepatic Effects of Liraglutide, Obeticholic Acid and Elafibranor in Diet-induced Obese Mouse Models of Biopsy-confirmed Nonalcoholic Steatohepatitis", World Journal of Gastroenterology, vol. 24, No. 2, Jan. 14, 2018, pp. 179-194.

Van Der Zwaal et al., "Modelling Olanzapine-induced Weight Gain in Rats", The International Journal of Neuropsychopharmacology, vol. 17, No. 1, Jan. 2014, pp. 169-186.

Van Herck et al., "Animal Models of Nonalcoholic Fatty Liver Disease—A Starter's Guide", Nutrients, vol. 9, No. 1072, Sep. 27, 2017, pp. 1-13.

Vilar-Gomez et al., "Non-Invasive Assessment of Non-alcoholic Fatty Liver Disease: Clinical Prediction Rules and Blood-based Biomarkers", Journal of Hepatology, vol. 68, No. 2, Feb. 2018, pp. 305-315.

Wada et al., "Spironolactone Improves Glucose and Lipid Metabolism by Ameliorating Hepatic Steatosis and Inflammation and Suppressing Enhanced Gluconeogenesis Induced by High-Fat and High-Fructose Diet", Endocrinology, vol. 151, No. 5, May 2010, pp. 2040-2049.

Yeh et al., "Pathology of Nonalcoholic Fatty Liver Disease", American Journal of Clinical Pathology, vol. 128, No. 5, Nov. 2007, pp. 837-847.

U.S. Appl. No. 18/386,828, filed Nov. 3, 2023, 69 pages.

Liu et al., "The Role of Hepatic Fat Accumulation in Pathogenesis of Non-alcoholic Fatty Liver Disease (NAFLD)", Lipids in Health and Disease 2010, Available Online at: https://lipidworld.biomedcentral.com/articles/10.1186/1476-511X-9-42, Apr. 28, 2010, pp. 1-9.

U.S. Appl. No. 18/386,828 , "Final Office Action", filed May 2, 2024, 15 pages.

Tremblay et al., "Circulating Galectin-3 Levels are not Associated With Nonalcoholic Fatty Liver Disease: a Mendelian Randomization Study", The Journal of Clinical Endocrinology & Metabolism, vol. 106, Issue 8,, Mar. 8, 2021, pp. e3178-e3184.

Time Course of Aminotransferase Levels and LFC

(in patients with post-baseline MRI)

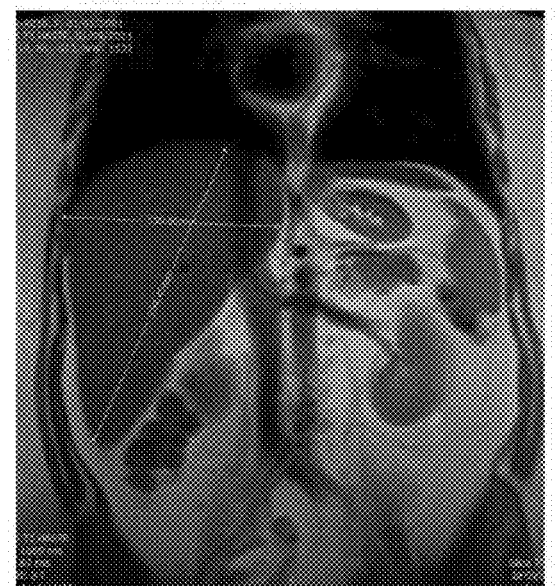
Before treatment
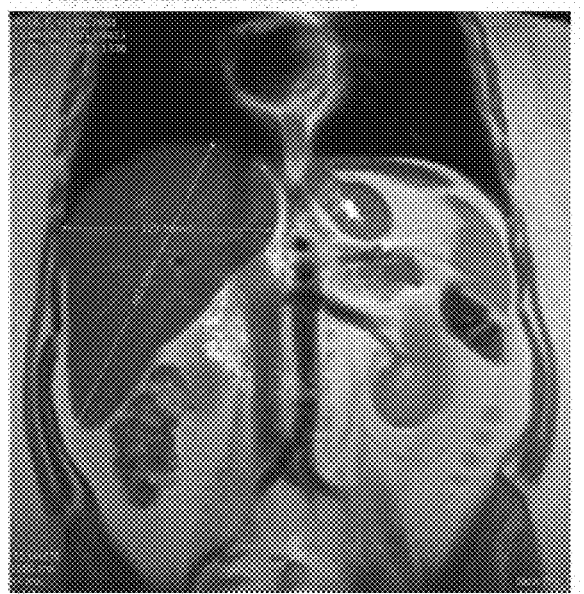
Post treatment with Miricorilant
FIG. 3B

AE Action taken with Study Treatment

▲ No Action ● Drug Withdrawn/Interrupted

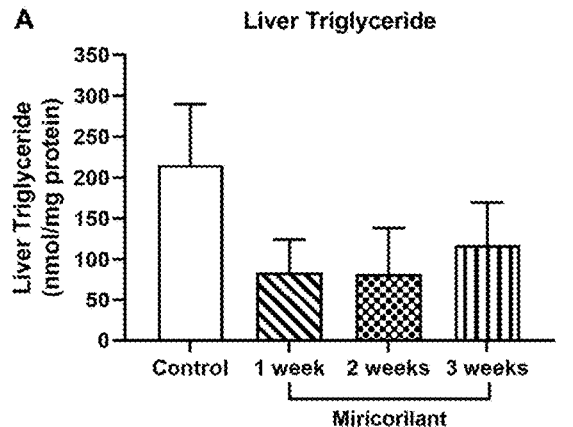
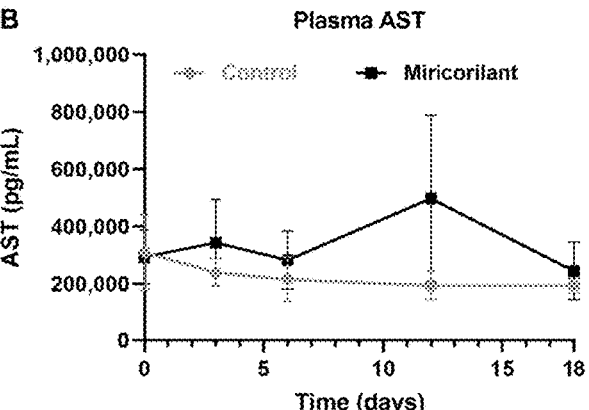
FIG. 6A                    FIG. 6B

NAFLD Activity Score – Ballooning degeneration

LIVER WEIGHT

LIVER TYPE 1 COLLAGEN (col1a1)

LIVER GALECTIN-3 CONTENT

Understanding Transaminase Elevations: Responder Analysis Summary

MRI-PDFF % Change from Baseline and ALT/ULN Linear Regression Lines from Baseline to Week 6 by Responder Status

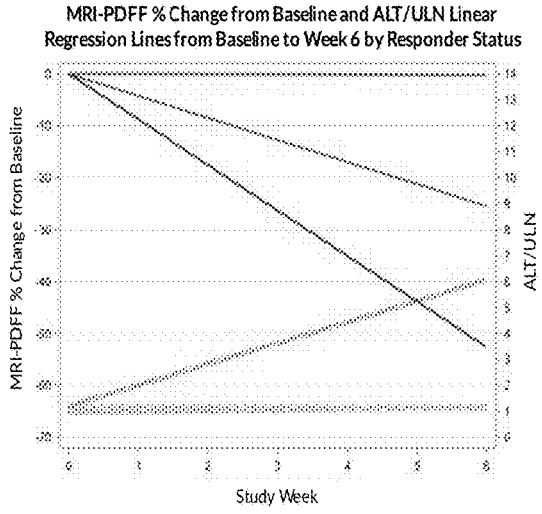

Study Week

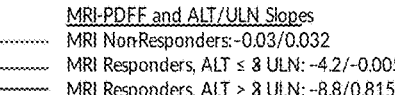

MRI-PDFF and ALT/ULN Slopes
.......... MRI Non-Responders: -0.03/0.032
_____ MRI Responders, ALT ≤ 3 ULN: -4.2/-0.005
_____ MRI Responders, ALT > 3 ULN: -8.8/0.815

- Treatment responders with ALT >3 × ULN had a faster decline in LFC loss, mean reduction in LFC of -52.6% at Week 6
  - Responders with ALT >3 × ULN slope -8.76, responders without ALT >3 × ULN slope -4.24
  - Patients with a more gradual weekly rate of LFC loss were less likely to experience a corresponding rise in ALT Responders: Patients who had ≥30% reduction in LFC from baseline at any time
ALT, alanine aminotransferase; LFC, liver fat content; MRFF, magnetic resonance imaging proton density fat fraction; ULN, per limit of normal.

FIG. 10

Reduction in LFC Is Unrelated to Change in Weight
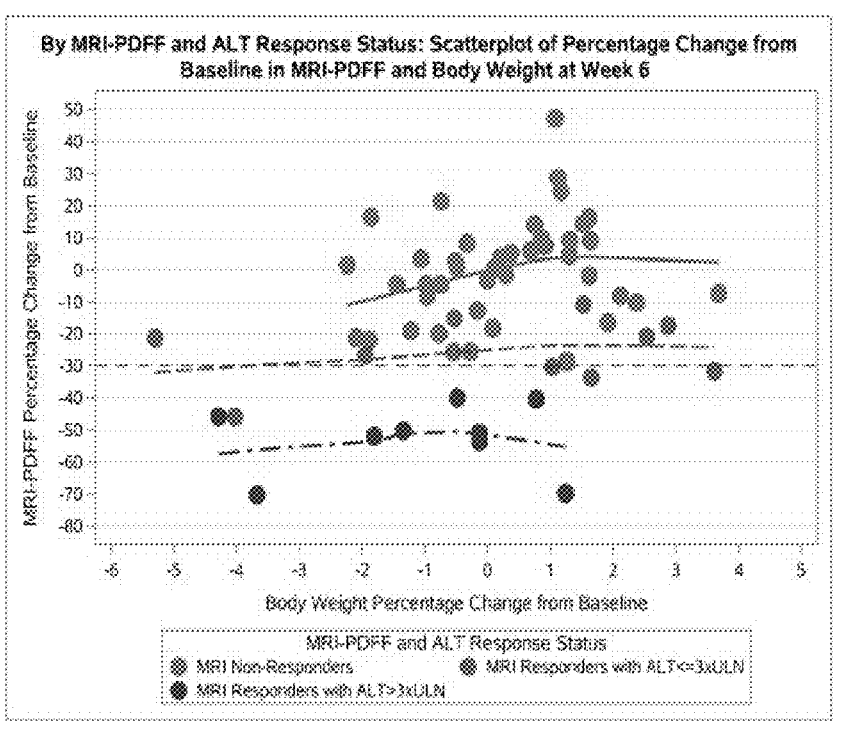
FIG. 11

Patients With Drug Held Due to ALT or AST Elevation and Restarted Drug at Same Dose

| Cohort | Baseline ALT (U/L) | Peak ALT (U/L) | End of Treatment ALT (U/L) | Weeks off Miricorilant | Weeks on Miricorilant After Rechallenge | Maximum % LFC Reduction |
|---|---|---|---|---|---|---|
| 1 (150 mg daily) | 18 | 190 (U1, Wk 5) | 15 (Wk 24) | 7 Wks | 11 Wks | -40.4% |
| 1 (150 mg daily) | 30 | 142 (Wk 6) | 18 (Wk 24) | 4 Wks | 13 Wks | -45.9% |
| 2 (150 mg daily) | 49 | 95 (Wk 4) | 67 (Wk 12) | 3 Wks | 4 Wks | -22.9% |

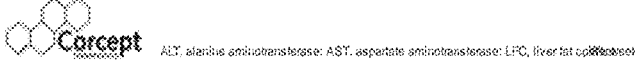

ALT, alanine aminotransferase; AST, aspartate aminotransferase; LFC, liver fat content.

FIG. 12

Patient 2 (Cohort1: 150 mg Daily x 24 Weeks)

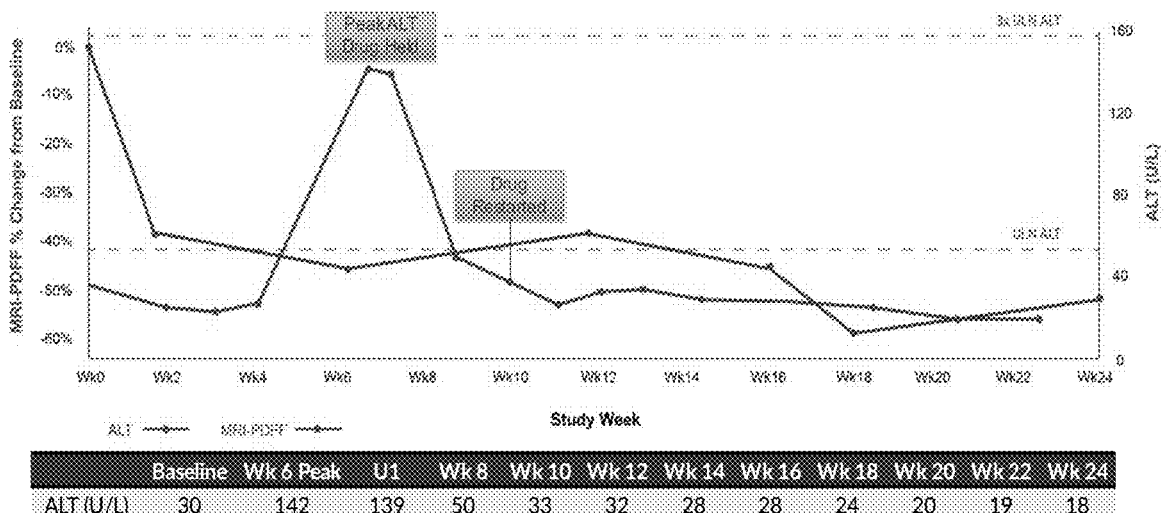

| | Baseline | Wk 6 Peak | U1 | Wk 8 | Wk 10 | Wk 12 | Wk 14 | Wk 16 | Wk 18 | Wk 20 | Wk 22 | Wk 24 |
|---|---|---|---|---|---|---|---|---|---|---|---|---|
| ALT (U/L) | 30 | 142 | 139 | 50 | 33 | 32 | 28 | 28 | 24 | 20 | 19 | 18 |
| AST (U/L) | 27 | 89 | 82 | 32 | 32 | 28 | 24 | 26 | 24 | 20 | 19 | 18 |

- Total bilirubin, direct bilirubin, ALP, INR within normal limits. GGT elevated at baseline (peak 88 U/Lat Wk 10); other weeks below baseline
- Eosinophils (%) baseline 7.3, decreased to 2.2at Wk 2 and increased Wk 3 (peak 4.3), decreased Wk 8 (2.0) and stableuntil EOT
- Pharmacokinetics: $C_{max}$ 404 ng/mL, AUC 5897.19 h*ng/mL Corcept  ALP, alkaline phosphatase; ALT, alanine aminotransferase; AST, aspartate aminotransferase; AUC, area under the concentration-time curve; $C_{max}$, maximum concentration; EOT, end of treatment; GGT, gammaglutamyltransferase; INR, international normalized ratio; MRIPDFF, magnetic resonance imaging proton density fraction; ULN, upper limit of normal; Wk, week.

FIG. 13

Cohort 6 (100 mg QMF)Had the Best Benefit-Risk Profile

- At week 12, mean relative reduction in LFC was −28.2% (SD, 13.5),with a corresponding decline in liver enzymes
- Patients in this cohort overall had improved lipid profiles, glycemic markers, and fibrosis biomarkers

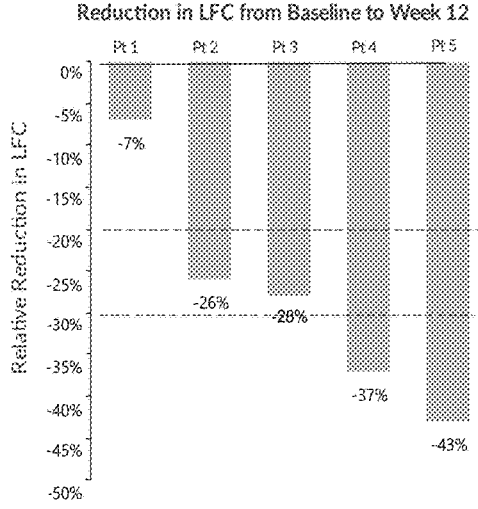

*Data shown for those 5 patients in cohort 6 who received ≥1 dose of study drug, remained on trial for ≥8 weeks, and had MRI-PDFF assessment. One patient discontinued at week 8 (lost to followup) and is not included.
LFC, liver fat content; MRI-PDFF, magnetic resonance imaging proton density fat fraction. pt, patient.

FIG. 14

Cohort 6 (100 mg QMF) Week 12 Results: Efficacy and Safety

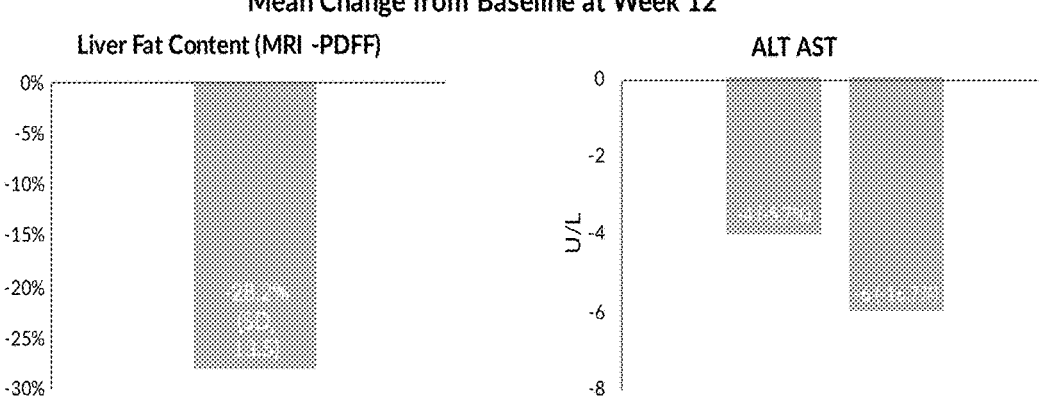

Mean Change from Baseline at Week 12

By Week 12, miricorilant 100 mg twice weekly reduced LFCby ~30% from baseline and lowered mean ALT and AST
→ 100 mg QMF weeklyis a promising dosage regimen for phase 2

ALT, alanine aminotransferase; AST, aspartate aminotransferase; LFC, liver fat content; MRIDFF, magnetic resonance imaging proton density fat fraction; QMF, every Monday and Friday; SD, standard deviation.

FIG. 15

Cohort 6 (100 mg QMF) Week 12 Results: Lipids
Mean Change from Baseline at Week 12
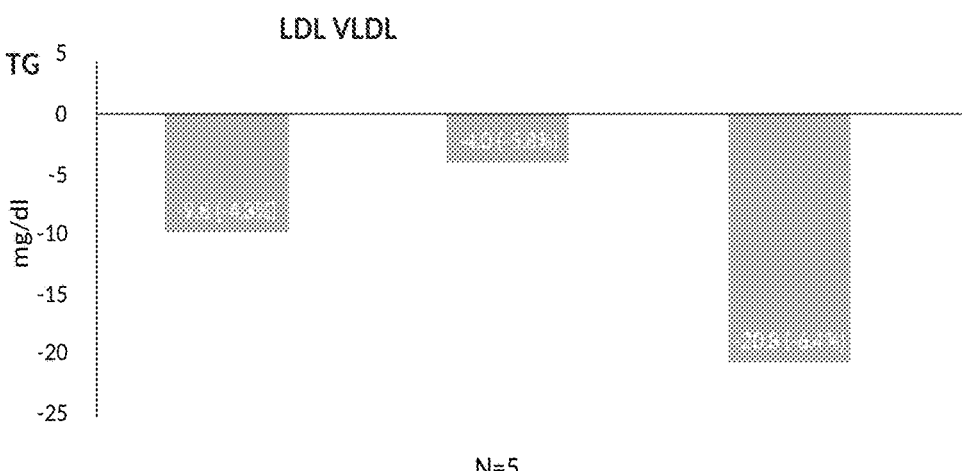
N=5
Patients in this cohort overall had improved lipid profiles
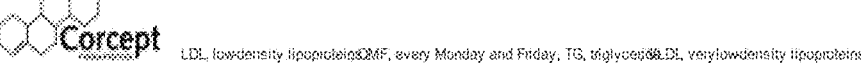
FIG. 16

Cohort 6 (100 mg QMF) Week 12 Results: Glycemic Markers
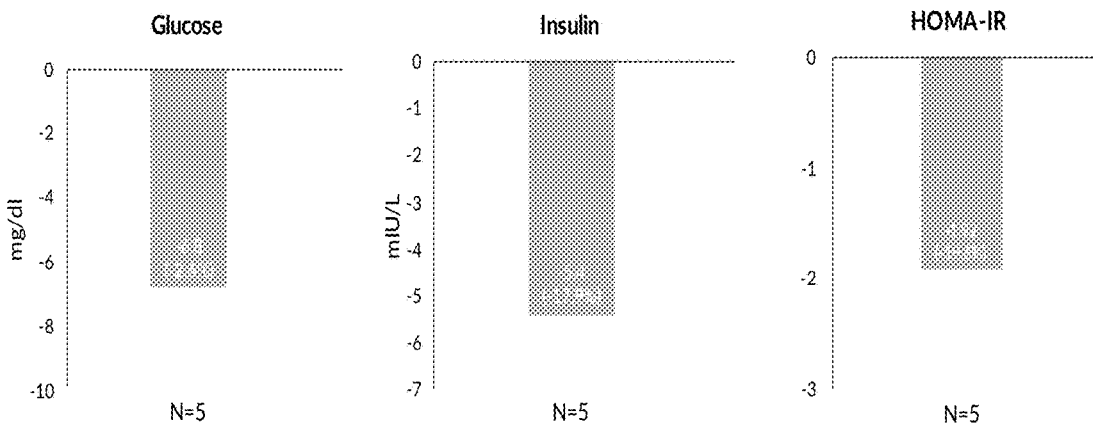
Mean Change from Baseline at Week 12
Patients in this cohort overall had improved glycemic markers
HOMA-IR, homeostatic model assessment of insulin resistance, every Monday and Friday
FIG. 17

Cohort 6 (100 mg QMF) Week 12 Results: Fibrosis Markers
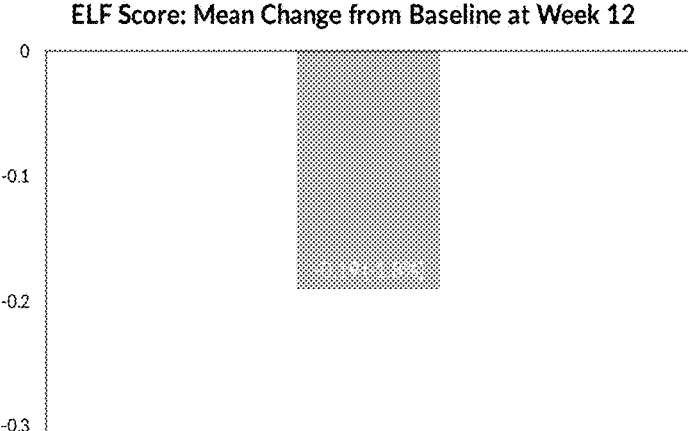
ELF Score: Mean Change from Baseline at Week 12
N=4
Patients in this cohort overall had reduction in fibrosis biomarker
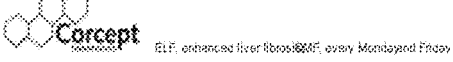
ELF, enhanced liver fibrosis; QMF, every Monday and Friday
FIG. 18

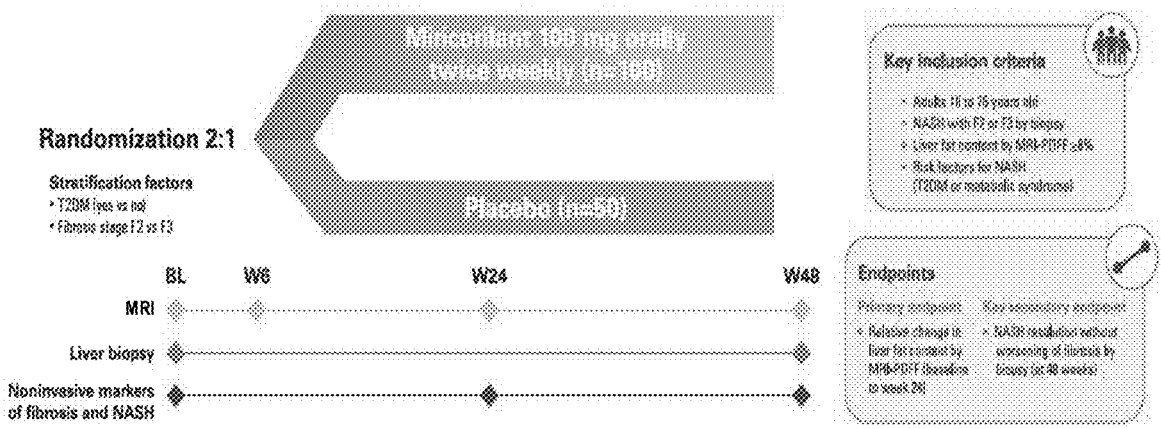
FIG. 19

METHODS FOR REDUCING LIVER FAT AND FOR TREATING FATTY LIVER DISORDERS

CROSS-REFERENCE TO RELATED APPLICATIONS

This application is a continuation-in-part of, and claims priority to and the benefit of, U.S. patent application Ser. No. 17/736,912, filed May 4, 2022, and claims priority to, and the benefit of, U.S. Provisional Application No. 63/184,694, filed May 5, 2021; U.S. Provisional Application No. 63/244, 116, filed Sep. 14, 2021; and U.S. Provisional Application No. 63/271,861, filed Oct. 26, 2021, all of which applications are hereby incorporated by reference herein in their entireties.

BACKGROUND

Liver diseases are a significant cause of disease and death in the United States and abroad. Excessive liver fat, as compared to normal levels of liver fat, are indicative of, and may be a cause of, fatty liver diseases. However, although the incidence of liver diseases is increasing, treatments for these disorders are lacking. For example, non-alcoholic fatty liver disease (NAFLD) affects about 20% of people worldwide; however, there are no approved pharmacologic treatments for NAFLD.

Liver disorders can be categorized in different groups of diseases, such as alcohol-induced (or alcohol-related) fatty liver disease (AFLD), nonalcoholic fatty liver disease (NAFLD; including, e.g., non-alcoholic steatohepatitis (NASH)), drug- or alcohol-related liver diseases, viral diseases, immune-mediated liver diseases, metabolic liver diseases, and complications associated with hepatic insufficiency and/or liver transplantation. Nonalcoholic fatty liver disease is a common hepatic disorder with histological features similar to those of alcohol-induced fatty liver disease, in individuals who consume little or no alcohol. Normal levels of liver fat are discussed in Pataja et al., Int. J. Mol. Sci. 2016, 17, 633 (e.g., about 5% by histological measurements, or by weight). Fatty liver disease is believed to be due to an abnormal retention of lipid (fats) within hepatocytes. High levels of liver fat, and fatty liver disease, may lead to liver fibrosis or cirrhosis of the liver. Normal levels of alanine aminotransferase (ALT) are known and ascertainable; upper limit of normal (ULN) for serum ALT level for healthy adults (per AASLD guideline) are 35 U/L for males and 25 U/L for females. Normal levels of aspartate aminotransferase (AST) are known and ascertainable; ULN for serum AST level for healthy adults are 20 U/L for males and 36 U/L for females.

Reductions in liver fat have been reported following long-term (e.g., 24 weeks) experimental treatment (for review, see Loomba et al., Hepatology 2020 October; 72(4): 1219-1229). A decline in liver fat of about 30% or more is believed to be clinically meaningful, and may be associated with clinical benefit including reduction of steatosis grade, histological improvement, and improvement in inflammation (Caussy et al., Hepatology. 2018 August; 68(2): 763-772).

Treatments for fatty liver diseases are discussed, for example, in U.S. Pat. No. 10,238,659 and in U.S. Pat. No. 10,881,660. However, there remain need for additional methods for treating liver disorders related to high levels liver fat, and for managing fatty liver disease. Surprisingly, the present invention meets these and other needs.

SUMMARY

Applicant discloses herein rapid and extensive reduction in liver fat with a short duration of oral administration of a non-steroidal glucocorticoid receptor modulator (GRM). Reductions of liver fat ranged from 38.5% to 73.8% (as measured by magnetic resonance imaging-proton density fat fraction (MRI-PDFF)) in 4 of 5 patients receiving the GRM miricorilant; the duration of daily miricorilant administration for these patients ranged from between 30 to 44 days; liver fat percentage was measured between 16 and 64 days following cessation of miricorilant administration. A further effect of miricorilant was an increase in liver enzymes alanine amino transferase (ALT) and aspartate amino transferase (AST).

Applicant discloses herein methods, uses, and compositions for reducing the level of fat in the liver of a patient, including methods for reducing high or excessive levels of liver fat, as compared to normal levels of liver fat, for treatment of patients in need thereof. Applicant discloses herein methods, uses, and compositions for reducing liver degeneration, or liver weight, or liver collagen, or liver galectin, or liver fibrosis, as compared to normal levels, or as compared to baseline values, for treatment of patients in need thereof. Reducing fat levels, including reducing the amount of liver fat, and reducing the relative amounts of fat in the liver of a patient as compared to other liver components, is useful for treating fatty liver diseases. Reducing liver degeneration, reducing liver weight, reducing liver collagen, reducing liver galectin, or reducing liver fibrosis is believed to be useful for treating fatty liver diseases. Fatty liver diseases which may be treated with the methods and compositions disclosed herein include, without limitation, non-alcoholic fatty liver disease (NAFLD) and nonalcoholic steatohepatitis (NASH), which can lead to nonalcoholic cirrhosis, as well as alcohol related fatty liver disease (ARLD) (alcohol fatty liver disease (AFL), alcoholic steatohepatitis (ASH), and as a possible consequence alcoholic cirrhosis. Such fatty liver diseases may include, or lead to, liver fibrosis. Large reductions of fat over a period of time (e.g., about 12 weeks to 52 weeks) can result in a reduction in liver fibrosis.

The methods, uses and compositions disclosed herein comprise administering to the patient an effective amount of a non-steroidal GRM. In embodiments, the GRM is a cyclohexyl pyrimidine GRM compound, as described and disclosed in U.S. Pat. Nos. 8,685,97 and in 9,321,736. Methods, compositions, and uses related to those disclosed herein are described in U.S. Provisional Patent Application No. 63/184,694, filed May 5, 2021, and U.S. Provisional Patent Application No. 63/244,116, filed Sep. 14, 2021, both entitled Methods for Reducing Liver Fat and for Treating Fatty Liver Disorders, with inventors, Ada Lee, Andreas Grauer, and Joseph Belanoff. All patents, patent publications, and patent applications cited herein, both supra and infra, are hereby incorporated by reference in their entireties.

In embodiments, the GRM is the cyclohexyl pyrimidine GRM compound (E)-6-(4-Phenylcyclohexyl)-5-(3-trifluoromethylbenzyl)-1H-pyrimidine-2,4-dione ("miricorilant"; also known as "CORT118335"), which has the structure:

In embodiments, the miricorilant is orally administered. In embodiments, the miricorilant is administered with food. In embodiments, the miricorilant is administered without food. In embodiments, the miricorilant is administered without food to a fasted patient.

The present results show that miricorilant administration is effective to reduce liver fat in human patients presumed to have NASH. Such reduction may be rapid. Surprisingly, liver fat levels were reduced with only a few weeks of miricorilant treatment (liver fat levels normalized with 30 or 34 days of treatment in two of five patients administered miricorilant). The extent and rapidity of reduction in liver fat in these patients was surprising and unexpected in view of the literature, and in view of the fact that such rapid reductions were not seen in previous studies in human volunteers not having evidence of NASH. The rapid reduction in liver fat seen in patients presumed to have NASH may be related to the increase in ALT and AST seen in these patients, which have not been seen at similar dose levels with miricorilant administration to normal human volunteers.

The present methods provide improved methods of reducing the level of fat in the liver of a patient in need of such reduction, of treating fatty liver diseases, including NAFLD, NASH, ARLD, ASH, and other fatty liver diseases, of slowing or preventing the progression of fatty liver to liver cirrhosis, of slowing or preventing the progression of fatty liver to liver fibrosis, and treating other liver disorders.

BRIEF DESCRIPTION OF THE DRAWINGS

FIG. 3B presents a magnetic resonance imaging (MRI) scan showing the liver of the same patient shown in 3A, which demonstrates a decrease in liver size in the patient following miricorilant treatment.

FIG. 6A presents the results of experiments in which male C57 mice were fed on a high-fat diet with, and without daily doses of miricorilant. In mice on a high-fat diet, daily dosing of miricorilant led to a rapid reduction in liver triglycerides starting at week 1.

FIG. 6B presents further results of experiments in which male C57 mice were fed on a high-fat diet with, and without daily doses of miricorilant. AST showed a transient increase at 2 weeks but normalized by 3 weeks without a change in miricorilant dose.

As illustrated in FIG. 9, patients in the study will receive: 150 milligrams (mg) per day of miricorilant each day for 24 weeks or for 12 weeks; or will receive 100 mg per day of miricorilant three times per week, or two times per week; or daily for two weeks, followed by miricorilant administered three times per week, or two times per week. Times in which sample collection and MRI-PDFF are scheduled to be performed are also indicated.

FIG. 10 provides a graph showing MRI-PDFF (a measure of liver fibrosis) and liver enzyme levels as a function of time during miricorilant treatment, for three groups of patients: patients who did not appear to respond to miricorilant treatment (non-responders); patients who did respond to miricorilant treatment, and did not have increased liver enzyme levels that exceeded 3 times normal liver enzyme levels; and patients who did respond to miricorilant treatment, and whose liver enzyme levels increased to greater than 3 times normal liver enzyme levels.

FIG. 11 provides a scatterplot of patient body weight as a function of MRI-PDFF percentage change from baseline.

FIG. 12 provides a table showing liver fat content for patients receiving miricorilant treatment whose miricorilant treatments were stopped for a period of time (7 weeks, 4 weeks, and 3 weeks), and then resumed.

FIG. 13 provides a plot of MRI-PDFF (top line at week 0) and liver enzyme alanine aminotransferase (ALT; bottom line at week 0) for a patient who received miricorilant treatment that included a cessation of miricorilant treatment from week 7 to week 10.

FIG. 14 provides a bar graph illustrating the reductions in liver fat content (LFC) over the course of twelve weeks of miricorilant treatment in patients receiving 100 mg of miricorilant twice per week (on Mondays and on Fridays).

FIG. 15 provides bar graphs illustrating the reductions in liver fat content (LFC) as measured by MRI-PDFF and in liver enzyme levels (alanine aminotransferase (ALT) and aspartase aminotransferase (AST)) over the course of twelve weeks of miricorilant treatment in patients receiving 100 mg of miricorilant twice per week (on Mondays and on Fridays).

FIG. 16 provides a bar graph illustrating reductions in lipid levels (low density lipoprotein (LDL) and very low density lipoprotein (VLDL)) in patients receiving 100 mg of miricorilant twice per week (on Mondays and on Fridays).

FIG. 17 provides bar graphs illustrating reductions in glycemic markers in patients receiving 100 mg of miricorilant twice per week (on Mondays and on Fridays). HOMA-IR is an acronym for Homeostatic Model Assessment of Insulin Resistance.

FIG. 18 provides a bar graph illustrating reductions in fibrosis markers in patients receiving 100 mg of miricorilant twice per week (on Mondays and on Fridays).

FIG. 19 illustrates a clinical trial study plan for evaluating the effects of administration of 100 mg of miricorilant twice per week (on Mondays and on Fridays), as compared to placebo, in patients suffering from noncirrhotic NASH.

DETAILED DESCRIPTION

A. Introduction

Figure 1:
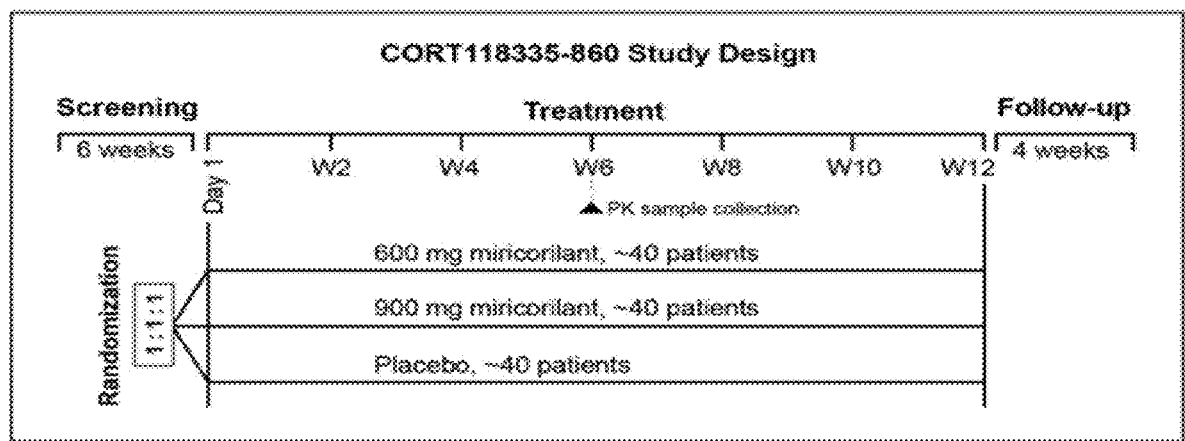
FIG. 1 provides a graphic illustration of the design of the full study, some results of which are presented herein. Blood samples for the measurement of miricorilant plasma concentrations were collected at the Week 6 visit.

The methods disclosed herein can be used to reduce liver fat in a patient in need of reducing liver fat. The methods disclosed herein can be used to reduce liver degeneration in a patient in need of reducing liver degeneration. The methods disclosed herein can be used to reduce liver weight in a patient in need of reducing liver weight. The methods disclosed herein can be used to reduce liver collagen in a patient in need of reducing liver collagen. The methods disclosed herein can be used to reduce liver galectin in a patient in need of reducing liver galectin. Reducing liver fat, or liver degeneration, or liver weight, or liver collagen, or liver galectin, is believed to be useful in treating patients suffering from a fatty liver disease, such as, e.g., non-alcoholic fatty liver disease (NAFLD) and nonalcoholic steatohepatitis (NASH), which can lead to nonalcoholic cirrhosis, as well as alcohol related fatty liver disease (ARLD) (alcohol fatty liver disease (AFL), alcoholic steatohepatitis (ASH), and as a possible consequence alcoholic cirrhosis; may aid in treating liver fibrosis; and may aid in treating other liver diseases characterized by, or exacerbated by, high levels of liver fat as compared to normal levels of liver fat (normal levels of liver fat are typically less than about 5%).

Treatments for fatty liver diseases are discussed in U.S. Pat. No. 10,238,659, filed Oct. 14, 2015 and in U.S. Pat. No. 10,881,660, filed Jan. 24, 2019, the entire contents of which are hereby incorporated by reference in their entireties.

In embodiments, Applicant discloses herein methods of reducing liver fat in a patient in need thereof, comprising administering to the patient an effective amount of the nonsteroidal glucocorticoid receptor modulator (GRM) (E)-

6-(4-Phenylcyclohexyl)-5-(3-trifluoromethylbenzyl)-1H-pyrimidine-2,4-dione ("miricorilant"), which has the structure:

effective to reduce the amount of liver fat in the patient. In embodiments, Applicant discloses herein methods of reducing liver degeneration, or liver weight, or liver collagen, or liver galectin, or liver fibrosis, in a patient in need thereof, comprising administering to the patient an effective amount of the nonsteroidal glucocorticoid receptor modulator miricorilant. In embodiments of the methods of reducing liver fat, or liver degeneration, or liver weight, or liver collagen, or liver galectin, or liver fibrosis, the patient suffers from a non-alcoholic fatty liver disease (NAFLD). In further embodiments, the patient suffers from an alcohol related fatty liver disease (ARLD). In embodiments of the methods, miricorilant is administered orally. In embodiments of the methods, miricorilant is administered with food. In other embodiments of the methods, miricorilant is administered without food. In embodiments of the methods wherein miricorilant is administered without food, miricorilant is administered to a fasted patient without food.

In embodiments, Applicant discloses methods of treating a liver disease in a patient in need thereof, comprising administering to the patient an effective amount of the nonsteroidal glucocorticoid receptor modulator (GRM) (E)-6-(4-Phenylcyclohexyl)-5-(3-trifluoromethylbenzyl)-1H-pyrimidine-2,4-dione ("miricorilant"), effective to reduce the amount of liver fat in the patient. In embodiments of the methods of treating a liver disease, the liver disease is characterized by abnormally high levels of liver fat. In embodiments, the liver disease characterized by abnormally high levels of liver fat is further characterized by abnormal or excessive levels of one or more of liver degeneration, liver weight, liver collagen, and liver galectin, and the method of treating the disease is effective to normalize or reduce the abnormal or excessive levels of liver degeneration, liver weight, liver collagen, or liver galectin. In embodiments of the methods of treating a liver disease disclosed herein, the liver disease is a non-alcoholic fatty liver disease (NAFLD). In embodiments of the methods of treating a liver disease disclosed herein, the liver disease is an alcohol related fatty liver disease (ARLD). In embodiments of the methods, miricorilant is administered orally. In embodiments of the methods, miricorilant is administered with food. In other embodiments of the methods, miricorilant is administered without food. In embodiments of the methods wherein miricorilant is administered without food, miricorilant is administered to a fasted patient without food.

In embodiments, Applicant discloses herein a pharmaceutical composition for reducing liver fat in a patient, the pharmaceutical composition comprising the nonsteroidal glucocorticoid receptor modulator (GRM) (E)-6-(4-Phenylcyclohexyl)-5-(3-trifluoromethylbenzyl)-1H-pyrimidine-2,4-dione ("miricorilant") and a pharmaceutically acceptable excipient.

In embodiments, Applicant discloses herein a pharmaceutical composition for treating a liver disease characterized by abnormally high levels of liver fat in a patient, the pharmaceutical composition comprising the nonsteroidal glucocorticoid receptor modulator (GRM) (E)-6-(4-Phenylcyclohexyl)-5-(3-trifluoromethylbenzyl)-1H-pyrimidine-2,4-dione ("miricorilant") and a pharmaceutically acceptable excipient.

In embodiments, Applicant discloses herein the use of the nonsteroidal glucocorticoid receptor modulator (GRM) (E)-6-(4-Phenylcyclohexyl)-5-(3-trifluoromethylbenzyl)-1H-pyrimidine-2,4-dione ("miricorilant") for reducing liver fat in a patient.

In embodiments, Applicant discloses herein the use of the nonsteroidal glucocorticoid receptor modulator (GRM) (E)-6-(4-Phenylcyclohexyl)-5-(3-trifluoromethylbenzyl)-1H-pyrimidine-2,4-dione ("miricorilant") for treating a liver disease characterized by abnormally high levels of liver fat in a patient. In embodiments, the liver disease characterized by abnormally high levels of liver fat is further characterized by abnormal or excessive levels of one or more of liver degeneration, liver weight, liver collagen, and liver galectin, and the use of miricorilant in treating the disease is effective to normalize or reduce the abnormal or excessive levels of liver degeneration, liver weight, liver collagen, or liver galectin.

In embodiments, the effective amount of miricorilant is a daily dose of between 1 and 100 milligrams per kilogram per day (mg/kg/day). In some embodiments, the daily dose of miricorilant is 1, 2, 4, 6, 8, 10, 12, 14, 16, 18, 20, 30, 40, 50 60, 70, 80, 90 or 100 mg/kg/day. In embodiments, the daily dose of miricorilant is 10, 20, 25, 50, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1150, 1200, 1250, 1300, 1400, and 1500 milligrams per day (mg/day). In some cases, miricorilant is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks. In embodiments, the GRM is administered with food. In embodiments, the GRM is administered without food. In embodiments, the GRM is administered without food to a fasted patient. In embodiments, the GRM may be administered with at least one other therapeutic agent.

The search for medical treatments for reducing liver fat, and for treating fatty liver disease, and treating liver fibrosis, has been difficult, and lacking in success. In view of the failure in the art to provide medical treatments useful for reducing liver fat in patients in need thereof, and in view of the failure in the art to provide medical treatments useful for treating fatty liver diseases, and for treating liver fibrosis, the results disclosed herein, and the methods, compositions, and uses disclosed herein are surprising and unexpected, and provide advantages over the art.

B. Definitions

Abbreviations used herein include: ACTH, adrenocorticotropic hormone; AE, adverse events; ALT, alanine aminotransferase; AST, aspartate aminotransferase; AUDIT, Alcohol Use Disorders Identification Test; BP, blood pressure; DBP, diastolic blood pressure; DILI, drug-induced liver injury; ECG, electrocardiogram; ELF score, enhanced liver fibrosis score (composed of hyaluronic acid, tissue inhibitor of metalloproteinases-1 [TIMP-1], and type III procollagen [PIIINP]); ET, early termination; FSH, follicle-stimulating hormone; GGT, gamma-glutamyl transferase; HbA1c, glycated hemoglobin; HBV, hepatitis B virus; HCV, hepatitis C virus; HIV, human immunodeficiency virus; GR, glucocorticoid receptor; HOMA-IR, Homeostatic Model Assessment of Insulin Resistance; INR, international normalized ratio; MR, mineralocorticoid receptor; MRI-PDFF, magnetic resonance imaging-proton density fat fraction; NASH, nonalcoholic steatohepatitis; PIIINP, type III procollagen; PK, pharmacokinetics; pro-C3, propeptide of type III collagen; SBP, systolic blood pressure; TIMP-1, tissue inhibitor of metalloproteinases-1; ULN, upper limit of normal; W, week; WBC, white blood cell count.

The terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

As used herein, "patient" or "subject" refers to a living organism suffering from or prone to a condition that can be treated by administration of a compound or pharmaceutical composition as provided herein. Non-limiting examples include humans, other mammals and other non-mammalian animals. For example, the term "patient" may refer to a human that is or will be receiving, or has received, medical care for a disease or condition, or prophylactic treatment to prevent or reduce the severity of a disease or condition that the patient is at risk of suffering.

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

"Pharmaceutically-acceptable excipient" and "pharmaceutically-acceptable carrier" refer to a substance that aids the administration of an active agent to—and absorption by—a patient and can be included in the compositions of the present invention without causing a significant adverse toxicological effect on the patient. As used herein, these terms are intended to include any and all solvents, dispersion media, coatings, antibacterial and antifungal agents, antioxidant agents, isotonic and absorption delaying agents, and the like, compatible with pharmaceutical administration. Non-limiting examples of pharmaceutically-acceptable excipients include water, NaCl, normal saline solutions, lactated Ringer's, normal sucrose, normal glucose, binders, fillers, disintegrants, encapsulating agents, plasticizers, lubricants, coatings, sweeteners, flavors and colors, and the like. One of ordinary skill in the art will recognize that other pharmaceutical excipients are useful in the present invention. The use of such media and agents for pharmaceutically active substances is well known in the art. Except insofar as any conventional media or agent is incompatible with the active compound, use thereof in the compositions is contemplated. Supplementary active compounds can also be incorporated into the compositions. One of ordinary skill in the art will recognize that other pharmaceutical excipients are useful in the present invention.

As used herein, the terms "administer," "administering," "administered" or "administration" refer to providing a compound or a composition (e.g., one described herein), to a subject or patient. For example, a compound or composition may be administered orally to a patient.

As used herein, the terms "effective amount", "therapeutic amount", and "therapeutically effective amount" each refer to an amount of a compound or pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art.

As used herein, the terms "administer," "administering," "administered" or "administration" refer to providing a compound or a composition (e.g., one described herein), to a subject or patient. Administration may be by oral administration (i.e., the patient receives the compound or composition via the mouth, as a pill, capsule, liquid, or in other form suitable for administration via the mouth. Oral administration may be buccal (where the compound or composition is held in the mouth, e.g., under the tongue, and absorbed there). Administration may be by injection, i.e., delivery of the compound or composition via a needle, microneedle, pressure injector, or other means of puncturing the skin or forcefully passing the compound or composition through the skin of the patient. Injection may be intravenous (i.e., into a vein); intraarterial (i.e., into an artery); intraperitoneal (i.e., into the peritoneum); intramuscular (i.e., into a muscle); or by other route of injection. Routes of administration may also include rectal, vaginal, transdermal, via the lungs (e.g., by inhalation), subcutaneous (e.g., by absorption into the skin from an implant containing the compound or composition), or by other route.

The term "measuring the level," in the context of liver fat, a hormone such as, e.g., ACTH, cortisol, adrenal hormone, adrenal pre-hormone, or other analyte by non-invasive means, or invasive means, or in a biological fluid or sample, refers determining, detecting, or quantitating the amount, level, or concentration of, for example, cortisol, ACTH or other steroid in a sample obtained from a patient. Non-invasive means may include imaging, such as magnetic resonance imaging (MRI), computer aided tomography (CAT), positron emission tomography (PET), or other scanning or imaging technique. A level may be measured from a sample obtained from a patient. The sample may be, e.g., a blood sample, a saliva sample, a urine sample, or other sample obtained from the patient. A level may be measured from a fraction of a sample. For example, a level (e.g., ACTH or cortisol) may be measured in the plasma fraction of a blood sample; may be measured in a serum fraction of a blood sample; or, in embodiments, may be measured in whole blood.

The terms "glucocorticosteroid" and "glucocorticoid" ("GC") refer to a steroid hormone that binds to a glucocorticoid receptor. Glucocorticosteroids are typically characterized by having 21 carbon atoms, an $\alpha,\beta$-unsaturated ketone in ring A, and an $\alpha$-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

A mineralocorticoid receptor (MR), also known as a type I glucocorticoid receptor (GR I), is activated by aldosterone in humans.

As used herein, the term "glucocorticoid receptor" ("GR") refers to the type II GR, a family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

The term "glucocorticoid receptor modulator" (GRM) refers to any compound which modulates GC binding to GR, or which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

"Glucocorticoid receptor antagonist" (GRA) refers to any compound which inhibits GC binding to GR, or which inhibits any biological response associated with the binding of GR to an agonist. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. A GRA is a compound with an $IC_{50}$ (half maximal inhibition concentration) of less than 10 micromolar. See Example 1 of U.S. Pat. No. 8,859,774, the entire contents of which is hereby incorporated by reference in its entirety.

Exemplary GRMs and GRAs comprising a cyclohexyl pyrimidine structure include those described in U.S. Pat. No. 8,685,973; in U.S. Pat. No. 8,906,917; and in U.S. Pat. No. 9,321,736. In embodiments, the cyclohexyl pyrimidine GRA is the compound (E)-6-(4-Phenylcyclohexyl)-5-(3-trifluoromethylbenzyl)-1H-pyrimidine-2,4-dione (also termed "miricorilant" or "CORT118335"), which has the structure:

"Fatty liver disease" refers to a disease or a pathological condition caused by, at least in part, abnormal hepatic lipid deposits. Fatty liver disease includes, e.g., alcoholic fatty liver disease, nonalcoholic fatty liver disease, and acute fatty liver of pregnancy. Fatty liver disease may be, e.g., macrovesicular steatosis or microvesicular steatosis.

"Nonalcoholic fatty liver disease" or "NAFLD" refers to a fatty liver disease characterized by the presence of fat (lipids) in the liver and no substantial inflammation or liver damage. NAFLD can progress into nonalcoholic steatohepatitis and then into irreversible, advanced liver scarring or cirrhosis.

"Nonalcoholic steatohepatitis" or "NASH" refers a fatty liver disease, which resembles alcoholic liver disease, but occurs in people who drink little or no alcohol. The major feature in NASH is fat in the liver, along with inflammation and cellular death; various stages of fibrosis are also usually seen in NASH. NASH can lead to cirrhosis, in which the liver is permanently damaged and scarred and is no longer able to function properly. NASH may also lead to hepatocellular cancer. A differential diagnosis of NASH versus NAFLD may be determined by liver biopsy. Biomarkers for NASH include, but are not limited to, AST, ALT, GGT, pro-C3, ELF score and its components (hyaluronic acid, TIMP-1, PIIINP).

"Alcohol-related liver disease", "Alcohol-induced liver disease", or "ARLD" refers to diseases of the liver that are wholly, or in part, caused by, or attributable to, excessive consumption of alcohol. There are four main types of ARLD, alcoholic fatty liver (AFL, a sub-type of fatty liver disease), alcoholic steatohepatitis (ASH), alcoholic-induced cirrhosis, and alcoholic hepatocellular cancer. Various stages of fibrosis may also be seen in ASH or other types of ARLD. As used herein, "excessive consumption of alcohol" generally refers to the consumption of more than about 15-30 g/day of ethanol.

The physiological effects of alcohol consumption on liver function or disease are dependent on a variety of genetic and non-genetic factors that modify both individual susceptibility and the clinical course of ARLD.

"Liver disorder unrelated to excessive ingestion of alcohol" is a liver disorder that is distinguished from ARLD. Such a disorder therefore refers to a wide array of liver diseases that are not caused by alcohol consumption. For example, hepatitis can be caused by viral infection. A liver disorder caused by excessive alcohol consumption and other factors, is considered an ARLD rather than a liver disorder unrelated to excessive ingestion of alcohol. In contrast, a liver disorder merely exacerbated by excessive alcohol consumption is considered a liver disorder unrelated to excessive ingestion of alcohol.

As used herein, "Hy's law" refers to the increased risk of severe liver damage indicated by a total bilirubin level greater than twice the upper limit of normal (ULN) for bilirubin, and liver enzyme (ALT or AST) levels greater than three times the ULN for those enzymes determined from patient laboratory test results.

As used herein, "Temple's Corollary" refers to the lesser risk of liver damage, as compared to the risk indicated by patients meeting the criteria for "Hy's Law", indicated by patient laboratory test results in which peak ALT levels are greater than 3 times the ULN for ALT, but with bilirubin levels are less than twice the ULN for bilirubin.

As used herein, the term "cholestasis" refers to the liver condition caused by impaired or blocked flow of bile through the bile duct; cholestasis is characterized by increased bilirubin in the blood, and typically by jaundice (yellowing) of the skin and sclera.

As used herein, the term "steatosis" refers to a condition characterized by fat build-up in liver cells, leading to excess fat in the liver (abnormally high levels of liver fat, as compared to normal levels of liver fat).

As used herein, the term "fibrosis" refers to scarring; liver fibrosis refers to scarring of the liver. Liver fibrosis is a liver disease, and is typically found in individuals who have suffered from fatty liver disease, either alcohol related or nonalcoholic, for an extended period of time.

As used herein, the term "FibroScan" refers to an ultrasound examination of the liver used to identify liver disease, such as a fatty liver disease. It provides quantitative measures of liver steatosis and liver fibrosis, and may be used to help identify, diagnose, or track the course of liver diseases including, e.g., liver steatosis, liver fibrosis, and other liver disorders.

As used herein, the term "MRI" refers to magnetic resonance imaging, a non-invasive technique which provides images of internal organs and tissues, useful for diagnostic and therapeutic procedures.

As used herein, the term "MRI-PDFF" refers to magnetic resonance imaging-proton density fat fraction. MRI-PDFF is an MRI technique that provides an assessment of the amount, and fraction, of fat in a tissue, such as liver tissue, and can be used to quantify liver fat.

Fatty Liver Disease

Fatty liver disease (FLD, also known as hepatosteatosis) is a prevalent liver condition that occurs when lipids accumulate in liver cells. The lipid accumulation causes cellular injury and makes the liver susceptible to further injuries. Fatty liver disease is characterized by the build-up of excessive fat (lipids) in liver cells, generally caused by abnormal retention of lipids by the liver cells (i.e., steatosis). In addition to fat, proteins and water are retained in the hepatocytes, which can lead to a ballooning of hepatocytes. The accumulation of fat in the liver may be attributed to a perturbation of one of the following steps in the lipid metabolism of hepatocytes and adipocytes: (1) increased free fatty acid delivery to the liver; (2) increased free fatty acid synthesis within the liver; (3) decreased beta-oxidation of fatty acids; and (4) decreased very low-density lipoprotein synthesis or secretion. (Bacon et al., *Gastroenterology,* 1994, 107:1103-1109).

Liver fat is typically less than 5% of liver tissue (where % may be determined by volume, by histology (e.g., % hepatocytes exhibiting macrovesicular steatosis) by MRI-PDFF techniques, by weight (e.g., % of triglyceride of wet liver weight), or by other accepted methods). Amounts of liver fat greater than about 5% are typically considered pathological. Liver fat may be measured by liver biopsy, by MRS (magnetic resonance spectroscopy), by other imaging techniques such as, e.g., FibroScan and MRI-PDFF, or by other means.

FLD may arise from a number of sources, including excessive alcohol consumption and metabolic disorders, such as those associated with insulin resistance, obesity, and hypertension. The disease is most prevalent in individuals who are obese or who have diabetes. In alcohol induced fatty liver disease (AFL) initially fat accumulates in liver cells, but then the disease can progress to alcoholic hepatitis which causes the liver to swell and become damaged if the individual continues to consume alcohol. The individual can also develop alcoholic cirrhosis, or scarring of the liver which in turn can cause liver failure. Heavy drinkers can progress from AFL to alcoholic hepatitis to alcoholic cirrhosis over time.

Nonalcoholic fatty liver disease (NAFLD) is a liver disorder with histological features of AFL but in individuals who consume little to no alcohol. Like AFL, NAFLD is due to the abnormal retention of fat (lipids) by hepatocytes. Other fatty liver diseases can develop in a patient with other types of liver diseases, such as but not limited to, chronic viral hepatitis C (HCV), chronic viral hepatitis B (HBV), chronic autoimmune hepatitis (AIH), diabetes and Wilson's disease. Fatty liver can also be associated with indications caused by disruptions in lipid metabolism, such as disorders due to drugs, e.g., gastrointestinal disorders (e.g., intestinal bacterial outgrowth, gastroparesis and irritable bowel syndrome), chemotherapy, gastrointestinal surgeries for obesity, malnutrition and genetic defects in proteins that process lipids.

In some embodiments, the fatty liver disease is a nonalcoholic fatty liver disease (NAFLD) or is an alcohol related liver disease (ARLD). In some instances, the nonalcoholic fatty liver disease is nonalcoholic steatohepatitis (NASH) or nonalcoholic cirrhosis. In some instances, the alcohol related liver disease is alcohol fatty liver disease (AFL), alcoholic steatohepatitis (ASH) or alcoholic cirrhosis.

A. Non-Alcoholic Fatty Liver Disease (NAFLD)

NAFLD is characterized by hepatic steatosis, and may progress to non-alcoholic steatohepatitis (NASH), which is characterized by liver inflammation, steatosis, necrosis and fibrosis due to the disruption of liver cells. Conditions associated with NAFLD are varied, and include type 2 diabetes, obesity, dyslipidemia, metabolic syndrome, treatment with hepatotoxic drugs, toxins, infectious agents, or other exogenous causes. For instance, NAFLD may result from metabolic disorders such as, e.g., galactosemia, glycogen storage diseases, homocystinuria, and tyrosemia, as well as dietary conditions such as malnutrition, total parenteral nutrition, starvation, and overnutrition. In certain cases, NAFLD is associated with jejunal bypass surgery. Other causes include exposure to certain chemicals such as, e.g., hydrocarbon solvents, and certain medications, such as, e.g., amiodarone, estrogens (e.g., synthetic estrogens), tamoxifen, maleate, methotrexate, nucleoside analogs, and perhexiline. Acute fatty liver conditions can also arise during pregnancy.

NAFLD typically follows a benign, non-progressive clinical course, however, NASH is a potentially serious condition. As many as 25% of NASH patients may progress to advanced fibrosis, cirrhosis and experience complications of portal hypertension, liver failure and hepatocellular carcinoma (Yeh and Brunt, *Am J Clin Pathol,* 2007, 128(5):837-47).

Individuals with NAFLD may be asymptomatic but clinical lab tests can show elevated liver enzyme levels. Individuals may exhibit symptoms of NAFLD, such as abdominal discomfort (e.g., discomfort in the right upper abdominal quadrant), acanthosis nigricans, bowel dismotility, coma, constipation, disseminated intravascular coagulopathy, epigastric pain, fatigue, malaise, hepatomegaly (generally with a smooth, firm surface upon palpation), hypoglycemia, jaundice, lipomatosis, lipoatrophy, lipodystrophy, nausea, neurological defects, Palmer erythema, panniculitis, periumbilical pain, small bowel bacterial overgrowth, spider angiomata, splenomegaly, subacute liver failure, and vomiting. Clinical evaluation to rule out alcohol related fatty liver disease may include determining if the individual consumes excess alcohol (e.g., greater than 60 g/day for men and greater than 20 g/day for women within the past 5 years. The presence or level of anti-hepatitis C antibody and serum ceruloplasmin levels can be used to indicate that the individual has NAFLD.

Non-invasive evaluation of biochemistry and metabolism can used to diagnose NAFLD and NASH. By using a biological sample such as blood, plasma or serum, high level of enzymes such as alanine aminotransferase (ALT), aspartate aminotransfersase (AST), alkaline Phosphatase (AP), and/or 7 glutamyl transpeptidase (GGT), as well as the presence of other proteins of liver origin (including haptoglobin, total bilirubin, alpha-2-microglobulin, resistin, cleaved or intact cytokeratin-18) are commonly measured in addition to serum glucose and insulin resistance parameters. Since the level of ALT activity is frequently increased in NASH patients (Angulo and Lindor, *Best Pract Res Clin Gastroenterol*, 2002, 16(5):797-810), this criteria is considered as a surrogate marker for assessing liver injury.

In an individual suspected of having NAFLD or NASH, baseline testing of serum may include measuring or determining levels of AST, ALT, total and direct bilirubin, and fasting serum glucose, as well as a lipid panel. For example, steatosis may be indicated by elevated serum levels (often moderately elevated, e.g., elevated approximately 2, 3, 4, 5, 6, 7, 9, 10, 11, or 12-fold above normal levels) of liver enzymes (such as, e.g., AST, ALT, GGT and alkaline phosphatase) when other causes (such as, e.g., acute hepatitis, autoimmune disease, chronic hepatitis, cirrhosis, fulminant hepatitis, hepatocellular carcinoma, metastatic carcinoma, right heart failure, and viral hepatitis) have been eliminated. For example, ALT values greater than 32, 24, or 56 units per liter of serum or at least 2, 3, 4, 5, 6, 7, 8, 9, 10, 11, 12, or more times normal values may be indicative of a disorder associated with hepatic lipid deposits, or by AST values greater than 40 units per liter of serum or at least 2, 3, 4, 5, 6, 7, 8, 9, 10, 11, 12, or more times normal values. Mild to moderate elevation of serum aminotransferase levels is most commonly found (mean range, 100-200 IU/L). The ratio of AST/ALT is often less than one in NAFLD, but may be greater than one in patients with alcoholic liver disease or advanced liver disease or if the patient advances to fibrosis. GGT levels may also be significantly elevated, e.g., at least 2, 3, 4, 5, 6, 7, 8, 9, 10, 11, 12, or more times normal values as defined by a normal, healthy individual. Liver enzyme levels can be normal in a large percentage of patients with NAFLD, thus normal AST or ALT levels do not exclude the presence of advanced disease. Serum alkaline phosphatase and GGT levels may be mildly abnormal. Given that more than 80% of patients with NAFLD have some components of metabolic syndrome, serum levels of fasting cholesterol and triglycerides, as well as fasting glucose and insulin, may be determined. Albumin, bilirubin, and platelet levels may be normal unless the disease has evolved to cirrhosis. Some patients with NAFLD have low titers of autoimmune antibodies (e.g., antinuclear and anti-smooth muscle antibodies) and an elevation of ferritin (Carey et al., "Nonalcoholic Fatty Liver Disease" in *Current Clinical Medicine, 2ⁿᵈ* edition, Elsevier, New York. In some embodiments, an AST/ALT ratio of greater than 1 can predict more advanced fatty liver disease.

Radiologic methods such as, but not limited to, x-ray imaging, ultrasonography, computed tomography (CT), magnetic resonance imaging (MRI), and magnetic resonance spectroscopy can be used to detect liver diseases such as, e.g., a NAFLD, or an ARLD. MRI-PDFF is an MRI technique useful for diagnosing a fatty liver disease, and for tracking the progress of a liver disease, and for detecting and tracking the progress of a therapy for a liver disease. With ultrasonography, increased echogenicity of the liver compared to the kidneys can indicate liver steatosis. For example, FibroScan is an ultrasound technique useful for diagnosing a fatty liver disease, and for tracking the progress of a liver disease, and for detecting and tracking the progress of a therapy for a liver disease.

NASH can be diagnosed using histopathological methods on liver samples (e.g., biopsies) to assess macrovesicular steatosis, ballooning degeneration, hepatocyte necrosis, lobular inflammation, megamitochondria, infiltration of inflammatory cells, apoptosis, and fibrosis (see, e.g., Brunt and Tiniakos, *World J Gastroenterol*, 2010, 16(42):5286-8296). Hepatocytic ballooning is characterized by swelling and enlargement of the cells, and sometimes the appearance of cytoplasmic alterations containing Mallory-Denk bodies. Fibrosis can also develop over time, initially as pericellular/pervenular fibrosis and eventually to portal-central bridging fibrosis and cirrhosis.

Hematoxylin and eosin (H&E), Masson trichrome, Oil Red O and immunohistochemical staining and other standard histological methods known to those of ordinary skill in the art can be performed to analyze tissue and cellular features. A scoring system (e.g., a NAFLD activity score) that includes one or more histological features can be used to score and diagnose NAFLD, including NASH. In some embodiments, the NASH Clinical Research Network Scoring System developed by the Pathology Committee of the NASH Clinical Research Network (see, e.g., Kleiner et al., *Hepatology*, 2005, 41(6): 1313-1321) can be used predict whether an individual has NAFLD or NASH. The Practice Guidelines published by the American Gastroenterological Association, American Association for the Study of Liver Diseases, and American College of Gastroenterology (Chalasani et al., *Gastroenterology*, 2012, 142: 1592-1609) can be followed by a clinician to diagnose or monitor NAFLD, including non-alcoholic fatty liver, NASH and NASH associated cirrhosis.

An individual's liver may be considered to be steatotic when a biopsy reveals at least 5-10% w/w fatty deposits (See, e.g., Clark et al., *J. Am. Med. Assoc.*, 2003, 289:3000-3004 (2003) and Adams et al., *Can. Med. Assoc. J.*, 2005, 172:899-905). A liver with fatty deposits comprising up to 25% (w/w) may be considered mildly steatotic, and a liver with fatty deposits comprising greater than 25% (w/w) may be considered severely steatotic.

Treatments for NAFLD including NASH include exercise, weight loss and avoiding hepatotoxins or any substance that may damage the liver. In some embodiments, therapies include administration of antioxidants, cytoprotective agents, antidiabetic agents, insulin-sensitizing agents (e.g. metformin), anti-hyperlipidemic agents, other chemical compounds, such as fibrates, thiazolidinediones (i.e., rosigli-tazone or pioglitazone), biguanides, statins (or other agents affecting HMG-CoA reductase), cannabinoids, and other therapeutic compounds or molecules that target nuclear receptors, angiotensin receptors, or cannabinoid receptors.

Efficacy of treatment may be determined by detecting a reduction in one or more symptoms or clinical manifestations of a disease as well as any of the tests described above for diagnosis.

B. Alcohol Related Liver Disease (ARLD)

Alcohol-related liver disease (ARLD) describes a family of alcohol-related, or alcohol-induced, liver pathologies including alcohol induced fatty liver disease (AFL), alcoholic hepatitis, and alcoholic cirrhosis. Virtually all persons who are chronic and heavy consumers of alcohol will develop AFL. Additionally, due to the high prevalence of complicating factors such as obesity, diabetes, and metabolic syndrome in the general population, many individuals who do not satisfy the criteria for chronic heavy consumers of alcohol are susceptible to developing AFL.

AFL can be diagnosed via ultrasound. Typically, the liver of a patient with AFL presents as "echogenic," meaning more dense than usual to the imaging sound waves. In addition, the liver is typically enlarged due to the swelling and presence of large amounts of fat.

AFL can also be indicated by, and thus diagnosed due to, presentation of one or more symptoms or risk factors (e.g., obesity, diabetes, drinking behavior, etc.). Fatty liver disease can present symptoms such as fatigue, muscle weakness, abdominal discomfort, weight loss, and confusion. However, fatty liver disease usually does not present overt physical symptoms. Fatty liver disease can also be accompanied by, or precede, inflammation of the liver or hepatic fibrosis. Patients with fatty liver disease generally present elevated serum liver enzyme levels. Moreover, the relative levels of several liver enzymes are altered. AFL generally presents with a serum aspartate aminotransferase (AST) level that is greater than the level of alanine aminotransferase (ALT). This is distinguished from non-alcoholic fatty liver disease, in which ALT is higher than AST.

In certain patients, ARLD can develop at much lower rates of alcohol consumption, including consumption of at least about 12 g/day, 15 g/day, 20 g/day, 25 g/day or more. Moreover, it is understood that in some patients, estimates of daily consumption of alcohol are an average value that includes periods of heavy alcohol consumption and periods of little or no alcohol consumption. Such an average value can include an average of alcohol consumption over at least about a week, two weeks, a month, three months, six months, nine months, a year, 2, 3, or 4 years, or more. In some cases, the determination of whether a liver dysfunction is an ARLD is based on reference to a variety of factors including, but not limited to: the amount and type of alcoholic beverage consumption (e.g., beer or spirits); the duration of alcohol abuse; patterns of drinking behavior (e.g., binge drinking, drinking without co-consumption of food, etc.); gender; ethnicity; co-existing disease conditions such as metabolic syndrome or diabetes, iron overload, or infection with hepatitis virus, genetic markers; family history; liver enzyme levels; proinflammatory cytokine levels; gene or protein expression analysis; or histopathological examination of liver tissue or cells.

There are four main pathogenic factors for AFL: (1) Increased generation of NADH caused by alcohol oxidation, favoring fatty acid and tri-glyceride synthesis, and inhibiting mitochondrial β-oxidation of fatty acids. (2) Enhanced hepatic influx of free fatty acids from adipose tissue and of chylomicrons from the intestinal mucosa. (3) Ethanol-mediated inhibition of adenosine monophosphate activated kinase (AMPK) activity resulting in increased lipogenesis and decreased lipolysis by inhibiting peroxisome proliferating-activated receptor α (PPARα) and stimulating sterol regulatory element binding protein 1c (SREBP1c). And, (4) Damage to mitochondria and microtubules by acetaldehyde, which results in a reduction of NADH oxidation and the accumulation of very low density lipoprotein (VLDL), respectively.

Successful treatment of AFL is indicated by improvement of one or more clinical, laboratory, or histopathological symptoms. For example, successful treatment can be indicated by a reduction in volume of fatty liver, e.g., as exhibited by ultrasound examination. As another example, successful treatment can be indicated by a reduction of one or more clinical symptoms such as fatigue, weakness, or cessation of weight loss. As another example, successful treatment can be indicated by a normalization of liver enzyme levels or relative levels (e.g., normalization of the aspartate aminotransferase/alanine aminotransferase ratio).

Alcoholic hepatitis, or alcoholic steatohepatitis (ASH), is the next stage of ARLD after AFL. As such, AFL is a pre-requisite for development of ASH. Seventeen percent of all liver biopsies of patients who are admitted for alcohol detoxification reveal ASH and 40% of patients with alcoholic cirrhosis also have ASH in a cirrhotic liver. Twenty-five percent of patients develop excessive liver necrosis with clinical signs of hepatic failure and hepatic encephalopathy. In severe cases ASH may cause profound liver damage, increased resistance to blood flow and is associated with a poor prognosis. Acute mortality of severe ASH is between about 15% and 25%. ASH is characterized by an inflammation of the liver. Various factors may contribute to the development of ASH, including: (1) acetaldehyde-induced toxic effects; (2) reactive oxygen species (ROS) generation and the resulting lipid peroxidation; (3) upregulation of proinflammatory cytokines; and (4) impaired ubiquitin-proteasome pathway function.

Acetaldehyde binds to proteins and to DNA resulting in functional alterations and protein adducts. Such adducts can activate the immune system by forming autoantigens. Acetaldehyde also induces mitochondria damage and impairs glutathione function, leading to oxidative stress and apoptosis.

The main sources of ROS are CYP2E1-dependent mitochondrial electron transport, NADH-dependent cytochrome reductase, and xanthine oxidase. Chronic alcohol intake markedly up-regulates CYP2E1, which exacerbates ROS generation. Moreover, CYP2E1 metabolizes ethanol to acetaldehyde resulting in further alteration of protein and DNA.

Alcohol metabolites and ROS stimulate signaling pathways such as those mediated by NF-κB, STAT-JAK, and JNK in hepatic resident cells, leading to the local synthesis of inflammatory mediators such as TNFα and CXC chemokines (e.g., interleukin-8), as well as osteopontin. Alcohol abuse also results in changes in the colonic microbiota and increased intestinal permeability, leading to elevated serum levels of lipopolysaccharides that induce inflammatory actions in Kupffer cells via CD14/TLR4. The resulting inflammatory milieu in the alcoholic liver leads to polymorphonuclear leukocyte (PMN) infiltration, ROS formation and hepatocellular damage.

ASH histopathology can be characterized by ballooning degeneration of hepatocytes associated with necrosis, enhanced apoptosis, and frequently, the occurrence of Mallory Denk bodies (MDBs). ASH histopathology can also exhibit infiltration of immune cells, including polymorphonuclear cells, T-lymphocytes, or natural killer cells. MDBs are associated with poor prognosis. In addition to MDB, giant mitochondria can be observed in the liver cells of patients with ASH. Additional histopathological characteristics of ASH include macrovesicular steatosis, microvesicular steatosis, lobular hepatitis, nuclear vacuoles, ductular proliferation, perivencular fibrosis, and fibrosis or cirrhosis.

Patients with ASH may develop progressive fibrosis. In ARLD, the fibrotic tissue is typically located in pericentral and perisinusoidal areas. In advanced stages, collagen bands are evident and bridging fibrosis develops. This condition precedes the development of regeneration nodules and liver cirrhosis. The cellular and molecular mechanisms of fibrosis in ARLD are not completely understood. Alcohol metabolites such as acetaldehyde can directly activate hepatic stellate cells (HSC), the main collagen-producing cells in the injured liver. HSC can also be activated paracrinally by damaged hepatocytes, activated Kupffer cells and infiltrating PMN cells. These cells release fibrogenic mediators such as growth factors (TGF-ß1, PDGF), cytokines (leptin, angiotensin II, interleukin-8, and TNFα), soluble mediators (nitric oxide), and ROS. Importantly, ROS stimulate pro-fibrogenic intracellular signaling pathways in HSC including those mediated by ERK, PI3K/AKT, and INK. They also up-regulate TIMP-1 and decrease the actions of metalloproteinases, thereby promoting collagen accumulation. Cells other than HSC can also synthesize collagen in ARLD. They include portal fibroblasts and bone-marrow derived cells.

ASH can be classified into mild, moderate, and severe forms due to the intensity and frequency of a wide variety of subjective and objective clinical findings. Clinical symptoms of ASH include: nonspecific upper right quadrant pain, nausea, and emesis, frequently accompanied by fever and jaundice. Other symptoms include: fatigue, dry mouth and increased thirst, or bleeding from enlarged veins in the walls of the lower part of the esophagus. Other skin conditions indicative of ASH include: small red spider-like veins on the skin, very dark or pale skin, redness on the feet or hands, or itching. Patients with ASH may also present with symptoms of alcohol withdrawal and signs of malnutrition. Further clinical markers include hepatomegaly, ascites, anorexia, encephalopathy, splenomegaly, weight loss, pancreatitis, or gastrointestinal bleeding. In severe cases, patients can exhibit problems with thinking, memory, and mood, fainting or lightheadedness, or numbness in legs and feet.

Serum and blood markers of ASH include an increase in the activity of aspartate aminotransferase and alanine aminotransferase, accompanied by a higher level of aspartate aminotransferase over alanine aminotransferase. Typically, gamma glutamyl peptidase is also elevated in ASH patients. Elevated gamma glutamyl peptidase is generally considered due to enzyme induction by ethanol; however, aspartate aminotransferase and alanine aminotransferase levels are considered to be markers of liver cell damage. 40-80% of patients also present with elevated alkaline phosphatase activity levels. In severe ASH, beta and gamma globulin levels are elevated. In addition, ASH can present with elevated leukocyte count with toxic granulation and fever. Hematologic abnormalities for ASH include macrocytic hyperchromic anemia and thrombocytosis. Severe ASH can also exhibit reduction in parameters indicative of primary liver function such as prothrombin time, serum bilirubin, or serum albumin. In some cases, ASH can be detected by the presence of urine bilirubin.

ASH is generally indistinguishable from AFL via ultrasound. However ultrasound can be useful to exclude extrahepatic cholestasis, which can present similar clinical symptoms (e.g., jaundice). If diagnosis cannot be established by examination of clinical markers, serum or blood markers, and ultrasound, a liver biopsy may be performed. Liver biopsy can also be helpful to determine the severity of the disease or to guide pharmacological intervention.

Successful treatment of ASH is indicated by improvement of one or more clinical, laboratory, or histopathological symptoms. For example, successful treatment can be indicated by a reduction in volume of fatty liver, e.g., as exhibited by ultrasound examination. As another example, successful treatment can be indicated by a reduction of one or more clinical symptoms such as fatigue, weakness, or cessation of weight loss. As another example, successful treatment can be indicated by a normalization of liver enzyme levels or relative levels (e.g., normalization of the aspartate aminotransferase/alanine aminotransferase ratio). As yet another example, successful treatment can be indicated by a reduction in beta and gamma globulin levels or alkaline phosphatase levels. As another example, restoration or improvement of parameters of primary liver function such as prothrombin time, serum or urine bilirubin, and serum albumin can indicate successful treatment. As yet one more example, successful treatment can be indicated by amelioration, or cessation, of one or more of hepatomegaly, ascites, anorexia, encephalopathy, splenomegaly, weight loss, pancreatitis, or gastrointestinal bleeding.

Alcoholic cirrhosis is a late stage of serious liver disease marked by inflammation, swelling, fibrosis, damaged cellular membranes, scarring, and necrosis. Between about 10% to about 20% of heavy drinkers will develop cirrhosis of the liver. Symptoms of cirrhosis include, but are not limited to, jaundice, liver enlargement, and pain and tenderness. Successful treatment can be indicated by any reduction in the rate of progression of liver function deterioration.

Efficacy of treatment may be determined by detecting a reduction in one or more symptoms or clinical manifestations of a disease as well as any of the tests described above for diagnosis.

Pharmaceutical Compositions and Administration

In embodiments, the present invention provides a pharmaceutical composition for reducing levels of fat in the liver of a patient in need of such reduction, for treating abnormally high levels of liver fat, and for treating fatty liver disease and related disorders, the pharmaceutical composition including miricorilant and a pharmaceutically acceptable excipient.

Pharmaceutical compositions including miricorilant can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. Miricorilant may also be administered by injection, that is, intravenously, intramuscularly, intracutaneously, subcutaneously, intraduodenally, or intraperitoneally. In embodiments, miricorilant can be administered by inhalation, for example, intranasally, or miricorilant can be administered transdermally. Accordingly, the present invention also provides pharmaceutical compositions including a pharmaceutically acceptable carrier or excipient and miricorilant for use in reducing liver fat, for treating abnormally high levels of liver fat, for treating fatty liver disease, and for treating related disorders. Details on techniques for formulation and administration of pharmaceutical compositions are well described in the scientific and patent literature, see, e.g., the latest edition of Remington's Pharmaceutical Sciences, Mack Publishing Co, Easton PA ("Remington's"), which is hereby incorporated by reference in its entirety. Formulations comprising miricorilant are disclosed in U.S. application 63/020,919, entitled "Formulation of Pyrimidine Cyclohexyl Glucocorticoid Receptor Modulators", filed May 6, 2020, the entire contents of which is hereby incorporated by reference in its entirety.

The pharmaceutical preparation is preferably in unit dosage form. In such form the preparation is subdivided into unit doses containing appropriate quantities of the active component, a GRM. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 milligram (mg) to 10000 mg, more typically 1.0 mg to 2000 mg, most typically 10 mg to 1000 mg. Suitable dosages also include about 1, 5, 10, 20, 30, 40, 50, 60, 70, 80, 90, 100, 200, 300, 400, 500, 600, 700, 800, 900, 1000, 1100, 1200, 1300, 1400, 1500, 1600, 1700, 1800, 1900, or 2000 mg, according to the particular application and the potency of the active component. The composition can, if desired, also contain other compatible therapeutic agents.

Pharmaceutical compositions containing miricorilant can be administered orally. For example, miricorilant can be administered as a pill, a capsule, or liquid formulation as described herein. Alternatively, in other embodiments, miricorilant can be provided via parenteral administration. For example, miricorilant may be administered intravenously (e.g., by injection or infusion). Additional methods of administration of the compounds described herein, and pharmaceutical compositions or formulations thereof, are described herein.

In some embodiments, miricorilant is administered in one dose. In other embodiments, miricorilant is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount may vary according to, for example, patient characteristics.

Any suitable miricorilant dose may be used in the methods disclosed herein. The miricorilant dose that is administered can be at least about 10 milligrams (mg) per day, or about 25 mg/day, or about 50 mg/day, or about 75 mg/day, about 100 mg/day, about 150 mg/day, about 200 mg/day, about 250 mg/day, about 300 mg/day, about 350 mg/day, about 400 mg/day, about 450 mg/day, about 500 mg/day, about 550 mg/day, about 600 mg/day, about 650 mg/day, about 700 mg/day, about 750 mg/day, about 800 mg/day, about 850 mg/day, about 900 mg/day, about 950 mg/day, about 1000 mg/day, about 1100 mg/day, or more. In embodiments, miricorilant is administered orally. In some embodiments, miricorilant is administered in at least one dose. In other words, miricorilant can be administered in 1, 2, 3, 4, 5, 6, 7, 8, 9, 10 or more doses. In embodiments, miricorilant is administered orally in 1, 2, 3, 4, 5, 6, 7, 8, 9, 10 or more doses. In embodiments, miricorilant is administered orally with food in 1, 2, 3, 4, 5, 6, 7, 8, 9, 10 or more doses. In embodiments, miricorilant is administered orally without food in 1, 2, 3, 4, 5, 6, 7, 8, 9, 10 or more doses.

The patient may be administered at least one dose of GRM in one or more doses over, for example, a 2-hour to 48-hour period. In some embodiments, miricorilant is administered as a single dose. In other embodiments, miricorilant is administered in more than one dose, e.g. 2 doses, 3 doses, 4 doses, 5 doses, or more doses over a 2-48 hour period, e.g., a 2 hour period, a 3 hour period, a 4 hour period, a 5 hour period, a 6 hour period, a 7 hour period, a 8 hour period, a 9 hour period, a 10 hour period, a 11 hour period, a 12 hour period, a 14 hour period, a 16 hour period, a 18 hour period, a 20 hour period, a 22 hour period, a 24 hour period, a 26 hour period, a 28 hour period, a 30 hour period, a 32 hour period, a 34 hour period, a 36 hour period, a 38 hour period, a 40 hour period, a 42 hour period, a 44 hour period, a 46 hour period or a 48 hour period. In some embodiments, miricorilant is administered over 2-48 hours, 2-36 hours, 2-24 hours, 2-12 hours, 2-8 hours, 8-12 hours, 8-24 hours, 8-36 hours, 8-48 hours, 9-36 hours, 9-24 hours, 9-20 hours, 9-12 hours, 12-48 hours, 12-36 hours, 12-24 hours, 18-48 hours, 18-36 hours, 18-24 hours, 24-36 hours, 24-48 hours, 36-48 hours, or 42-48 hours.

The duration of treatment with miricorilant to reduce liver fat or treat a fatty liver disease can vary according to the severity of the condition in a patient and the patient's response to miricorilant. In some embodiments, miricorilant can be administered for a period of about 1 week to 104 weeks (2 years), more typically about 6 weeks to 80 weeks, most typically about 9 to 60 weeks. Suitable periods of administration also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. In general, administration of miricorilant should be continued until clinically significant reduction or amelioration is observed. Treatment with miricorilant in accordance with the invention may last for as long as two years or even longer.

In some embodiments, miricorilant administration is not continuous and can be stopped for one or more periods of time, followed by one or more periods of time where administration resumes. Suitable periods where miricorilant administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where miricorilant administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

A pharmaceutical composition including miricorilant can be placed in an appropriate container and labeled for treatment of an indicated condition. A kit for reducing liver fat in a patient in need thereof, and a kit for treating a fatty liver disease in a patient in need thereof, contains a pharmaceutical composition containing miricorilant and a label including instructions for its use in reducing liver fat or for treating a fatty liver disease. For administration of miricorilant, such labeling would include, e.g., instructions concerning the amount, frequency and method of administration.

I. Combination Therapies

Various combinations with miricorilant and another agent (or a combination of such agents) may be employed to reduce liver fat or to treat a fatty liver disease in a patient. By "combination therapy" or "in combination with", it is not intended to imply that the therapeutic agents must be administered at the same time and/or formulated for delivery together, although these methods of delivery are within the scope described herein.

Miricorilant can be used in combination with other active agents (e.g., diabetes medications such as, e.g., insulin, metformin, sulfonylureas, biguanides, and others; statins; anti-fibrotic agents such as, e.g., ASK-1 inhibitors such as selonsertib, CCR2/CCR5 inhibitors such as cenriviroc, or FXR agonists such as obeticholic acid; and other agents) known to be useful in modulating a glucocorticoid receptor, or for treating a fatty liver disease, or with adjunctive agents that may not be effective alone, but may contribute to the efficacy of the active agent.

In some embodiments, co-administration includes administering one active agent, miricorilant, within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

Miricorilant and the other therapeutic agent can be administered following the same or different dosing regimen. In some embodiments, miricorilant and the other therapeutic agent are administered sequentially in any order during the entire or portions of the treatment period. In some embodiments, miricorilant and the other therapeutic agent are administered simultaneously or approximately simultaneously (e.g., within about 1, 5, 10, 15, 20, or 30 minutes of each other). Non-limiting examples of combination therapies are as follows, with administration of the GRM and another pharmaceutical agent for example, miricorilant is "A" and another therapeutic agent or compound is "B":

| |
|---|
| A/B/AB/A/BB/B/AA/A/BA/B/BB/A/AA/B/B B/A/B/B |
| B/B/B/A B/B/A/B A/A/B/B A/B/A/B A/B/B/A B/B/A/A |
| B/A/B/A B/A/A/B A/A/A/B B/A/A/A A/B/A/A A/A/B/A |

Administration of the therapeutic compounds or agents to a patient will follow general protocols for the administration of such compounds, taking into account the toxicity, if any, of the therapy. Surgical intervention may also be applied in combination with the described therapy.

The present methods can be combined with other means of treatment including, e.g., dietary changes, exercise, surgery, and other treatments.

EXAMPLES

The following examples are provided by way of illustration only and not by way of limitation. Those of skill will readily recognize a variety of noncritical parameters which could be changed or modified to yield essentially similar results.

Example 1

A Phase 2a, randomized, double-blind, placebo-controlled study (ClinicalTrials.gov Identifier: NCT03823703)

was begun to assess the efficacy of two dose levels of miricorilant versus placebo in reducing liver fat in patients who were presumed to have non-alcoholic steatohepatitis (NASH), that presumption based on blood tests and noninvasive measures. Written informed consent was obtained before initiating any study-mandated procedures. The full study was planned to enroll approximately 120 patients, randomized 1:1:1 to receive daily 900 mg miricorilant:600 mg miricorilant: matching placebo. As illustrated in FIG. 1, the full study consists of the following study periods: a) an initial Screening Period of up to 6 weeks; b) a Treatment Period of 12 weeks, with Day 1 measurements serving as baseline measurements; and c) a Follow-Up Period of 4 weeks after the last dose of the study drug (miricorilant or placebo).

Patients enrolled in the study were required to have consistent liver enzyme (ALT and AST) baseline measurements (established by two samples obtained at least 4 weeks and no more than six months apart), and a diagnosis of presumed NASH with fibrosis defined as meeting all of the following criteria:

a. Either: i) a historical liver biopsy within 1 year of Screening showing NASH, NAFLD Activity Score (NAS) greater than or equal to 4, and F1 to F3 fibrosis, or ii) an AST level greater than 17 U/L for women or AST level greater than 20 U/L for men AND a FibroScan liver stiffness measurement of greater than or equal to 8.5 kPa and a Controlled Attenuation Parameter (CAP) of greater than or equal to 300 dB/m in the 3 months prior to Screening or at Screening;
   b. A MRI-PDFF with greater than or equal to 10% steatosis; and
   c. The presence of two or more components of metabolic syndrome: type 2 diabetes treatment or fasting blood glucose greater than or equal to 126 mg/dL, BMI greater than or equal to 30 kg/m$^2$, hypertension treatment or blood pressure greater than or equal to 130/85, history of dyslipidemia, or waist circumference greater than or equal to 102 cm (40 in) in men and greater than or equal to 88 cm (35 in) in women.

Exclusion criteria were used to exclude patients not suitable for the study. Patients who met any of the exclusion criteria were not eligible to participate in the study; such exclusion criteria included pregnancy or lactation; participation within the last year in another clinical trial where patient received active treatment for NASH, or received miricorilant, or other trials for any other indication within the last 3 months or 5 half-lives of the treatment, whichever is longer; a BMI less than 18 kg/m$^2$; current use of prohibited medications; weight-loss surgery; significant alcohol consumption (defined as more than 2 drink units per day (equivalent to 20 g of ethanol) in women and 3 drink units per day (equivalent to 30 g of ethanol) in men for greater than or equal to 3 consecutive months within 1 year prior to Screening); liver transplantation; type 1 diabetes; type II diabetes with the following: HbA1c ≥9.5%, recent significant insulin dose adjustment, history of severe hypoglycemia, and requirement for further anti-diabetic medication; recent abnormal weight loss; abnormal AST or ALT (greater than 5-times ULN), creatine kinase, or estimated glomerular filtration rate (eGFR); cirrhosis or other chronic liver disease; hypertension; and other exclusion criteria.

All patients were randomly assigned to the study drug (one of the 3 treatment groups) using a centralized interactive web response system (IWRS); patients were assigned a unique identifier and treatment allocation was performed using the IWRS system. Tablets (miricorilant, 150 mg or placebo for miricorilant tablet, 150 mg) were identical in appearance. All those associated with the study (sponsor, the Investigator, the Medical Monitor, study-site personnel, and the patient) were blinded to the study drug and were not allowed to view the results of laboratory tests that have the potential to reveal a patient's treatment arm due to the expected effect of the active treatment on the analyte involved. The IWRS was programmed with blind-breaking instructions.

Measures of the effectiveness of miricorilant versus placebo in reducing liver fat were assessed by magnetic resonance imaging (MRI). The change from baseline MRI measurements relative to MRI measurements taken following a course of daily miricorilant or placebo administration were assessed by magnetic resonance imaging-proton density fat fraction (MRI-PDFF). Additionally, effects of miricorilant may be assessed by measuring one or more of the be measured to assess the effects of miricorilant. Change in blood pressure may be measured in patients with high blood pressure to assess the effects of miricorilant. Pharmacokinetic (PK) parameters were estimated from steady state plasma concentrations of miricorilant.

Other endpoints monitoring and assessment for safety for all study participants. Safety endpoints included the incidence of TEAEs, AEs, and SAEs; changes from Baseline in clinical laboratory tests (hematology and chemistry panels); changes from Baseline in physical examinations and vital sign measurements; changes from Baseline in ECG parameters.

The study drug was a miricorilant tablet (containing 150 mg miricorilant) or a placebo for the 150 mg miricorilant tablet. The study drug, including packaging and storage, is described in Table 1.

TABLE 1

Study Drug: Description, Packaging, and Storage

| Specifications | Miricorilant | Placebo |
|---|---|---|
| Description | Miricorilant tablet, 150 mg is oval shaped and white to off-white in color. Each tablet contains 150 mg of miricorilant and the following inactive ingredients: methacrylic acid-methyl methacrylate copolymer, sodium lauryl sulfate, hypromellose acetate succinate, microcrystalline cellulose, croscarmellose sodium, silicon dioxide, and magnesium stearate. | Placebo for miricorilant tablet, 150 mg is designed to match the study drug in appearance. It is oval shaped and is white to off-white in color. Each tablet contains microcrystalline cellulose. |
| Unit Dose Strength | Miricorilant tablet, 150 mg | Placebo for miricorilant tablet, 150 mg |
| Dose levels | 600 mg and 900 mg | N/A |
| Missed doses | If the patient remembers they missed a dose within 12 hours of their normally scheduled dosing time, then they should take their daily dose of study drug and then resume normal schedule | If the patient remembers they missed a dose within 12 hours of their normally scheduled dosing time, then they should take their daily dose of study drug and then resume normal schedule |
| Storage | Store as follows: In a secure location At 20° C.-25° C. (68° F.-77° F.), excursions permitted to 15° C.-30° C. (59° F.-86° F.) Out of sight and reach of children | Store as follows: In a secure location At 20° C.-25° C. (68° F.-77° F.), excursions permitted to 15° C.-30° C. (59° F.-86° F.) Out of sight and reach of children | following, either by comparing change from baseline after one or more days of miricorilant administration, or by comparing measurements in patients administered miricorilant versus patients administered placebo: change in liver fat assessed by MRI-PDFF; change in AST, ALT, and gamma-glutamyl transferase (GGT); change in propeptide of type III collagen (pro-C3); change in enhanced liver fibrosis (ELF) score and its components (hyaluronic acid, tissue inhibitor of metalloproteinases-1 [TIMP-1], type III procollagen [PII-INP]); change in ACTH, serum cortisol, and serum aldosterone (pharmacodynamic assessments); change in Homeostatic Model Assessment of Insulin Resistance (HOMA-IR); change in absolute body weight; and other measurements. In particular, MRI-PDFF assessments of a change in liver fat may include: the proportion of patients achieving a relative reduction in liver fat of greater than or equal to 30% as assessed by MRI-PDFF for miricorilant versus placebo; the proportion of patients achieving a relative reduction in liver fat of greater than or equal to 50% as assessed by MRI-PDFF for miricorilant versus placebo; the absolute change in liver fat as assessed by MRI-PDFF for miricorilant versus placebo; and the proportion of patients with complete resolution of fatty liver disease as assessed by MRI-PDFF for miricorilant versus placebo. For patients with diabetes, change in HbA1c and change in fasting blood glucose may Administration of Study Drug Patients were randomized in a 1:1:1 ratio to 600 mg miricorilant, 900 mg miricorilant, or placebo. Study drug was administered once daily, orally with 8 oz (240 mL) of water, along with food. Patients were instructed to take a total of 6 tablets at approximately the same time each day. Those in the 600 miricorilant group took 4 miricorilant tablets and 2 placebo tablets. Those in the 900 miricorilant group took 6 miricorilant tablets. Those in the placebo group took 6 placebo tablets. For the week 6 visit, patients were instructed to not take their daily study drug prior to the visit, but to bring their study drug to the site with them so that the study drug can be administered at the site.

Magnetic Resonance Imaging-Derived Proton Density Fat Fraction

Recent data support the use of MRI-PDFF in early-phase NASH clinical trials, as a noninvasive, quantitative measure of the level of fat in the liver (Caussy et al. 2018). Changes in liver fat greater than 30% are correlated with improvements in liver fibrosis by biopsy (Patel et al. 2016). MRI-PDFF was performed to determine the degree of LFC reduction. Instructions for preparing for and performing the test were provided in the study manual.

NASH Biomarkers

NASH biomarkers include AST, ALT, GGT, pro-C3, ELF score and its components (hyaluronic acid, TIMP-1, PII- INP). Blood for measuring levels of AST, ALT, and GGT (as part of the chemistry panel) will be collected. Small fragments of collagen, called propeptides, are released during fibrosis. Pro-C3 is the propeptide of type III collagen and detection of pro-C3 is anticipated to reflect the formation of new fibrotic tissue in the liver (Vilar-Gomez and Chalasani 2018). Blood samples for measuring pro-C3 were collected. The ELF score combines 3 serum biomarkers (hyaluronic acid, TIMP-1, and PIIINP) which have been shown to received 900 mg miricorilant per day, and 2 patients were administered 600 mg miricorilant per day) and 2 patients were administered matching placebo. The 12 enrolled patients had the following baseline values: mean BMI of 38.69±5.3, mean AST of 29.9±9.7 U/L, and mean ALT of 44.9±16.9 U/L.

Further baseline characteristics of these patients are provided in Table 2 below:

TABLE 2

| | Miricorilant, 600 mg (N = 5) | Miricorilant, 900 mg (N = 3) | Placebo (N = 4) | Overall (N = 12) |
|---|---|---|---|---|
| Age (years), median (Q1, Q3) | 58.0 (51.0, 67.0) | 61.0 (39.0, 67.0) | 43.5 (32.0, 54.5) | 54.5 (39.0, 64.0) |
| Female, n (%) | 2 (40.0%) | 2 (66.7%) | 2 (50.0%) | 6 (50.0%) |
| Weight (kg), mean (SD) | 103.0 (14.72) | 107.7 (33.71) | 111.5 (18.71) | 107.0 (19.89) |
| BMI (kg/m$^2$), mean (SD) | 37.4 (4.44) | 39.6 (7.98) | 39.3 (5.51) | 38.6 (5.30) |
| Liver fat (%), mean (SD) | 15.7 (6.54) | 24.6 (6.04) | 19.9 (8.75) | 19.3 (7.53) |
| NASH biomarkers | | | | |
| ALT (U/L), mean (SD) | 33.2 (15.94) | 52.3 (15.63) | 54.0 (12.11) | 44.9 (16.86) |
| AST (U/L), mean (SD) | 25.6 (12.76) | 35.7 (8.14) | 31.0 (4.08) | 29.9 (9.68) |
| GGT (IU/L), mean (SD) | 59.0 (50.29) | 52.7 (19.63) | 59.0 (50.29) | 43.8 (32.20) |
| Lipids | | | | |
| HDL (mmol/L), mean (SD) | 0.92 (0.150) | 1.43 (0.273) | 1.00 (0.184) | 1.07 (0.279) |
| Triglycerides (mmol/L), mean (SD) | 1.79 (0.793) | 1.17 (0.145) | 1.72 (0.673) | 1.61 (0.653) |
| Cholesterol (mmol/L), mean (SD) | 4.67 (1.224) | 5.74 (0.756) | 4.35 (0.897) | 4.83 (1.091) |
| HbA1c (Hb Fraction), mean (SD) | 0.06 (0.013) | 0.06 (0.014) | 0.05 (0.006) | 0.06 (0.011) |
| Insulin (mIU/L), mean (SD) | 23.2 (7.61) | 63.5 (7.71) | 43.5 (19.80) | 40.0 (20.56) | correlate with the degree of liver fibrosis assessed by liver biopsy (Vilar-Gomez and Chalasani 2018). Each of these markers is measured by an immunoassay and an ELF score is generated, from which a level of fibrosis severity can be determined.

Glycated Hemoglobin (HbA1c)

Blood samples were collected from all patients to measure HbA1c, a glycoprotein whose concentration reflects the amount of glucose bound to hemoglobin (Bala et al. 2017).

FibroScan

FibroScan is a specialized ultrasound machine that is used to measure both liver fibrosis and steatosis (Afdhal 2012). FibroScan were performed at Screening (recent liver biopsy or scans performed 3 months within Screening were also acceptable). Instructions for preparing for and performing the test were provided in the study manual.

The present Example 1 is based on results from the first 12 patients of this study (n=5 received 600 mg miricorilant, n=3 received 900 mg miricorilant, and n=4 received placebo), 7 of whom had liver fat measured both at baseline and after at least 30 days on the study drug. Although presumed to have NASH, none of these patients exhibited characteristics indicative of severe risk of hepatocellular injury ("Hy's law": total bilirubin greater than twice the upper limit of normal (ULN) for bilirubin, and liver enzyme (ALT or AST) levels greater than three times the ULN for those enzymes). Only 7 of the original 12 enrolled patients completed post-treatment MRI-PDFF measurements. Of these 7 patients, 5 were administered miricorilant (3 patients Of these 12 initial patients, 7 were administered miricorilant or placebo for 4 weeks or more; 4 of the 5 patients administered miricorilant exhibited large decreases in liver fat content ranging from a 38.5% reduction to a 73.8% reduction compared to the patient's baseline liver fat content (as measured by MI-PDFF). The MIRI-PDFF values underlying these percentages ranged from reductions of 9.3 to 13.3 as compared to the patient's baseline MRI-PDFF value. The MRI-PDFF measurements in one patient, taken 26 days after cessation of the study drug (600 mg miricorilant per day), showed an increase, as compared to baseline, of 27.9% in liver fat (MRI PDFF value increase of 5 as compared to baseline).

Figure 3A:
FIG. 3A presents a magnetic resonance imaging (MRI) scan showing the liver of a patient who received 600 mg miricorilant per day. The left-hand images were taken before miricorilant treatment. The right-hand images were taken following miricorilant treatment. The upper images are in-phase and the lower images are opposed phase MRI images.
Figure 3C:
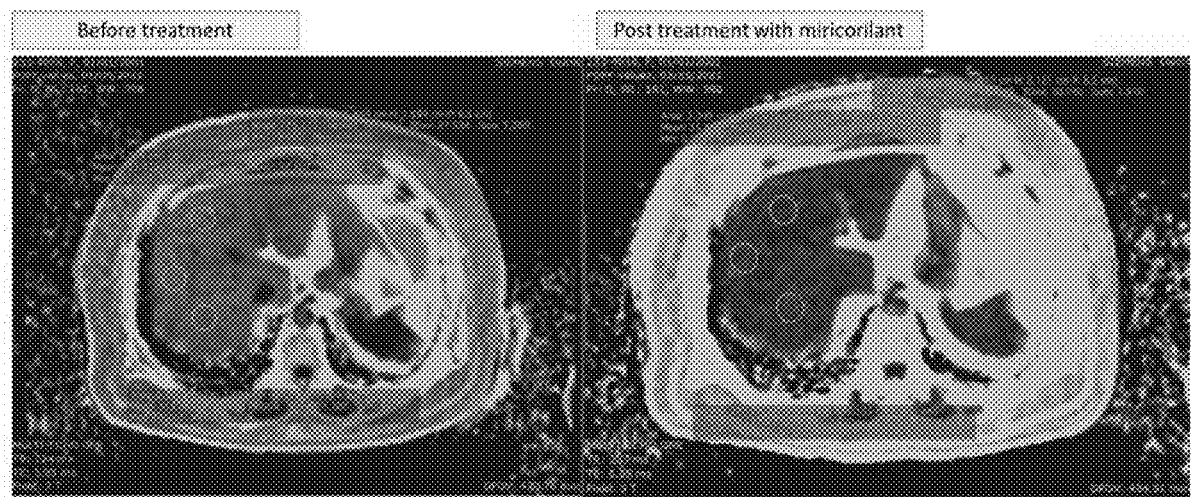
FIG. 3C presents a magnetic resonance imaging (MRI) scan showing the liver of the same patient shown in 3A and 3B, which demonstrates the dramatic reduction in liver fat content in the patient following miricorilant treatment.

These MRI-PDFF results regarding liver fat are shown in the following table. MRI images showing the liver of a patient before (left-hand images) and after receiving daily 600 mg miricorilant (right-hand images) are presented in FIGS. 3A, 3B, and 3C. As shown in FIG. 3B, the size of the patient's liver was measured as 130.90 millimeters (mm) by 194.47 mm before treatment (Jan. 8, 2021); and was reduced to 120.95 mm by 183.02 mm after treatment with miricorilant (Mar. 15, 2021). As shown in FIG. 3C, the liver fat content in the patient experiencing the greatest reduction in liver fat content was reduced from a mean liver fat content of 12.6% at baseline to a mean liver fat content of 3.3% after treatment with miricorilant.

MRI-PDFF has been used as a noninvasive, quantitative measure of the level of fat in the liver (Caussy et al., Hepatology 68(2):763-772 (2018)). This MRI technique acquires multiple echoes at times where the fat and water echoes are in phase or are out of phase with each other, providing images that illustrate fat distribution and quantity across the liver (Patel et al., Therap Adv Gastroent 9(5): 692-701 (2016)). As indicated, FIGS. 3A, 3B, and 3C include both "In phase" and "Opposed phase" MRI images. Changes in liver fat content greater than 30% are correlated with improvements in liver fibrosis by biopsy (Patel et al., 2016). As shown in Table 3, liver fat reductions greater than 30% were found in four patients.

TABLE 3

| | | | | | | MRI Days | Screening MRI | | | |
|---|---|---|---|---|---|---|---|---|---|---|
| | | Study Drug Start Date/ | Days on Study | Study Day of | Days after dose | PDFF | MRI PDFF | Change in MRI | % Change |
| Patient ID | Dose | End Date | Drug | MRI | ended | value | value | PDFF | in liver fat |
| 208-4020 | 900 mg | 28 Jan. 2021/ 26 Feb. 2021 | 30 | 49 | 19 | 17.6 | 6.1 | −11.5 | −65.3% |
| 211-4002 | 900 mg | 14 Dec. 2020/ 13 Jan. 2021 | 31 | 95 | 64 | 27.8 | 17.1 | −10.7 | −38.5% |
| 214-4007 | 900 mg | 11 Jan. 2021/ 23 Feb. 2021 | 44 | 60 | 16 | 28.3 | 15.0 | −13.3 | −47.0% |
| 233-4018 | 600 mg | 20 Jan. 2021/ 22 Feb. 2021 | 34 | 55 | 21 | 12.6 | 3.3 | −9.3 | −73.8% |
| 232-4016 | 600 mg | 26 Jan. 2021/ 5 Mar. 2021 | 39 | 65 | 26 | 17.9 | 22.9 | 5.0 | +27.9% |
| 211-4011 | Placebo | 30 Dec. 2020/ 6 Mar. 2021 | 67 | 79 | 12 | 10.7 | 10.8 | 0.1 | +0.9% |
| 214-4005 | Placebo | 6 Jan. 2021/ 5 Mar. 2021 | 59 | 70 | 11 | 27.6 | 29.9 | 2.3 | +8.3% |

Liver volume changes in the four patients who responded to miricorilant treatment are presented in Table 4:

TABLE 4

| Change in Liver Volume in Responders | | | | |
|---|---|---|---|---|
| | Dose (mg) | Baseline Liver Volume (mL) | Follow-Up Liver Volume (mL) | Percent Change from Baseline in Liver (%) |
| Patient 1 | 900 | 1606 | 1303 | −18.9 |
| Patient 2 | 900 | 1675 | 1314 | −21.6 |
| Patient 3 | 900 | 3857 | 3113 | −19.3 |
| Patient 4 | 600 | 1899 | 1505 | −20.7 |

Figure 4:
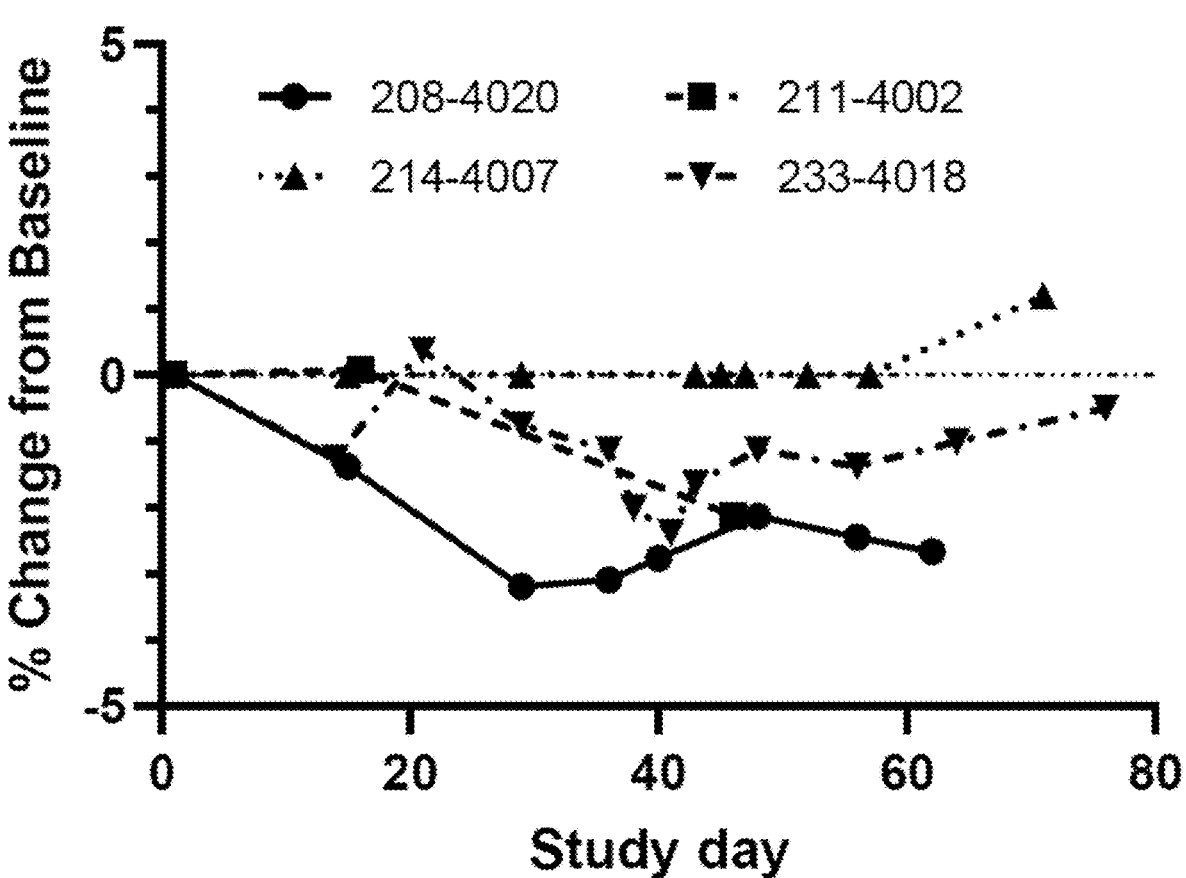
FIG. 4 shows body weight changes in patients who responded to miricorilant.
Figure 5:
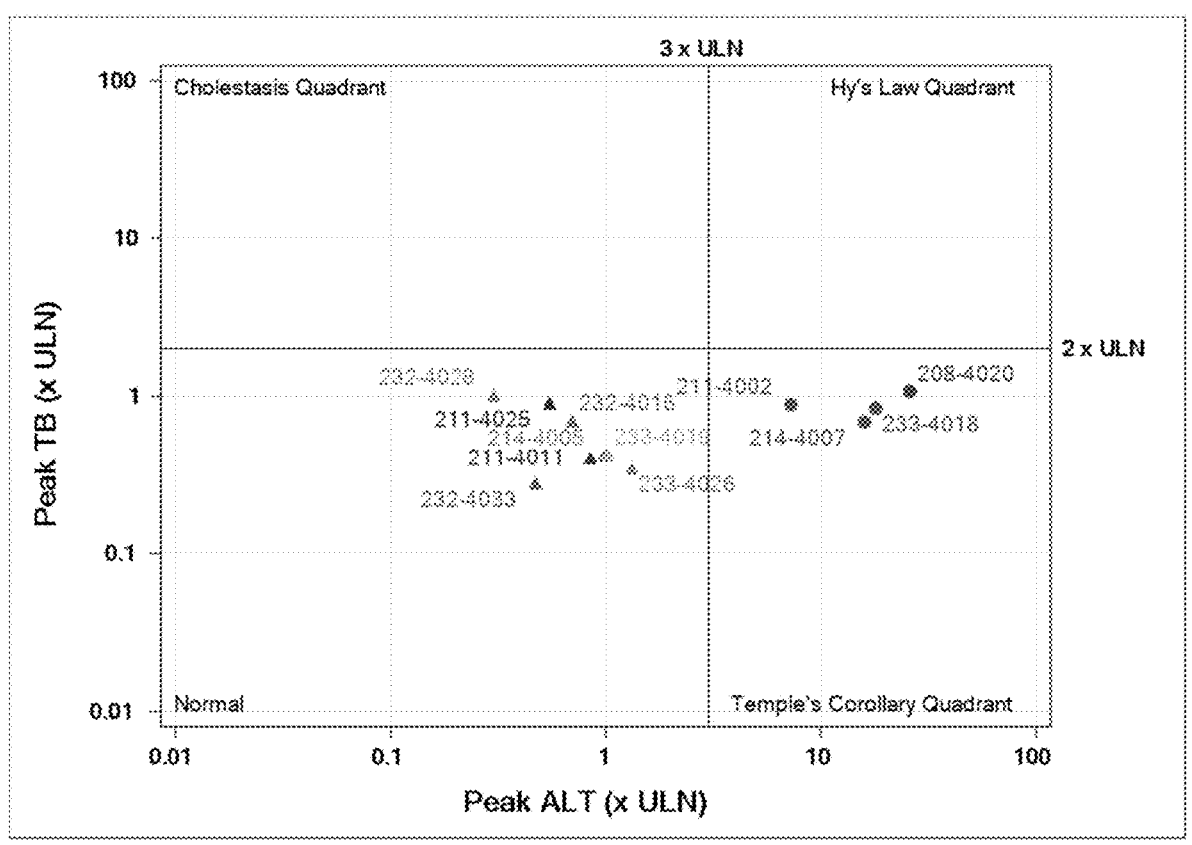
FIG. 5 presents an eDISH (evaluation of Drug-Induced Serious Hepatotoxicity) plot of peak values of patient total bilrubin (vertical axis) verusus liver alanine amino transferase (ALT) levels in 12 subjects. The plot includes a horizontal line within the graph indicating the level that is twice the total bilirubin upper limit of normal (ULN), and includes a vertical line within the graph showing the level that is three times the ALT ULN.

Body weight changes in the patients who responded to miricorilant treatment are shown in FIG. 4. No significant changes in body weight were observed.

Figure 2A:
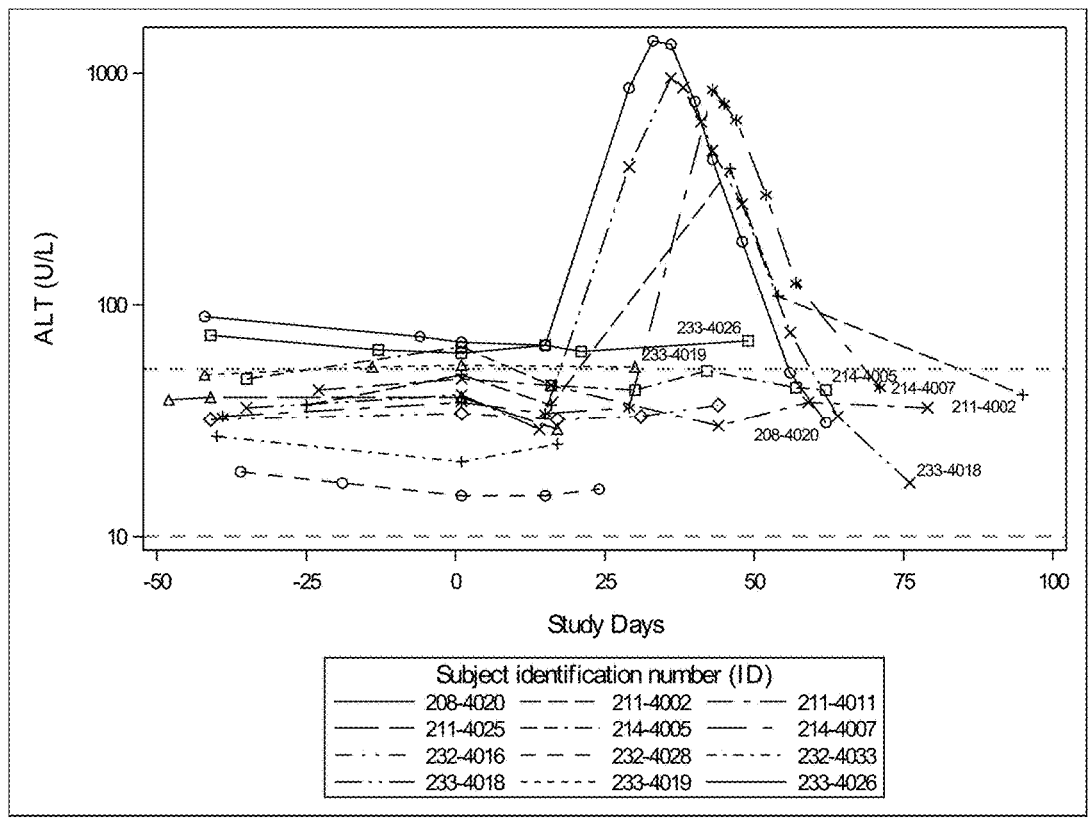
FIG. 2A shows initial liver alanine amino transferase (ALT) levels in 12 subjects, and in 7 subjects over time before, during, and after miricorilant or placebo administration. The dashed lines indicate the upper and lower limits of normal ALT levels.
Figure 2B:
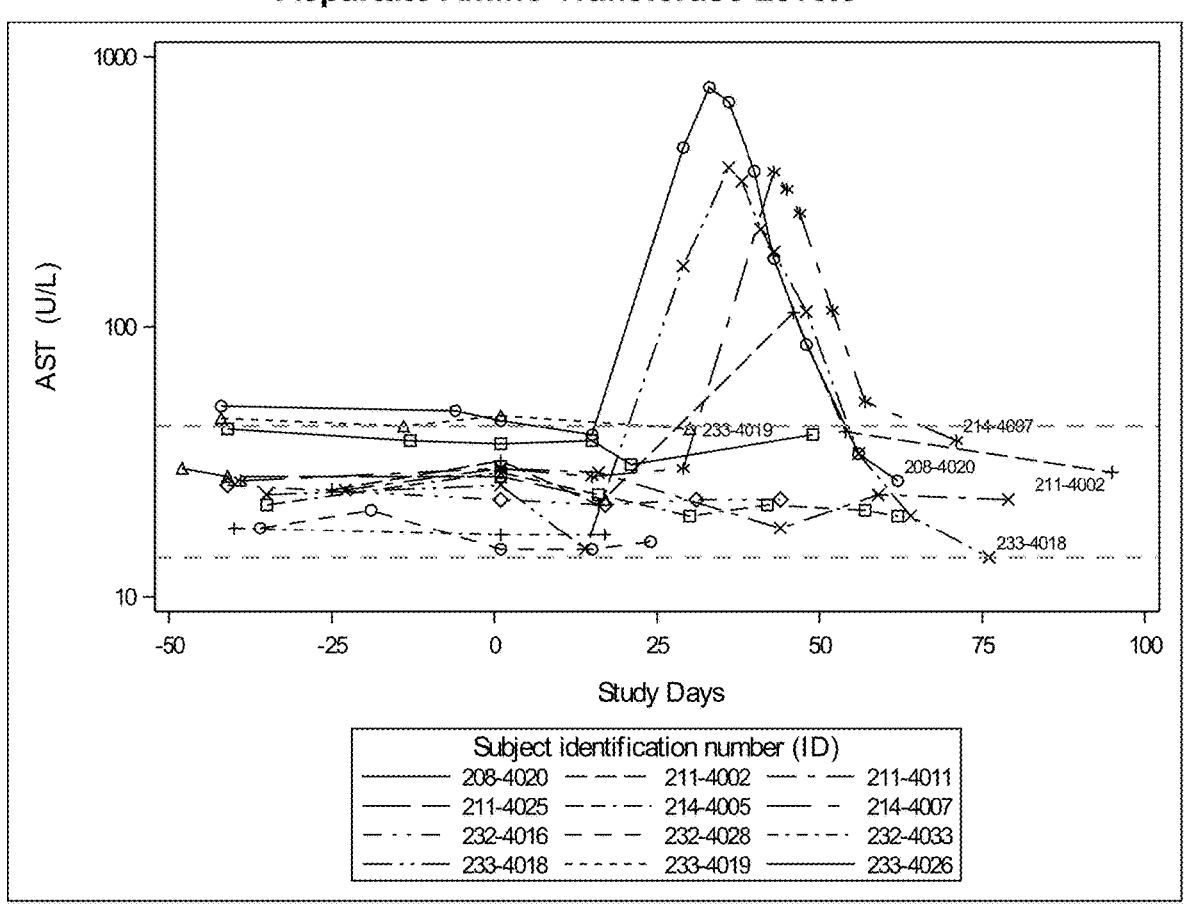
FIG. 2B shows initial liver aspartate amino transferase (AST) levels in 12 subjects, and in 7 subjects over time before, during, and after miricorilant or placebo administration. The dashed lines indicate the upper and lower limits of normal AST levels.
Figures 2C, 2D, 2E, 2F, 2G, 2H, 2I:
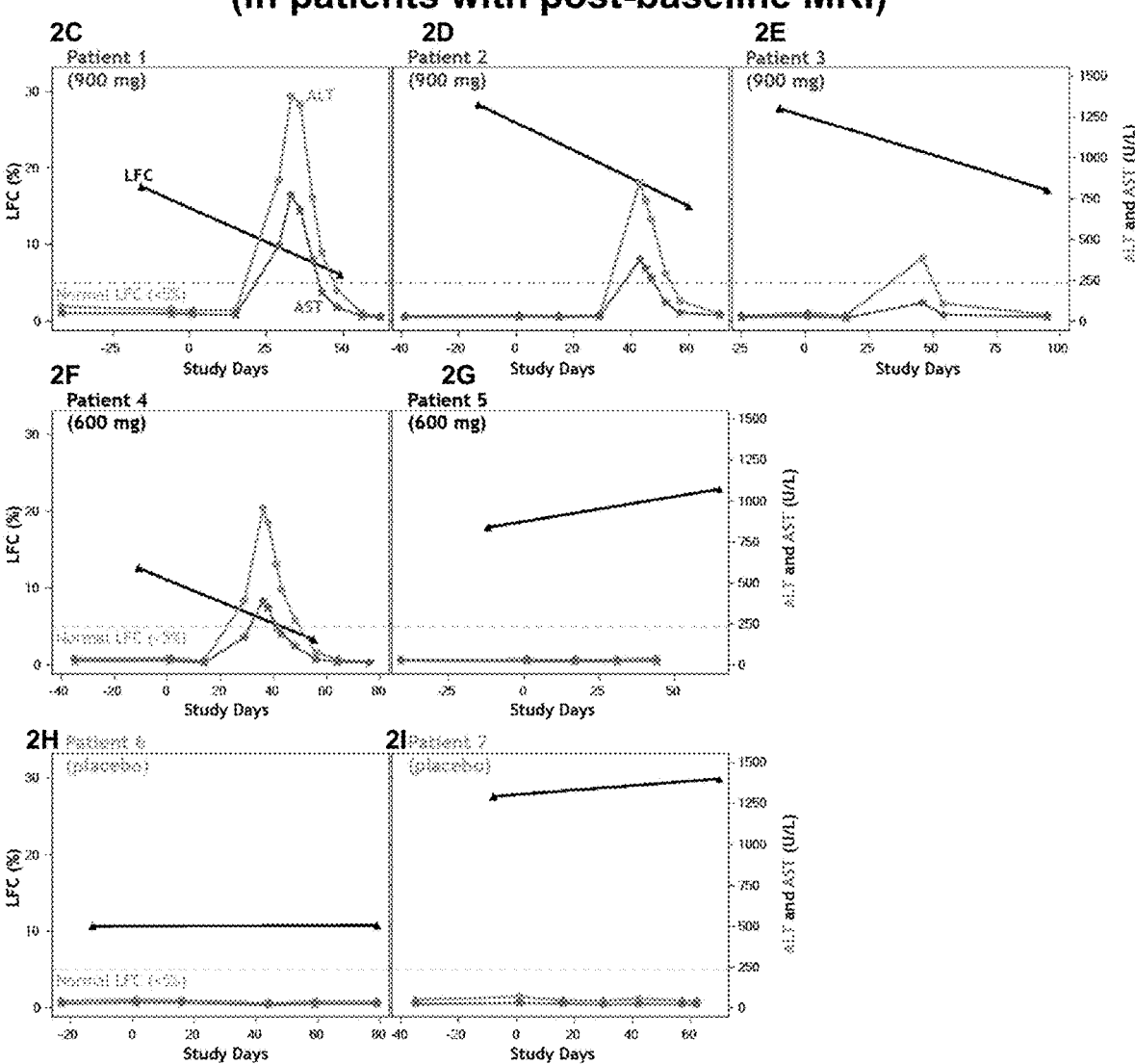
FIG. 2C shows the timecourse of liver fat, alanine amino transferase (ALT), and aspartate amino transferase (AST) levels in subject Patient 1 over time before, during, and after administration of 900 milligrams per day (mg/day) miricorilant.
FIG. 2D shows the timecourse of liver fat, ALT, and AST levels in subject Patient 2 over time before, during, and after administration of 900 mg/day miricorilant.
FIG. 2E shows the timecourse of liver fat, ALT, and AST levels in subject Patient 3 over time before, during, and after administration of 900 mg/day miricorilant.
FIG. 2F shows the timecourse of liver fat, ALT, and AST levels in subject Patient 4 over time before, during, and after administration of 600 mg/day miricorilant.
FIG. 2G shows the timecourse of liver fat, ALT, and AST levels in subject Patient 5 over time before, during, and after administration of 600 mg/day miricorilant.
FIG. 2H shows the timecourse of liver fat, ALT, and AST levels in subject Patient 6 over time before, during, and after placebo administration.
FIG. 2I shows the timecourse of liver fat, ALT, and AST levels in subject Patient 7 over time before, during, and after placebo administration.

Liver enzyme levels were measured in the patients. ALT and AST level measurements are shown in FIGS. 2A and 2B. No significant changes in plasma triglyceride or cholesterol levels were noted in patients receiving miricorilant.

Plots of liver enzyme levels and liver fat content are shown in FIGS. 2C-21 for each individual patient who was in the study through to receiving post-baseline MRI measurements (1 through 7).

A table presenting liver enzyme levels as well as liver fat content (per MRI-PDFF measurements) in those patients who exhibited liver fat content decreases is presented below.

TABLE 4

| | | | | | AST | | ALT | | Liver fat (%) | | Relative change from |
|---|---|---|---|---|---|---|---|---|---|---|---|
| | Dose | Age | | Days on | (U/L) | | (U/L) | | | Follow- | baseline in |
| PATIENT | (mg) | (yrs) | Sex | treatment | Baseline | Max | Baseline | Max | Baseline | up | % liver fat |
| (233-4018) | 600 | 58 | F | 34 | 26 | 391 | 41 | 955 | 12.6 | 3.3* | −73.8 |
| (208-4020) | 900 | 61 | F | 30 | 45 | 772 | 69 | 1378 | 17.6 | 6.1 | −65.3 |
| (214-4007) | 900 | 67 | F | 44 | 30 | 376 | 38 | 848 | 28.3 | 15.0 | −47.0 |
| (211-4002) | 900 | 39 | M | 31 | 32 | 113 | 50 | 386 | 27.8 | 17.1 | −38.5 |

*complete resolution of fatty liver (MRI-PDFF <5%)

Bilirubin and liver enzyme levels were measured in the patients at baseline. These results are presented in FIG. 5 as an "eDISH plot" (evaluation of Drug-Induced Serious Hepatotoxicity; see, e.g., Merz et al., Drug Saf (2014) 37 (Suppl 1):S33-S45) in which the vertical axis shows the peak total bilirubin (as multiple of ULN total bilirubin levels) and in which the horizontal axis shows the peak ALT (as multiple of ULN ALT levels). Bilirubin and ALT levels that combined are placed in the upper right quadrant of the graph, labelled "Hy's Law Quadrant", indicate that the patient is at high risk of severe hepatocellular injury. The cholestasis quadrant is the location on the graph where bilirubin levels are greater than twice the ULN for bilirubin. The "Temple's Corollary" quadrant is the location on the graph where peak ALT levels are greater than 3 times the ULN for ALT, but bilirubin levels are less than twice the ULN for bilirubin. No patient in this study satisfied the criteria for Hy's Law; thus, by these criteria, the treatment did not lead to a high risk of severe hepatocellular injury.

These results show that miricorilant administration can result in large decreases in liver fat in presumed NASH patients; these decreases were rapid. One patient (of the four experiencing liver fat decreases) experienced a complete resolution of fatty liver. These rapid and large reductions in liver fat were independent of changes in weight (weight changes ranged from −3.2% to +1.2% of baseline body weight for these four patients) and other metabolic parameters.

Further measurements of other biomarkers which may be indicative of NASH are presented in Table 5. (Units are nanograms per milliliter (ng/mL) except for the enhanced liver fibrosis score (ELF), which is unitless.)

Two studies were conducted in C57BL/6J male mice (n=12 per group) maintained on a diet high in fat (40%), cholesterol (2%) and fructose (20%; referred to as the AMLN diet: see, e.g., Tolbol et al., World Journal of Gastroenterology, 24(2):179-194 (2018)) for 42 weeks before dosing with miricorilant was initiated. In the first study, all animals ate the AMLN diet, and received either placebo, 30 mg/kg miricorilant, or 60 mg/kg mifepristone once per day orally. In the second study, all animals received the high-fat diet; control animals did not receive miricorilant, while study animals received 60 mg/kg miricorilant or 60 g/kg mifepristone in their high-fat diet, which they ate ad libitum. All animals received the AMLN diet for 42 weeks prior to receiving their first dose of study drug or placebo. 4 weeks prior to receiving that first dose, a liver biopsy and histological examination of biopsy tissue was performed for each animal; 3 weeks prior to receiving that first dose, animals were randomized into three groups: control, miricorilant, or mifepristone. Only mice with fibrosis stage >=1 and steatosis score >=2 were allowed in the study and the groups were stratified according to liver col1a1 so that each study group had similar overall distributions of liver col1a1 among the mice. All animals continued on the study diet for the 3 weeks following randomization, at which time study drug or placebo administration began. All animals received their assigned drugs for 8 weeks (the 8 week in vivo study period). At 56 days (week 8) after initiation of drug administration, plasma ALT, AST, triglycerides, total cholesterol, and miricorilant levels were measured, and animals were sacrificed, liver necropsies were performed, liver histological ((NAFLD Activity Score, Fibrosis Stage, steatosis (scored using hematoxylin and eosin staining (HE)), col1a

TABLE 5

| | 900 mg Miricorilant (N = 3) | | 600 mg Miricorilant (N = 5) | | Placebo (N = 4) | |
|---|---|---|---|---|---|---|
| | Value mean (SD) | Change from Baseline mean (SD) | Value mean (SD) | Change from Baseline mean (SD) | Value mean (SD) | Change from Baseline mean (SD) |
| Propeptide of Type III Collagen (pro-C3) (ng/mL) | 24.1 (13.8) | −7.9 (9.29) | 10.7 (3.43) | 0.5 (3.05) | 12.7 (2.04) | 1.1 (2.71) |
| Enhanced Liver Fibrosis (ELF) Score | 10.6 (1.03) | −0.90 (0.081) | 9.4 (0.99) | −0.05 (0.634) | 9.6 (0.61) | −0.22 (0.412) |
| Hyaluronic Acid (ng/mL) | 110.9 (68.23) | −50.0 (29.20) | 70.7 (72.86) | −17.8 (43.16) | 62.5 (37.45) | −5.6 (36.71) |
| Tissue Inhibitor of Metalloproteinases-1 (TIMP-1) (ng/mL) | 402.1 (95.07) | −79.4 (85.21) | 249.5 (31.85) | 3.2 (22.51) | 222.8 (37.21) | 3.6 (20.74) |
| Type III Procollagen (PIIINP) (ng/mL) | 17.7 (8.18) | −5.35 (3.573) | 9.3 (1.84) | −0.17 (3.215) | 10.7 (1.15) | 0.06 (1.396) |

Example 2

Male C57 mice (n=24) were given a diet containing 6000 fat (a high-fat, "fast food" diet) for 3 weeks. Miricorilant (60 mg/kg) was administered once a day via oral gavage. Plasma aspartate aminotransferase (AST) was measured on days 3, 7, 12, and 18 and 6 mice were sacrificed each week at weeks 1, 2, and 3 for the miricorilant groups and at week 3 for the control (high-fat diet, no miricorilant) group for assessment of liver triglycerides. As shown in FIG. 6A, mice on a high-fat diet, daily dosing of miricorilant led to a rapid reduction in liver triglycerides starting at week 1. As shown in FIG. 6B, AST showed a transient increase at 2 weeks but normalized by 3 weeks without a change in miricorilant dose.

(scored using immunohistochemistry (IHC)) and Galectin-3 (IHC)) and liver biochemical measurements (including liver triglycerides and total cholesterol) were made, and liver and plasma samples were obtained for genetic ((e.g., RNA sequencing) and other analyses.

Thus, in these studies, the mice were subjected to a liver biopsy approximately 4 weeks before initiation of dosing with miricorilant and only mice with confirmed fibrosis (fibrosis stage ≥1) and steatosis (score ≥2) were entered into the study. At the end of the dosing period, blood samples were collected for determination of plasma ALT, AST, triglycerides, total cholesterol, and miricorilant. Liver samples were collected for analysis of triglycerides, total cholesterol, hydroxyproline, and histopathology. Body weight and food consumption were monitored throughout the study. Both studies included a control group that received the AMLN diet but did not receive miricorilant. One study in mice using an AMLN NASH model showed that miricorilant reduced non-alcoholic fatty liver disease (NAFLD) activity score (NAS) as compared to control; a further AMLN NASH mouse model study showed that miricorilant reduced body weight, liver weight, liver collagen, and liver galectin-3 content as compared to control.

Once Per Day Oral Miricorilant

Mice receiving daily oral miricorilant showed significant reductions in NAFLD Activity Score (NAS) as compared to control.

Liver samples were fixed in formalin, paraffin embedded and sections were stained with hematoxylin and eosin (H&E) and Sirius Red. Samples were scored for NAS and fibrosis stage using the clinical criteria outlined by Kleiner et al., Hepatology 41:1313-1321 (2005).

Hematoxylin & Eosin (H&E) staining The slides were incubated in Mayer's Hematoxylin (Dako), washed in tap water, stained in Eosin Y solution (Sigma-Aldrich), hydrated, mounted with Pertex and then allowed to dry before scanning.

Sirius red staining The slides were incubated in Weigert's iron hematoxylin (Sigma-Aldrich), washed in tap water, stained in Picro-sirius red (Sigma-Aldrich) and washed twice in acidified water. Excess water was removed by shaking the slides and the slides were then hydrated in three changes of 100% ethanol, cleared in xylene and mounted with Pertex and allowed to dry before scanning.
Total Non-Alcoholic Fatty Liver Disease Activity Score (NAS)

Total NAS score represents the sum of scores for steatosis, inflammation, and hepatic ballooning, and ranges from 0-8. Steatosis score refers to amount of surface area of stained tissue samples involved by steatosis as evaluated on low to medium power examination. Inflammation was evaluated by counting the number of inflammatory foci per field using a 200× magnification (minimum 5 fields per animal). A focus was defined as a cluster, not a row, of greater than 3 inflammatory cells. Acidophil bodies were not included in this assessment, nor was portal inflammation. Hepatocellular ballooning degeneration was scored from stained tissue samples; degenerated hepatocytes exhibit one or more of a cleared cytoplasm, enlargement, swelling, rounding and reticulated cytoplasm.

Figure 7A:
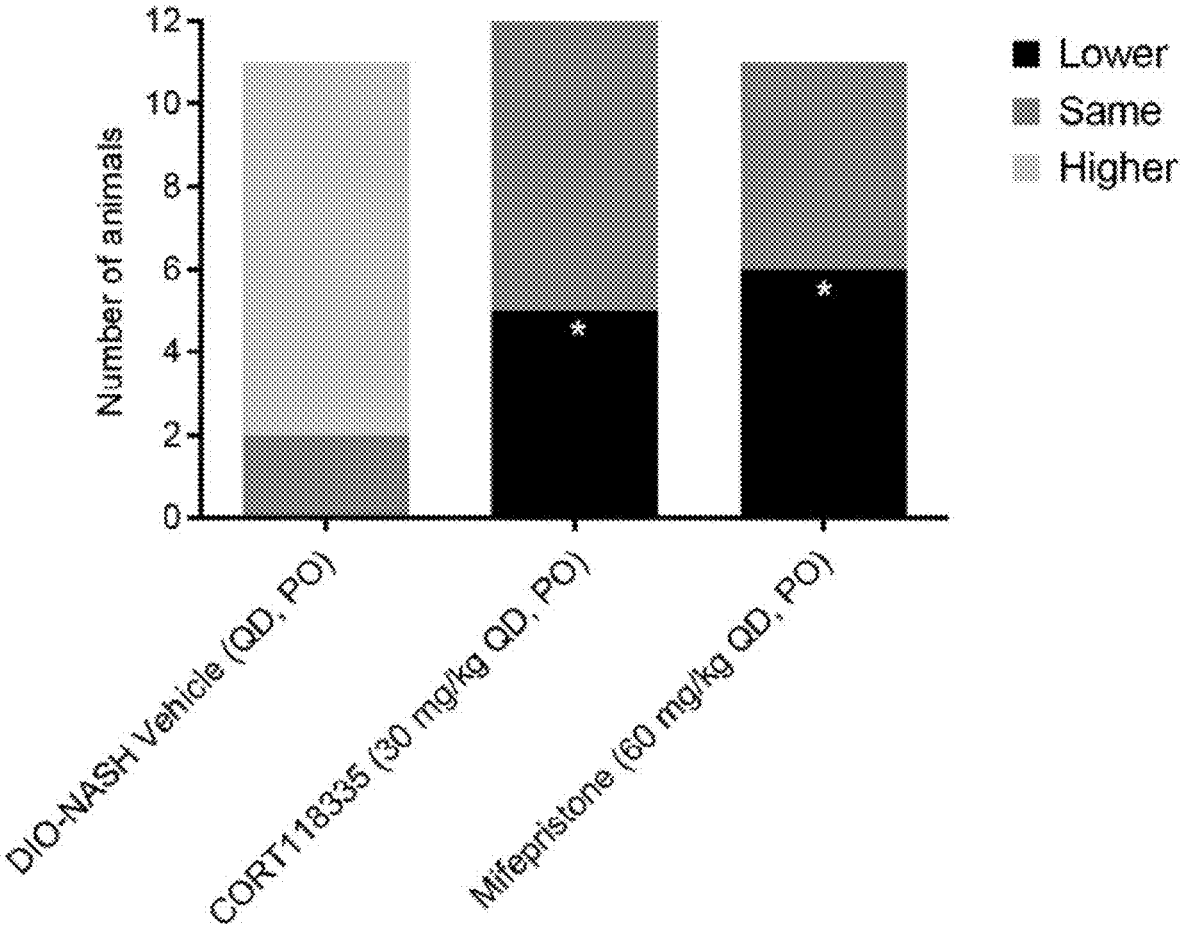
FIG. 7A presents non-alcoholic fatty liver disease (NAFLD) activity scores for groups of mice receiving AMLN diet; control mice received AMLN diet alone, while study mice received, in addition to the AMLN diet, 30 millgrams per kilogram per day (mg/kg/day) miricorilant orally once per day (center column), or 60 mg/kg/day mifepristone orally once per day (right-most column). The NAFLD activity score increased in mice fed the AMLN diet alone, while the NAFLD activity score either did not increase, or decreased in mice receiving miricorilant while being fed the AMLN diet. (Asterisk indicates significant difference as compared to control.)

FIG. 7A presents NAFLD Activity scores for groups of mice receiving either AMLN diet alone, AMLN diet plus 30 milligrams per kilogram per day (mg/kg/day) miricorilant orally once per day, and AMLN diet plus 60 mg/kg/day mifepristone orally once per day. As shown in FIG. 7A, while the NAFLD activity score increased in mice fed the AMLN diet alone, the NAFLD activity score either did not increase, or decreased in mice receiving miricorilant while being fed the AMLN diet. (Asterisk indicates significant difference as compared to control.)

Figure 7B:
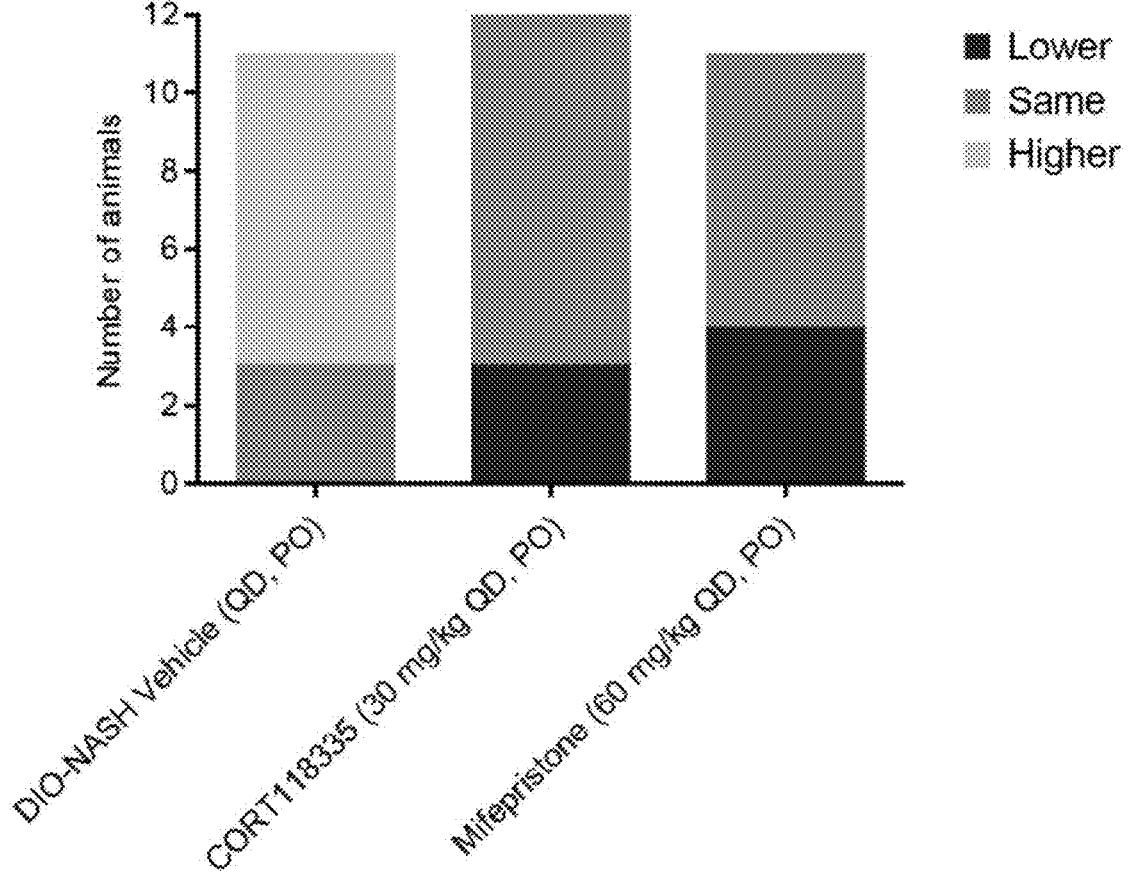
FIG. 7B presents the results of hepatic ballooning scores in livers from the control and study mice (hepatic ballooning is an indication of liver degeneration, and is one of several factors making up the NAFLD Activity Score). These hepatic ballooning scores are based on comparisons of histopathological scoring of the pre- and post-study biopsies. For each group the number of animals with a higher (worsening), same or lower (improvement) in score at post-compared to pre-study is indicated by the height of the bar. Miricorilant reduced the portion of the NAFLD score due to liver cell degeneration as measured by hepatic ballooning.

As noted above, the NAFLD Activity Score is a composite score including values for several factors indicative of fatty liver disorders. One such factor is hepatic ballooning; such measurements are shown in FIG. 7B which provides a summary of histopathological scoring of the pre- and post-study biopsies. For each group the number of animals with a higher (worsening), same or lower (improvement) in score at post-compared to pre-study is indicated by the height of the bar. As shown in FIG. 7B, miricorilant reduced the portion of the NAFLD score due to liver cell degeneration as measured by hepatic ballooning. Unlike any animals in the control group, some mice in the miricorilant group showed decreased post-study fibrosis stage score (as compared to pre-study), and none showed an increased fibrosis stage score.

Miricorilant Provided in the AMLN Diet

Mice receiving miricorilant in their diet (the AMLN diet) showed significantly reduced body weight, reduced liver weight, reduced total liver col1a1 and reduced Galectin-3 content, as compared to the diet-alone (no miricorilant added to the AMLN food) control group.

Type I collagen IHC staining Type I collagen (Southern Biotech, Cat. 1310-01) IHC were performed using standard procedures. Briefly, after antigen retrieval and blocking of endogenous peroxidase activity, slides were incubated with primary antibody. The primary antibody was detected using a polymeric HRP-linker antibody conjugate. Next, the primary antibody was visualized with DAB as chromogen. Finally, sections were counterstained in hematoxylin and cover-slipped.

Liver Galectin-3 content Galectin-3 (Biolegend, Cat. #125402) IHC was performed using standard procedures. Briefly, after antigen retrieval and blocking of endogenous peroxidase activity, slides were incubated with primary antibody. The primary antibody was detected using a linker secondary antibody followed by amplification using a polymeric HRP-linker antibody conjugate. Next, the primary antibody was visualized with DAB as chromogen. Finally, sections were counterstained in hematoxylin and cover-slipped.

Figure 8A:
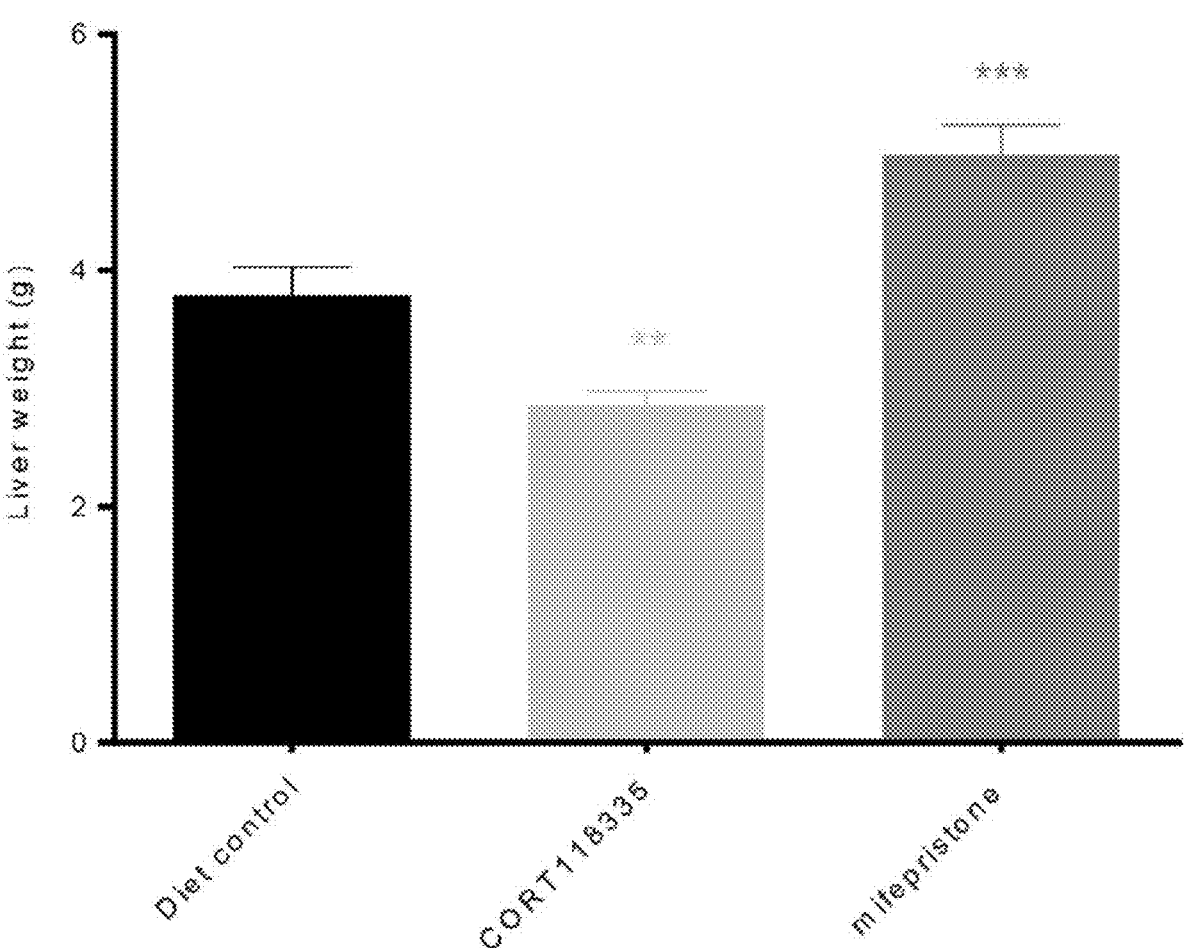
FIG. 8A presents the liver weights (at termination of the study) of mice fed the AMLN diet, mice fed the AMLN diet additionally containing miricorilant, and mice fed the AMLN diet additionally containing mifepristone). Miricorilant significantly reduced liver weight as compared to diet-alone controls.

As shown in FIG. 8A, liver weight was significantly reduced in mice receiving miricorilant in their food as compared to control. FIG. 8A shows total liver weight at termination of the study. Data are expressed as mean±SEM (n=11-12).  $P<0.01$, *$P<0.001$ vs diet-alone control. One-way ANOVA with Dunnett's multiple comparison test (all columns against diet-alone control). Miricorilant significantly reduced liver weight and mifepristone significantly increased liver weight, as compared to diet-alone controls.

Figure 8B:
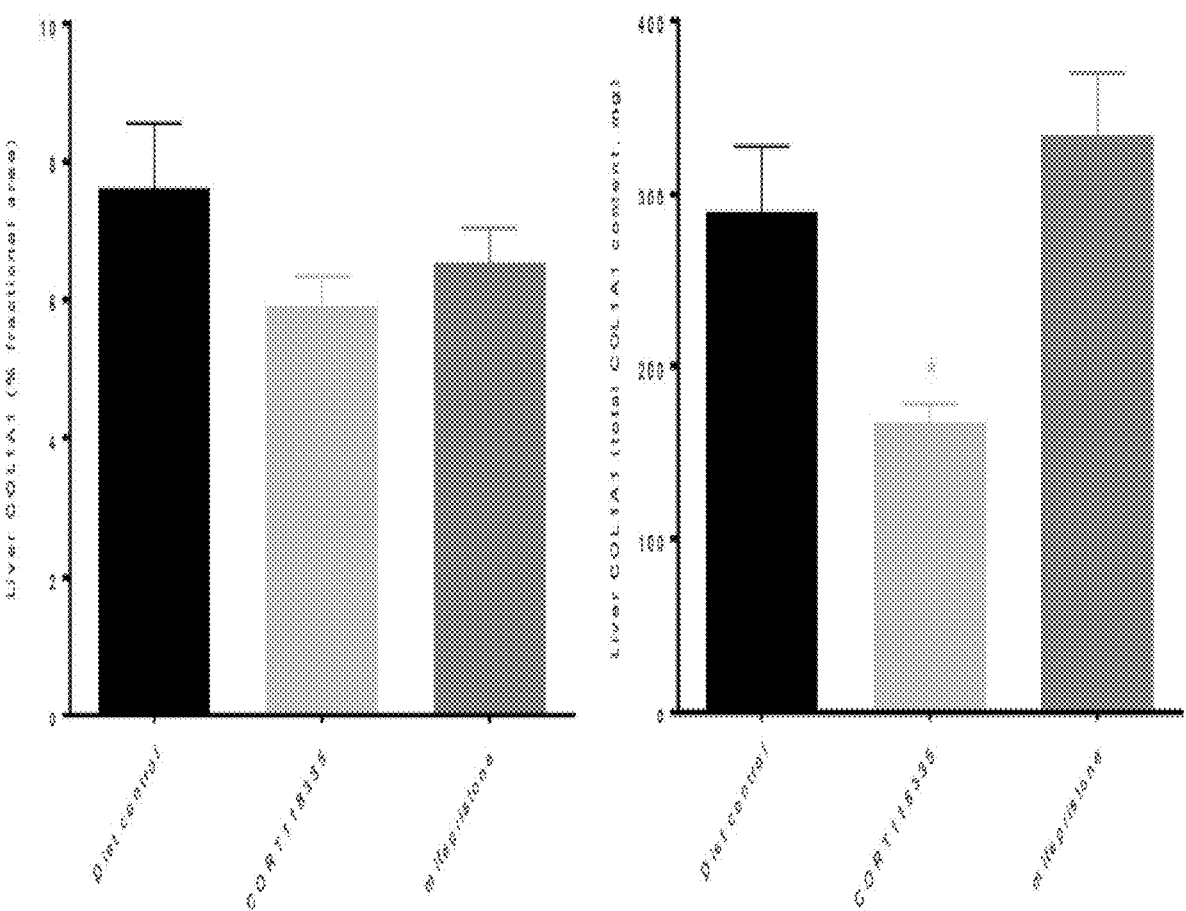
FIG. 8B presents the amounts of type 1 liver collagen (col1a1) of mice fed the AMLN diet, mice fed the AMLN diet additionally containing miricorilant, and mice fed the AMLN diet containing mifepristone. Values were obtained at the termination of the study. Left column: as % of fractional area in samples (relative amounts); right column: as milligrams of total type 1 liver collagen (total amounts). Diet containing miricorilant reduced the total liver col1a1 content, as compared to diet-only (vehicle) controls.

As shown in FIG. 8B, type 1 liver collagen (col1a1) was reduced in livers of mice fed AMLN feed with miricorilant; this difference (as compared to control) was significant when measured as total weight. Total liver col1a1 was evaluated from liver samples stained with anti-type I collagen (col1a1) (Southern Biotech, cat. 1310-01) at the end of the treatment period (typically using low power (20×) magnification). Galectin-3 content was evaluated from images of liver samples stained with anti-Galectin-3 (BioLegend, Cat. 125402) at the end of the treatment period (typically using low power (20×) magnification). Terminal relative (left) and total (right) liver type I Collagen (Col1a1) quantification was determined by morphometry. Data are expressed as mean±SEM (n=11 for treatment groups, n=12 for Vehicle). One-way ANOVA followed by Dunnett's multiple comparisons test. *$p<0.05$ vs. Vehicle. Diet containing miricorilant reduced the total liver col1a1 content, as compared to diet-only (vehicle) controls.

Figure 8C:
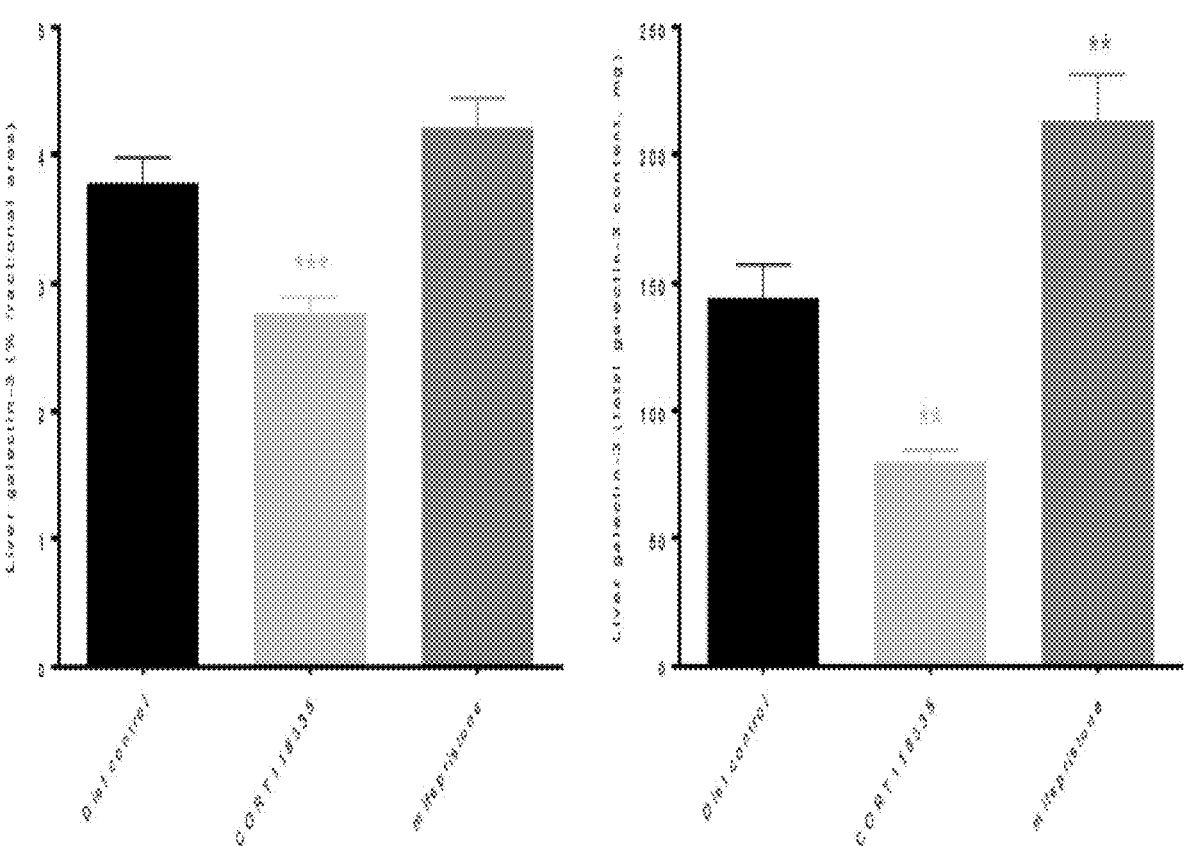
FIG. 8C presents the amounts of liver galectin-3 of mice fed the AMLN diet, mice fed the AMLN diet additionally containing miricorilant, and mice fed the AMLN diet containing mifepristone. Values were obtained at the termination of the study. Miricorilant in the diet reduced relative and total liver Galectin-3 content, as compared to control mice fed a diet without miricorilant ("vehicle"). Left column: as % of fractional area in samples (relative amounts); right column: as milligrams of total type 1 liver collagen (total amounts). Data are expressed as mean±SEM (n=11 for treatment groups, n=12 for Vehicle). One-way ANOVA followed by Dunnett's multiple comparison test. p<0.01 and *p<0.001 vs. Vehicle.

As shown in FIG. 8C, liver galectin-3 was reduced in livers of mice fed AMLN feed with miricorilant. Terminal relative (left) and total (right) liver Galectin-3 was determined by morphometry. Data are expressed as mean±SEM (n=11 for treatment groups, n=12 for Vehicle). One-way ANOVA followed by Dunnett's multiple comparison test. $p<0.01$ and *$p<0.001$ vs. Vehicle. Miricorilant in the diet reduced relative and total liver Galectin-3 content, as compared to control mice fed a diet without miricorilant ("vehicle").

Example 3

A description of a clinical trial for evaluating the clinical benefits and effects of miricorilant treatment administered to patients suffering from non-alcoholic steatohepatitis (NASH) is provided herein. Patients 18 to 75 years of age having a diagnosis of NASH based on a biopsy obtained within the last year, or having a diagnosis of presumed NASH based on blood tests and scans, may be included in the study. The study is designed to assess the safety and efficacy of miricorilant treatment in patients with presumed Nonalcoholic Steatohepatitis (NASH). Patients who meet the criteria for the study are enrolled on Day 1 into 1 of 4 cohorts and receive:

Cohort 1—dose escalation—Patients who meet the entry criteria for the study are enrolled to receive miricorilant escalated every 4 weeks from 150 mg once daily (oral dosing), to 600 mg once daily in 150 mg increments over 16 weeks.

Cohort 2—150 mg miricorilant—Patients who meet the entry criteria for the study are enrolled to receive miricorilant as a steady dose of 150 mg once daily (oral dosing), for up to 12 weeks.

Cohort 3—300 mg miricorilant—Patients who meet the entry criteria for the study are enrolled to receive miricorilant as a steady dose of 300 mg once daily (oral dosing), for up to 12 weeks.

Cohort 4—450 mg miricorilant—Patients who meet the entry criteria for the study are enrolled to receive miricorilant as a steady dose of 450 mg once daily (oral dosing), for up to 12 weeks.

A primary outcome measure for the study is relative change from baseline in liver fat content, assessed by MRI-PDFF compared to baseline (e.g., from baseline day 1 to week 16, or, for as long as the patient is in the study if the patient receives fewer than the scheduled 12 or 16 weeks of treatment). A further outcome measure for the study is relative change from baseline in aspartate aminotransferase (AST) levels, as compared to baseline (e.g., from baseline day 1 to week 16, or, for as long as the patient is in the study). A further outcome measure for the study is relative change from baseline in alanine aminotransferase (ALT) levels, as compared to baseline (e.g., from baseline day 1 to week 16, or, for as long as the patient is in the study). A further outcome measure for the study is relative change from baseline in gamma glutamyl transferase (GGT) levels, as compared to baseline (e.g., from baseline day 1 to week 16, or, for as long as the patient is in the study). A further outcome measure for the study is relative change from baseline in enhanced liver fibrosis score (ELF), as compared to baseline (e.g., from baseline day 1 to week 16, or, for as long as the patient is in the study). ELF numerical values are calculated from serum measurements of hyaluronic acid (HA), tissue inhibitor of metalloproteinases-1 (TIMP-1), and type III procollagen (PIIINP) using the formula: ELF score=2.494+0.846 In [HA]+0.735 In [PIIINP]+0.391 In [TIMP-1], and range on a continuous scale. Liver fibrosis is unlikely with scores <6.7 and increasingly likely with higher scores.

The study is expected to provide evidence that administration of miricorilant is safe, and does not cause unacceptable amounts or levels of adverse reactions in patients. The study is also expected to provide evidence of the reduction of liver fat in NASH patients receiving miricorilant as compared to baseline levels of liver fat. The study is expected to provide evidence of the reduction of ELF in NASH patients receiving miricorilant daily, as compared to baseline levels of ELF. The study is expected to provide evidence of safe or beneficial changes in AST, ALT, GGT, over the course of treatment for NASH patients receiving miricorilant daily.

Example 4

A description of a clinical trial for evaluating the clinical benefits and effects of miricorilant treatment administered to patients suffering from non-alcoholic steatohepatitis (NASH) is provided herein. Patients 18 to 75 years of age having a diagnosis of NASH based on a biopsy obtained within the last year, or having a diagnosis of presumed NASH based on blood tests and scans, may be included in the study. The study is designed to assess the safety, efficacy and pharmacokinetics (PK) of miricorilant in patients with presumed Nonalcoholic Steatohepatitis (NASH). Patients who meet the criteria for the study are enrolled on Day 1 into 1 of 6 cohorts and receive:

Cohort 1—a once-daily dose of 150 mg of miricorilant for 24 weeks; in alternative embodiments, the dose is 75 mg or is 100 mg miricorilant.

Cohort 2—a once-daily dose of 150 mg of miricorilant, for 12 weeks; in an alternative embodiments, the dose is 75 mg or is 100 mg miricorilant.

Cohort 3—a once-daily dose of 100 mg of miricorilant for 2 weeks, followed by 10 weeks of dosing at 100 mg miricorilant every Monday, Wednesday and Friday; in alternative embodiments, the dose is 75 or is 150 mg miricorilant;

Cohort 4—a daily dose of 100 mg of miricorilant over 2 weeks, followed by 10 weeks of dosing at 100 mg miricorilant every Monday and Friday; in alternative embodiments, the dose is 75 mg or is 150 mg miricorilant;

Cohort 5—100 mg of miricorilant over 12 weeks every Monday, Wednesday and Friday; in alternative embodiments, the dose is 75 mg or is 150 mg miricorilant;

Cohort 6—100 mg of miricorilant administered every Monday and Friday for 12 weeks; in alternative embodiments, the dose is 75 mg or is 150 mg miricorilant.

Figure 9:
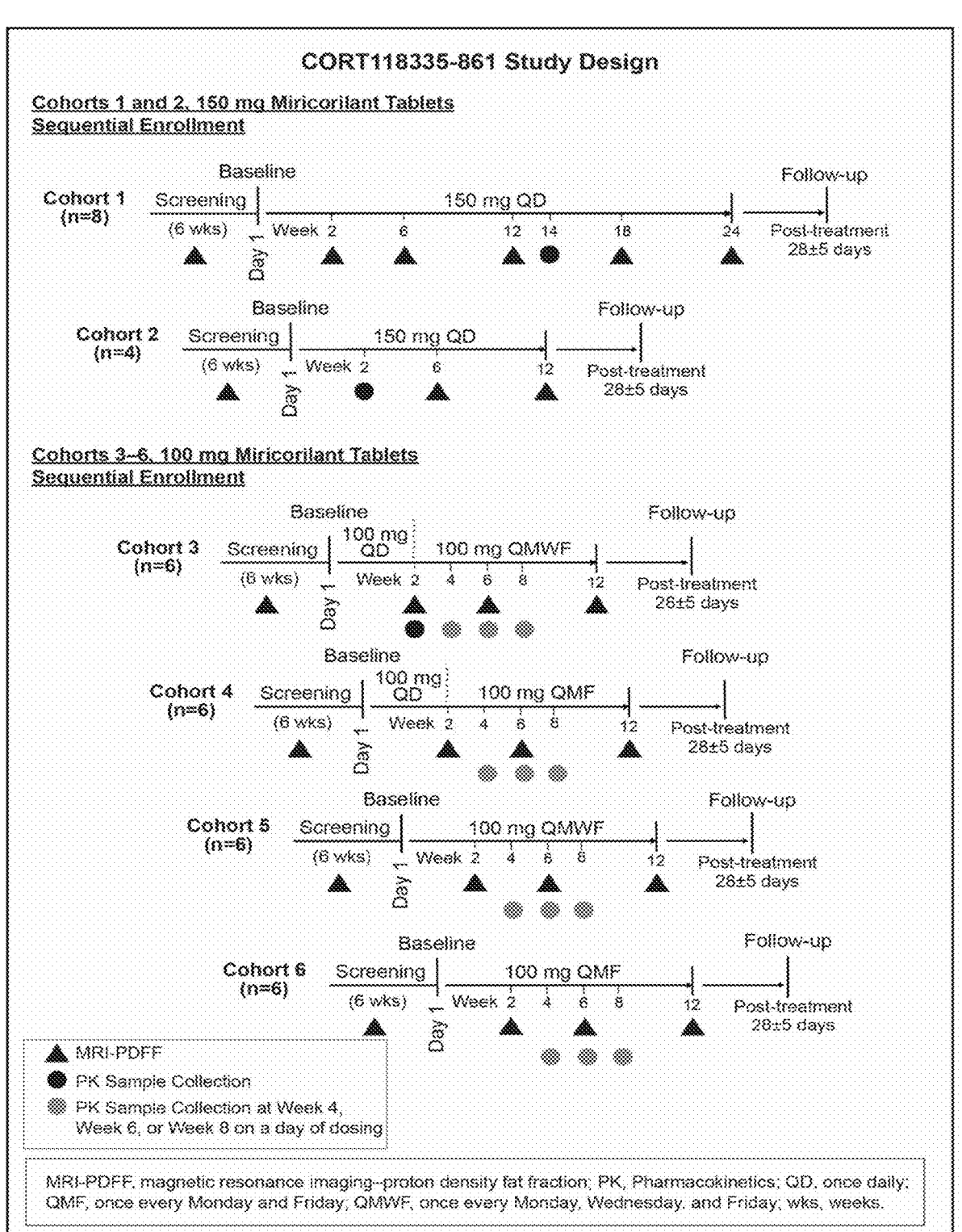
FIG. 9 provides a graphic illustration of the design of the study discussed in Example 4.

A schematic representation of the timeline of screening, miricorilant administration, sample collection, and post-treatment activities planned for the several cohorts of the study described in Example 4 is presented in FIG. 9.

A primary outcome measure for the study is relative change from baseline in liver fat content, assessed by MRI-PDFF compared to baseline (e.g., from baseline day 1 to week 12, or, for as long as the patient is in the study if the patient receives fewer than the scheduled 12 or 24 weeks of treatment). A further outcome measure for the study is relative change from baseline in aspartate aminotransferase (AST) levels, as compared to baseline (e.g., from baseline day 1 to week 12, or, for as long as the patient is in the study). A further outcome measure for the study is relative change from baseline in alanine aminotransferase (ALT) levels, as compared to baseline (e.g., from baseline day 1 to week 12, or, for as long as the patient is in the study). A further outcome measure for the study is relative change from baseline in gamma glutamyl transferase (GGT) levels, as compared to baseline (e.g., from baseline day 1 to week 12, or, for as long as the patient is in the study). A further outcome measure for the study is relative change from baseline in enhanced liver fibrosis score (ELF), as compared to baseline (e.g., from baseline day 1 to week 12, or, for as long as the patient is in the study). ELF numerical values are calculated from serum measurements of hyaluronic acid (HA), tissue inhibitor of metalloproteinases-1 (TIMP-1), and type III procollagen (PIIINP) using the formula: ELF score=2.494+0.846 In [HA]+0.735 In [PIIINP]+0.391 In [TIMP-1], and range on a continuous scale. Liver fibrosis is unlikely with scores <6.7 and increasingly likely with higher scores.

The study is expected to provide evidence of the reduction of liver fat in NASH patients receiving 100 mg and 150 mg doses of miricorilant daily, or three times a week, or twice a week, as compared to baseline levels of liver fat. The study is expected to provide evidence of the reduction of ELF in NASH patients receiving 100 mg and 150 mg doses of miricorilant daily, or three times a week, or twice a week, as compared to baseline levels of ELF. The study is expected to provide evidence of safe or beneficial changes in AST, ALT, GGT, over the course of treatment for NASH patients receiving 100 mg and 150 mg doses of miricorilant daily, or three times a week, or twice a week.

Example 5

A description of a clinical trial for evaluating the clinical benefits and effects of miricorilant treatment administered to patients suffering from non-alcoholic steatohepatitis (NASH) is provided herein. Patients 18 to 75 years of age having a diagnosis of NASH based on a biopsy obtained within the last year, or having a diagnosis of presumed NASH based on blood tests and scans, may be included in the study. The study is designed to assess the safety, efficacy and pharmacokinetics (PK) of miricorilant in patients with presumed Nonalcoholic Steatohepatitis (NASH). Patients who meet the criteria for the study are enrolled on Day 1 into 1 of 4 cohorts and receive:

Cohort 1—a once-daily dose of 10 mg of miricorilant for 3 months or 12 weeks; in an alternative embodiment, the dose is 25 mg miricorilant;

Cohort 2—a once-daily dose of 10 mg of miricorilant for 2 weeks, followed by 10 weeks of dosing at 10 mg miricorilant every Monday, Wednesday and Friday; in an alternative embodiment, the dose is 25 mg miricorilant;

Cohort 3—a daily dose of 10 mg of miricorilant over 2 weeks, followed by 10 weeks of dosing at 10 mg miricorilant every Monday and Friday; in an alternative embodiment, the dose is 25 mg miricorilant;

Cohort 4—a once-daily dose of 50 mg of miricorilant for 3 months or 12 weeks.

Cohort 5—a once-daily dose of 50 mg of miricorilant for 2 weeks, followed by 10 weeks of dosing at 50 mg miricorilant every Monday, Wednesday and Friday;

Cohort 6—a daily dose of 50 mg of miricorilant over 2 weeks, followed by 10 weeks of dosing at 50 mg miricorilant every Monday and Friday;

A primary outcome measure for the study is relative change from baseline in liver fat content, assessed by MRI-PDFF compared to baseline (e.g., from baseline day 1 to week 12, or, for as long as the patient is in the study if the patient fewer than the scheduled 12 of treatment). Further outcome measures include relative change from baseline in AST or ALT levels, or both; relative change from baseline in GGT levels, as compared to baseline; and relative change from baseline in ELF, as compared to baseline (where ELF is defined, measured, and evaluated as discussed above).

The study is expected to provide evidence of safe reduction of liver fat in NASH patients receiving 10 mg (or 25 mg) and 50 mg doses of miricorilant daily, or three times a week, or twice a week, as compared to baseline levels of liver fat. The study is expected to provide evidence of safe reduction of ELF, and to provide evidence of safe or beneficial changes in AST, ALT, GGT, over the course of treatment for NASH patients receiving 10 mg (or 25 mg) and 50 mg doses of miricorilant daily, or three times a week, or twice a week.

Example 6

This example presents results from a Phase 2a Study of Miricorilant in Patients with Presumed NASH.

This study was a double-blind, multi-center, placebo-controlled, randomized 3-arm phase 2a study (NCT03823703) conducted to assess the safety and efficacy of miricorilant in reducing liver fat content (LFC) in patients with presumed NASH. Adult patients (18-75 years) with presumed NASH were randomized 1:1:1 to miricorilant 600 mg daily, miricorilant 900 mg daily, or placebo for 12 weeks. Miricorilant treatment for 30-44 days resulted in large, rapid reductions in LFC in 4 patients (−39% to −74% reduction) with an associated isolated rise in ALT and AST. No significant change in ALP or bilirubin levels occurred; no patient met Hy's Law criteria; Transaminase elevations resolved rapidly in all patients upon discontinuation of miricorilant. Abbreviations used in this Example and in the Figures include: ALP, alkaline phosphatase; ALT, alanine aminotransferase; AST, aspartate aminotransferase; ELF, enhanced liver fibrosis; LFC, liver fat content; NASH, non-alcoholic steatohepatitis; ULN, upper limit of normal; AUC, area under the concentration-time curve; $C_{max}$, maximum concentration; EOT, end of treatment; GGT, gamma-glutamyltransferase; INR, international normalized ratio; MRI-PDFF, magnetic resonance imaging-proton density fat fraction; pt, patient; SD, standard deviation; ULN, upper limit of normal; Wk, week.

Key inclusion criteria included that the patients be adults between 18-75 years old; be presumed to suffer from NASH with fibrosis; have LFC as measured by MRI-PDFF≥8%; have levels of AST<5×ULN and ALT<5×ULN; and have eGFR>60 mL/min/1.73 m². Primary endpoints included relative change in LFC from baseline by MRI-PDFF. Secondary endpoints included change from baseline in AST, ALT, GGT, and change from baseline in ELF score.

Patients were divided into different cohorts and received different regimens of miricorilant. The cohorts included patients receiving 30 mg miricorilant once per day; patients receiving 50 mg miricorilant once per day; patients receiving 100 mg miricorilant once per day; patients receiving 150 mg miricorilant once per day; patients receiving 100 mg miricorilant on Mondays, Wednesdays, and Fridays; patients receiving 100 mg miricorilant on Mondays and Fridays; and patients receiving 200 mg miricorilant once per week. Patients receiving 100 mg miricorilant on Mondays and Fridays were termed "Cohort 6".

Patients exhibited reductions in liver fat, and exhibited improvements in lipids, glycemic measures, and other indicators of improvement due to miricorilant treatment. The greatest reductions in LFC by week 12 observed in Cohort 6, with miricorilant 100 mg twice weekly (mean % change from baseline=−28.2%). The greatest reductions in LFC by week 6 was observed with daily doses of miricorilant 50-150 mg (mean % change from baseline=−22.3%). However, these patients were more likely to interrupt or discontinue study drug prior to week 12 due to concurrent transaminase elevation.

An important result of these studies is the finding that if, during miricorilant treatment for fatty liver disease, ALT and/or AST levels remain below 3 times normal, the weight loss is significant, and reductions in liver fat and other measures of fatty liver disease are significant. For these patients, miricorilant administration can be continued without interruption.

A further important result of these studies is the finding that if ALT and/or AST levels rise above 3 times normal, the weight loss is even greater than for the other group, and that these patients benefit from an interruption in miricorilant administration (e.g., for three weeks, or for four weeks, or for 7 weeks, or for other period of time), and then miricorilant administration can be resumed and can continue in treating those patients.

As shown in FIG. 10, measures of liver fibrosis were reduced by miricorilant treatment. The graph shows MRI-PDFF and liver enzyme levels as a function of time during miricorilant treatment, for three groups of patients: patients who did not appear to respond to miricorilant treatment (non-responders); patients who did respond to miricorilant treatment, and did not have increased liver enzyme levels that exceeded 3 times normal liver enzyme levels; and patients who did respond to miricorilant treatment, and whose liver enzyme levels increased to greater than 3 times normal liver enzyme levels.

As shown in FIG. 10, treatment non-responders did not experience a rise in transaminase levels. However, treatment responders without ALT>3×ULN had a mean reduction in LFC of −25.5% at Week 6. Treatment responders with ALT>3×ULN had a faster decline in LFC loss, mean reduction in LFC of −52.6% at Week 6. Responders with ALT>3× ULN slope −8.76, responders without ALT>3×ULN slope −4.24. Patients with a more gradual weekly rate of LFC loss were less likely to experience a corresponding rise in ALT.

As shown in FIG. 11, which provides a scatterplot of patient body weight as a function of MRI-PDFF percentage change from baseline, reductions in liver fat content was unrelated to changes in body weight. The top group of dots with its line going through those dots indicated non-responders; the bottom group of dots, with its line going through those dots indicates MRI-PDFF responders with ALT>3 time the upper limit of normal. The middle group of dots, with its line going through those dots indicates MRI-PDFF responders with ALT less than or equal to 3 time the upper limit of normal.

FIG. 12 provides a table showing liver fat content for patients receiving miricorilant treatment whose miricorilant treatments were stopped for a period of time (7 weeks, 4 weeks, and 3 weeks), and then resumed.

FIG. 13 provides a plot of MRI-PDFF (top line beginning at week 0) and liver enzyme alanine aminotransferase (ALT; bottom line beginning at week 0) for a patient who received miricorilant treatment that included a cessation of miricorilant treatment from week 7 to week 10. Total bilirubin, direct bilirubin, ALP, INR were within normal limits. GGT was elevated at baseline (peak 88 U/L at Wk 10); at other weeks it was below baseline. Eosinophils (%) baseline 7.3, decreased to 2.2 at Wk 2 and increased Wk 3 (peak 4.3), decreased Wk 8 (2.0) and stable until EOT. Pharmacokinetics: $C_{max}$ 404 ng/mL, AUC 5897.19 h*ng/mL.

FIG. 14 provides a bar graph illustrating the reductions in liver fat content (LFC) over the course of twelve weeks of miricorilant treatment in patients receiving 100 mg of miricorilant twice per week (on Mondays and on Fridays). These data shown are for those 5 patients in cohort 6 who received ≥1 dose of study drug, remained on trial for ≥6 weeks, and had a 12 week MRI-PDFF assessment. One patient discontinued at week 6 (was lost to follow-up) and is not included.

FIG. 15 provides bar graphs illustrating the reductions in liver fat content (LFC) as measured by MRI-PDFF and in liver enzyme levels (alanine aminotransferase (ALT) and aspartase aminotransferase (AST)) over the course of twelve weeks of miricorilant treatment in patients receiving 100 mg of miricorilant twice per week (on Mondays and on Fridays).

FIG. 16 provides a bar graph illustrating reductions in lipid levels (low density lipoprotein (LDL) and very low density lipoprotein (VLDL)) in patients receiving 100 mg of miricorilant twice per week (on Mondays and on Fridays).

FIG. 17 provides bar graphs illustrating reductions in glycemic markers in patients receiving 100 mg of miricorilant twice per week (on Mondays and on Fridays). HOMA-IR is an acronym for Homeostatic Model Assessment of Insulin Resistance.

FIG. 18 provides a bar graph illustrating reductions in fibrosis markers in patients receiving 100 mg of miricorilant twice per week (on Mondays and on Fridays). ELF is an abbreviation for enhanced liver fibrosis.

FIG. 19 illustrates a clinical trial study plan for evaluating the effects of administration of 100 mg of miricorilant twice per week (on Mondays and on Fridays), as compared to placebo, in patients suffering from noncirrhotic NASH.

These results show that miricorilant administered as indicated above, including as administered at 100 mg twice weekly was safe, well tolerated, and resulted in reduced LFC and improved hepatic, lipid, and glycemic markers. This dosing schedule provided a gradual reduction in liver fat of −30% over 12 weeks without an associated rise in hepatic transaminase levels. Across all cohorts in this study, responders receiving intermittent miricorilant lost LFC more gradually and were less likely to have a rise in ALT>3×ULN compared to daily dosing. Miricorilant 100 mg twice weekly will be evaluated further in a placebo-controlled phase 2b study (MONARCH, NCT06108219) to assess miricorilant's efficacy and safety for the treatment of biopsy-confirmed NASH.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All patents, patent publications, publications, and patent applications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of reducing liver fat in a patient in need thereof, comprising intermittently administering to the patient an effective amount of the nonsteroidal glucocorticoid receptor modulator (GRM) (E)-6-(4-Phenylcyclohexyl)-5-(3-trifluoromethylbenzyl)-1H-pyrimidine-2,4-di-one ("miricorilant"), which has the structure:

Wherein said intermittent administration comprises:

Administering miricorilant two or three times per week for at least 2 weeks;

Determining blood levels of ALT, AST, or both;

Interrupting said administration of miricorilant for at least one week; and

Resuming miricorilant administration two or three times per week for at least two weeks, effective to reduce the amount of liver fat in the patient.

2. The method of claim 1, wherein the patient suffers from a non-alcoholic fatty liver disease (NAFLD).

3. The method of claim 2, wherein the non-alcoholic fatty liver disease is selected from nonalcoholic steatohepatitis (NASH) and nonalcoholic cirrhosis.

4. The method of claim 1, wherein the patient suffers from an alcohol related fatty liver disease (ARLD).

5. The method of claim 4, wherein the alcohol related fatty liver disease is selected from alcohol fatty liver disease (AFL), alcoholic steatohepatitis (ASH), and alcoholic cirrhosis).

6. The method of claim 1, wherein the patient suffers from liver fibrosis.

7. The method of claim 1, wherein said miricorilant is administered orally.

8. The method of claim 1, wherein said miricorilant is administered at a dose selected from 50 mg, 100 mg, and 150 mg.

9. The method of claim 1, wherein said miricorilant is administered twice weekly.

10. The method of claim 1, wherein liver enzyme levels of said patient are measured, and administration of miricorilant is interrupted for at least one week if the levels of alanine aminotransferase (ALT) or of aspartate aminotransferase (AST) are found to be greater than 3 time the normal level of those enzymes.

11. The method of claim 1, wherein said liver disease characterized by abnormally high levels of liver fat is further characterized by abnormal or excessive levels of one or more of liver degeneration, liver weight, liver collagen, and liver galectin, wherein said treatment is effective to normalize or reduce said abnormal or excessive levels of liver degeneration, liver weight, liver collagen, or liver galectin.

\* \* \* \* \*